United States Patent
Brenchley et al.

(10) Patent No.: US 7,276,502 B2
(45) Date of Patent: Oct. 2, 2007

(54) THIAZOLES USEFUL AS INHIBITORS OF PROTEIN KINASES

(75) Inventors: Guy Brenchley, Grove Wantage (GB); Luc J. Farmer, Foxboro, MA (US); Edmund M. Harrington, Plymouth, MA (US); Ronald Knegtel, Abingdon (GB); Michael O'Donnell, Abingdon (GB); Francesco G. Salituro, Marlboro, MA (US); John R. Studley, Abingdon (GB); Jian Wang, Newton, MA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 305 days.

(21) Appl. No.: 10/809,946

(22) Filed: Mar. 25, 2004

(65) Prior Publication Data

US 2005/0004150 A1    Jan. 6, 2005

Related U.S. Application Data

(60) Provisional application No. 60/457,468, filed on Mar. 25, 2003.

(51) Int. Cl.
  *C07D 417/04*  (2006.01)
  *A61K 31/506*  (2006.01)
(52) U.S. Cl. .............. 514/235.8; 514/252.19; 514/275; 544/122; 544/331
(58) Field of Classification Search ........ 544/122, 544/331; 514/235.8, 275, 252.19
See application file for complete search history.

(56) References Cited

U.S. PATENT DOCUMENTS

2003/0119856 A1    6/2003    Harrington et al.

FOREIGN PATENT DOCUMENTS

| WO | WO97/19065 A1 | 5/1997 |
| WO | WO 00/78731 A1 | 12/2000 |
| WO | WO 02/096905 A1 | 12/2002 |

OTHER PUBLICATIONS

Simone, Oncology: Introduction, Cecil Textbook of Medicine, 20th Edition, vol. 1, pp. 1004-1010, 1996.*
Casanova et al., PubMed Abstract (Rev Neurol. 28(9):909-15) May 1999.*
Traxler, Protein Tyrosine Kinase Inhibitors in Cancer Treatment, Expert Opinion on Therapeutic Patents, 7(6):571-588, 1997.*
Strawn, Laurie et al., "Tyrosine Kinases in Disease: Overview of Kinase Inhibitors as Therapeutic Agents and Current Drugs in Clinical Trials", Expert Opinion on Investigational Drugs, vol. 7, No. 4, pp. 553-573, (1998).

* cited by examiner

*Primary Examiner*—Deepak Rao
(74) *Attorney, Agent, or Firm*—Daniel A Pearson

(57) ABSTRACT

The present invention relates to compounds useful of inhibitors of protein kinases. The invention also provides pharmaceutically acceptable compositions comprising said compounds and methods of using the compositions in the treatment of various disease, conditions, or disorders.

27 Claims, No Drawings

US 7,276,502 B2

THIAZOLES USEFUL AS INHIBITORS OF PROTEIN KINASES

CROSS-REFERENCE TO RELATED APPLICATIONS

The present application claims priority under 35 U.S.C. §119 to U.S. Provisional Application No. 60/457,468, filed Mar. 25, 2003, entitled "Thiazoles Useful as Inhibitors of Protein Kinases", the entire contents of which is hereby incorporated by reference.

TECHNICAL FIELD OF THE INVENTION

The present invention relates to compounds useful as inhibitors of protein kinases. The invention also provides pharmaceutically acceptable compositions comprising the compounds of the invention and methods of using the compositions in the treatment of various disorders.

BACKGROUND OF THE INVENTION

The search for new therapeutic agents has been greatly aided in recent years by a better understanding of the structure of enzymes and other biomolecules associated with diseases. One important class of enzymes that has been the subject of extensive study is protein kinases.

Protein kinases constitute a large family of structurally related enzymes that are responsible for the control of a variety of signal transduction processes within the cell. (See, Hardie, G. and Hanks, S. *The Protein Kinase Facts Book, I and II*, Academic Press, San Diego, Calif.: 1995). Protein kinases are thought to have evolved from a common ancestral gene due to the conservation of their structure and catalytic function. Almost all kinases contain a similar 250-300 amino acid catalytic domain. The kinases may be categorized into families by the substrates they phosphorylate (e.g., protein-tyrosine, protein-serine/threonine, lipids, etc.). Sequence motifs have been identified that generally correspond to each of these kinase families (See, for example, Hanks, S. K., Hunter, T., *FASEB J.* 1995, 9, 576-596; Knighton et al., *Science* 1991, 253, 407-414; Hiles et al., *Cell* 1992, 70, 419-429; Kunz et al., *Cell* 1993, 73, 585-596; Garcia-Bustos et al., *EMBO J.* 1994, 13, 2352-2361).

In general, protein kinases mediate intracellular signaling by effecting a phosphoryl transfer from a nucleoside triphosphate to a protein acceptor that is involved in a signaling pathway. These phosphorylation events act as molecular on/off switches that can modulate or regulate the target protein biological function. These phosphorylation events are ultimately triggered in response to a variety of extracellular and other stimuli. Examples of such stimuli include environmental and chemical stress signals (e.g., osmotic shock, heat shock, ultraviolet radiation, bacterial endotoxin, and $H_2O_2$), cytokines (e.g., interleukin-1 (IL-1) and tumor necrosis factor α (TNF-α)), and growth factors (e.g., granulocyte macrophage-colony-stimulating factor (GM-CSF), and fibroblast growth factor (FGF)). An extracellular stimulus may affect one or more cellular responses related to cell growth, migration, differentiation, secretion of hormones, activation of transcription factors, muscle contraction, glucose metabolism, control of protein synthesis, and regulation of the cell cycle.

Many diseases are associated with abnormal cellular responses triggered by protein kinase-mediated events as described above. These diseases include, but are not limited to, autoimmune diseases, inflammatory diseases, bone diseases, metabolic diseases, neurological and neurodegenerative diseases, cancer, cardiovascular diseases, allergies and asthma, Alzheimer's disease, and hormone-related diseases. Accordingly, there has been a substantial effort in medicinal chemistry to find protein kinase inhibitors that are effective as therapeutic agents.

Syk is a tyrosine kinase that plays a critical role in FcεRI mediated mast cell degranulation and eosinophil activation. Accordingly, Syk kinase is implicated in various allergic disorders, in particular asthma. It has been shown that Syk binds to the phosphorylated gamma chain of the FcεR1 receptor via N-terminal SH2 domains and is essential for downstream signaling [Taylor et al., *Mol. Cell. Biol.* 1995, 15, 4149].

Inhibition of eosinophil apoptosis has been proposed as a key mechanism for the development of blood and tissue eosinophilia in asthma. IL-5 and GM-CSF are upregulated in asthma and are proposed to cause blood and tissue eosinophilia by inhibition of eosinophil apoptosis. Inhibition of eosinophil apoptosis has been proposed as a key mechanism for the development of blood and tissue eosinophilia in asthma. It has been reported that Syk kinase is required for the prevention of eosinophil apoptosis by cytokines (using antisense)[Yousefi et al., *J. Exp. Med.* 1996, 183, 1407].

The role of Syk in FcγR dependent and independent response in bone marrow derived macrophages has been determined by using irradiated mouse chimeras reconstituted with fetal liver cells from Syk −/− embryos. Syk deficient macrophages were defective in phagocytosis induced by FcγR but showed normal phagocytosis in response to complement [Kiefer et al., *Mol. Cell. Biol.* 1998, 18, 4209]. It has also been reported that aerosolized Syk antisense suppresses Syk expression and mediator release from macrophages [Stenton et al., *J. Immunology* 2000, 164, 3790].

ZAP-70 is essential for T-cell receptor signalling. Expression of this tyrosine kinase is restricted to T-cells and natural killer cells. The importance of ZAP-70 in T-cell function has been demonstrated in human patients, human T-cell lines and mice. Human patients suffering from a rare form of severe combined deficiency syndrome (SCID) possess homozygous mutations in ZAP-70 (reviewed in *Elder J. of Pediatric Hematology/Oncology* 1997, 19(6), 546-550). These patients have profound immunodeficiency, lack CD8+ T-cells and have CD4+ T-cells that are unresponsive to T-cell receptor (TCR)-mediated stimulation. Following TCR activation these CD4+ cells show severe defects in Ca2+ mobilization, tyrosine phosphorylation of down-stream substrates, proliferation and IL-2 production 70 (reviewed in *Elder Pediatric Research* 39, 743-748). Human Jurkat cells lacking ZAP-70 also provide important insights into the critical role of ZAP-70 in T-cell receptor signalling. A Jurkat clone (p116) with no detectable ZAP-70 protein was shown to have defects in T-cell receptor signalling which could be corrected by re-introduction of wild type ZAP-70 (Williams et al., *Molecular and Cellular Biology* 1998, 18 (3), 1388-1399). Studies of mice lacking ZAP-70 also demonstrate a requirement of ZAP-70 in T-cell receptor signalling. ZAP-70-deficient mice have profound defects in T-cell development and T-cell receptor signalling in thymocytes is impaired (Negishi et al., *Nature* 1995 376, 435-438).

The importance of the kinase domain in ZAP-70 function is demonstrated by studies of human patients and mice expressing identical mutations in the DLAARN motif within the kinase domain of ZAP-70. Inactivation of kinase activity by this mutation results in defective T-cell receptor signalling (Elder et al., *J. Immunology* 2001, 656-661). Catalytically inactive ZAP-70 (Lys369Arg) was also defective in restoring T-cell receptor signalling in a ZAP-70 deficient Jurkat cell clone (p116) (Williams et al., *Molecular and Cellular Biology* 1998, 18 (3), 1388-1399).

3

Accordingly, there is a great need to develop compounds useful as inhibitors of protein kinases. In particular, it would be desirable to develop compounds that are useful as inhibitors of SYK or ZAP-70, particularly given the inadequate treatments currently available for the majority of the disorders implicated in their activation.

SUMMARY OF THE INVENTION

It has now been found that compounds of this invention, and pharmaceutically acceptable compositions thereof, are effective as inhibitors of protein kinases. In certain embodiments, these compounds are effective as inhibitors of SYK or ZAP-70 protein kinases. These compounds have the general formula I:

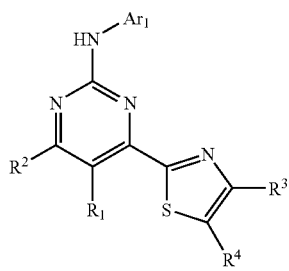

I or a pharmaceutically acceptable salt thereof, wherein $R^1$, $R^2$, $R^3$, $R^4$, and $Ar^1$ are as defined below.

These compounds and pharmaceutically acceptable compositions thereof are useful for treating or preventing a variety of diseases, disorders or conditions, including, but not limited to, immunodeficiency disorders, inflammatory diseases, allergic diseases, autoimmune diseases, proliferative disorders, immunologically-mediated diseases, or respiratory disorders, to name a few. The compounds provided by this invention are also useful for the study of kinases in biological and pathological phenomena; the study of intracellular signal transduction pathways mediated by such kinases; and the comparative evaluation of new kinase inhibitors.

DETAILED DESCRIPTION OF THE INVENTION

I General Description of Compounds of the Invention:
The present invention relates to a compound of formula I:

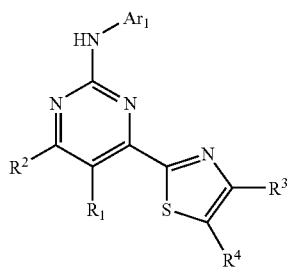

I or a pharmaceutically acceptable salt thereof, wherein:
$R^1$ and $R^2$ are each independently R', halogen, CN, $NO_2$, or TR, or $R^1$ and $R^2$ taken together form an optionally substituted saturated, partially unsaturated, or fully unsaturated 5- or 6-membered ring having 0-3 heteroatoms independently selected from N, O, or S;

4

T is an optionally substituted $C_1$-$C_4$ alkylidene chain wherein up to two methylene units of T are optionally and independently replaced by O, N(R'), C(O), S, SO, or $SO_2$;
$Ar^1$ is an optionally substituted ring selected from: an aryl group selected from a 5-6 membered monocyclic or an 8-10 membered bicyclic ring having 0-5 heteroatoms independently selected from nitrogen, oxygen, or sulfur; a 3-8-membered saturated or partially unsaturated monocyclic ring having 0-3 heteroatoms independently selected from nitrogen, oxygen, or sulfur; or an 8-10-membered saturated or partially unsaturated bicyclic ring system having 0-5 heteroatoms independently selected from nitrogen, oxygen, or sulfur; wherein $Ar^1$ is optionally substituted at one or more carbon atoms with 0-5 occurrences of -Q-$R^5$, and at one or more substitutable nitrogen atoms with —$R^6$ and each occurrence of $R^6$ is independently R', —COR', —$CO_2$($C_{1-6}$ aliphatic), —CON(R')$_2$, —$SO_2$N(R')$_2$, or —$SO_2$R';
$R^3$ and $R^4$ are each independently Z-$R^7$, or $R^3$ and $R^4$ are taken together to form an optionally substituted saturated or partially unsaturated, or fully unsaturated 3-8 membered ring having 0-3 heteroatoms independently selected from nitrogen, oxygen, or sulfur wherein said ring is optionally substituted with 0-5 independent occurrences of Y—$R^8$;
each occurrence of Q, Z, and Y is independently a bond or an optionally substituted $C_1$-$C_6$ alkylidene chain wherein up to two non-adjacent methylene units of Q are optionally replaced by CO, $CO_2$, COCO, CONR, OCONR, NRNR, NRNRCO, NRCO, $NRCO_2$, NRCONR, SO, $SO_2$, $NRSO_2$, $SO_2$NR, $NRSO_2$NR, O, S, or NR;
each occurrence of $R^5$, $R^7$ and $R^8$ is independently R', halogen, $NO_2$, CN, OR', SR', N(R')$_2$, NR'C(O)R', NR'C(O)N(R')$_2$, NR'$CO_2$R', C(O)R', $CO_2$R', OC(O)R', C(O)N(R')$_2$, OC(O)N(R')$_2$, SOR', $SO_2$R', $SO_2$N(R')$_2$, NR'$SO_2$R', NR'$SO_2$N(R')$_2$, PO(OR')$_2$, C(O)C(O)R', or C(O)$CH_2$C(O)R'; and
each occurrence of R' is independently hydrogen or an optionally substituted $C_{1-6}$ aliphatic group; and each occurrence of R' is independently hydrogen or an optionally substituted group selected from $C_{1-8}$ aliphatic, $C_{6-10}$ aryl, a heteroaryl ring having 5-10 ring atoms, or a heterocyclyl ring having 3-10 ring atoms, or wherein two occurrences of R' taken together, R and R' taken together, or two occurrences of R' taken together, form an optionally substituted saturated, partially unsaturated, or fully unsaturated 3-8 membered ring having 0-3 heteroatoms independently selected from nitrogen, oxygen, or sulfur;
provided that:
i) $R^3$ and $R^4$ are not simultaneously hydrogen; and
ii) when $R^3$ and $R^4$ are both methyl, or $R^3$ is methyl and $R^4$ is $(CH_2)_2OH$, then $Ar^1$ is not 3,4,5-trimethoxyphenyl.
2. Compounds and Definitions:
Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001, the entire contents of which are hereby incorporated by reference.

As described herein, compounds of the invention may optionally be substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle" "cycloaliphatic" or "cycloalkyl"), that has a single point of attachment to the rest of the molecule. Unless otherwise specified, aliphatic groups contain 1-20 aliphatic carbon atoms. In some embodiments, aliphatic groups contain 1-10 aliphatic carbon atoms. In other embodiments, aliphatic groups contain 1-8 aliphatic carbon atoms. In still other embodiments, aliphatic groups contain 1-6 aliphatic carbon atoms, and in yet other embodiments aliphatic groups contain 1-4 aliphatic carbon atoms. In some embodiments, "cycloaliphatic" (or "carbocycle" or "cycloalkyl") refers to a monocyclic $C_3$-$C_8$ hydrocarbon or bicyclic $C_8$-$C_{12}$ hydrocarbon that is completely saturated or that contains one or more units of unsaturation, but which is not aromatic, that has a single point of attachment to the rest of the molecule wherein any individual ring in said bicyclic ring system has 3-7 members. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

The term "heteroaliphatic", as used herein, means aliphatic groups wherein one or two carbon atoms are independently replaced by one or more of oxygen, sulfur, nitrogen, phosphorus, or silicon. Heteroaliphatic groups may be substituted or unsubstituted, branched or unbranched, cyclic or acyclic, and include "heterocycle", "heterocyclyl", "heterocycloaliphatic", or "heterocyclic" groups.

The term "heterocycle", "heterocyclyl", "heterocycloaliphatic", or "heterocyclic" as used herein means nonaromatic, monocyclic, bicyclic, or tricyclic ring systems in which one or more ring members is an independently selected heteroatom. In some embodiments, the "heterocycle", "heterocyclyl", "heterocycloaliphatic", or "heterocyclic" group has three to fourteen ring members in which one or more ring members is a heteroatom independently selected from oxygen, sulfur, nitrogen, or phosphorus, and each ring in the system contains 3 to 7 ring members.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

The term "unsaturated", as used herein, means that a moiety has one or more units of unsaturation.

The term "alkoxy", or "thioalkyl", as used herein, refers to an alkyl group, as previously defined, attached to the principal carbon chain through an oxygen ("alkoxy") or sulfur ("thioalkyl") atom.

The terms "haloalkyl", "haloalkenyl" and "haloalkoxy" means alkyl, alkenyl or alkoxy, as the case may be, substituted with one or more halogen atoms. The term "halogen" means F, Cl, Br, or I.

The term "aryl" used alone or as part of a larger moiety as in "aralkyl", "aralkoxy", or "aryloxyalkyl", refers to monocyclic, bicyclic, and tricyclic ring systems having a total of five to fourteen ring members, wherein at least one ring in the system is aromatic and wherein each ring in the system contains 3 to 7 ring members. The term "aryl" may be used interchangeably with the term "aryl ring". The term "aryl" also refers to heteroaryl ring systems as defined hereinbelow.

The term "heteroaryl", used alone or as part of a larger moiety as in "heteroaralkyl" or "heteroarylalkoxy", refers to monocyclic, bicyclic, and tricyclic ring systems having a total of five to fourteen ring members, wherein at least one ring in the system is aromatic, at least one ring in the system contains one or more heteroatoms, and wherein each ring in the system contains 3 to 7 ring members. The term "heteroaryl" may be used interchangeably with the term "heteroaryl ring" or the term "heteroaromatic".

An aryl (including aralkyl, aralkoxy, aryloxyalkyl and the like) or heteroaryl (including heteroaralkyl and heteroarylalkoxy and the like) group may contain one or more substituents. Suitable substituents on the unsaturated carbon atom of an aryl or heteroaryl group are selected from halogen; —$R^°$; —$OR^°$; —$SR^°$; 1,2-methylene-dioxy; 1,2-ethylenedioxy; phenyl (Ph) optionally substituted with $R^°$; —O(Ph) optionally substituted with $R^°$; —$(CH_2)_{1-2}$(Ph), optionally substituted with $R^°$; —CH=CH(Ph), optionally substituted with $R^°$; —$NO_2$; —CN; —$N(R^°)_2$; —$NR^°C(O)R^°$; —$NR^°C(O)N(R^°)_2$; —$NR^°CO_2R^°$; —$NR^°NR^°C(O)R^°$; —$NR^°NR^°C(O)N(R^°)_2$; —$NR^°NR^°CO_2R^°$; —C(O)C(O)$R^°$; —C(O)$CH_2$C(O)$R^°$; —$CO_2R^°$; —C(O)$R^°$; —C(O)N($R^°)_2$; —OC(O)N($R^°)_2$; —S(O)$_2R^°$; —$SO_2N(R^°)_2$; —S(O)$R^°$; —$NR^°SO_2N(R^°)_2$; —$NR^°SO_2R^°$; —C(=S)N($R^°)_2$; —C(=NH)—N($R^°)_2$; or —$(CH_2)_{0-2}NHC(O)R^°$ wherein each independent occurrence of $R^°$ is selected from hydrogen, optionally substituted $C_{1-6}$ aliphatic, an unsubstituted 5-6 membered heteroaryl or heterocyclic ring, phenyl, —O(Ph), or —$CH_2$(Ph), or, notwithstanding the definition above, two independent occurrences of $R^°$, on the same substituent or different substituents, taken together with the atom(s) to which each $R^°$ group is bound, form a 3-8-membered cycloalkyl, heterocyclyl, aryl, or heteroaryl ring having 0-3 heteroatoms independently selected from nitrogen, oxygen, or sulfur. Optional substituents on the aliphatic group of $R^°$ are selected from $NH_2$, NH($C_{1-4}$aliphatic), N($C_{1-4}$aliphatic)$_2$, halogen, $C_{1-4}$aliphatic, OH, O($C_{1-4}$aliphatic), NO₂, CN, CO₂H, CO₂(C₁₋₄aliphatic), O(haloC₁₋₄ aliphatic), or haloC₁₋₄aliphatic, wherein each of the foregoing C₁₋₄aliphatic groups of R° is unsubstituted.

An aliphatic or heteroaliphatic group, or a non-aromatic heterocyclic ring may contain one or more substituents. Suitable substituents on the saturated carbon of an aliphatic or heteroaliphatic group, or of a non-aromatic heterocyclic ring are selected from those listed above for the unsaturated carbon of an aryl or heteroaryl group and additionally include the following: =O, =S, =NNHR*, =NN(R*)₂, =NNHC(O)R*, =NNHCO₂(alkyl), =NNHSO₂(alkyl), or =NR*, where each R* is independently selected from hydrogen or an optionally substituted C₁₋₆ aliphatic. Optional substituents on the aliphatic group of R* are selected from NH₂, NH(C₁₋₄ aliphatic), N(C₁₋₄ aliphatic)₂, halogen, C₁₋₄ aliphatic, OH, O(C₁₋₄ aliphatic), NO₂, CN, CO₂H, CO₂(C₁₋₄ aliphatic), O(halo C₁₋₄ aliphatic), or halo (C₁₋₄ aliphatic), wherein each of the foregoing C₁₋₄aliphatic groups of R* is unsubstituted.

Optional substituents on the nitrogen of a non-aromatic heterocyclic ring are selected from —R⁺, —N(R⁺)₂, —C(O)R⁺, —CO₂R⁺, —C(O)C(O)R⁺, —C(O)CH₂C(O)R⁺, —SO₂R⁺, —SO₂N(R⁺)₂, —C(=S)N(R⁺)₂, —C(=NH)—N(R⁺)₂, or —NR⁺SO₂R⁺; wherein R⁺ is hydrogen, an optionally substituted C₁₋₆ aliphatic, optionally substituted phenyl, optionally substituted —O(Ph), optionally substituted —CH₂(Ph), optionally substituted —(CH₂)₁₋₂(Ph); optionally substituted —CH=CH(Ph); or an unsubstituted 5-6 membered heteroaryl or heterocyclic ring having one to four heteroatoms independently selected from oxygen, nitrogen, or sulfur, or, notwithstanding the definition above, two independent occurrences of R⁺, on the same substituent or different substituents, taken together with the atom(s) to which each R⁺ group is bound, form a 3-8-membered cycloalkyl, heterocyclyl, aryl, or heteroaryl ring having 0-3 heteroatoms independently selected from nitrogen, oxygen, or sulfur. Optional substituents on the aliphatic group or the phenyl ring of R⁺ are selected from NH₂, NH(C₁₋₄ aliphatic), N(C₁₋₄ aliphatic)₂, halogen, C₁₋₄ aliphatic, OH, O(C₁₋₄ aliphatic), NO₂, CN, CO₂H, CO₂(C₁₋₄ aliphatic), O(halo C₁₋₄ aliphatic), or halo(C₁₋₄ aliphatic), wherein each of the foregoing C₁₋₄aliphatic groups of R⁺ is unsubstituted.

The term "alkylidene chain" refers to a straight or branched carbon chain that may be fully saturated or have one or more units of unsaturation and has two points of attachment to the rest of the molecule.

As detailed above, in some embodiments, two independent occurrences of R° (or R⁺, or any other variable similarly defined herein), are taken together together with the atom(s) to which each variable is bound to form a 3-8-membered cycloalkyl, heterocyclyl, aryl, or heteroaryl ring having 0-3 heteroatoms independently selected from nitrogen, oxygen, or sulfur. Exemplary rings that are formed when two independent occurrences of R° (or R⁺, or any other variable similarly defined herein) are taken together with the atom(s) to which each variable is bound include, but are not limited to the following: a) two independent occurrences of R° (or R⁺, or any other variable similarly defined herein) that are bound to the same atom and are taken together with that atom to form a ring, for example, N(R°)₂, where both occurrences of R° are taken together with the nitrogen atom to form a piperidin-1-yl, piperazin-1-yl, or morpholin-4-yl group; and b) two independent occurrences of R° (or R⁺, or any other variable similarly defined herein) that are bound to different atoms and are taken together with both of those atoms to form a ring, for example where a phenyl group is substituted with two occurrences of OR°

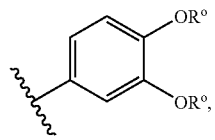

these two occurrences of R° are taken together with the oxygen atoms to which they are bound to form a fused 6-membered oxygen containing ring:

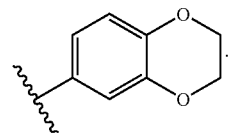

It will be appreciated that a variety of other rings can be formed when two independent occurrences of R° (or R⁺, or any other variable similarly defined herein) are taken together with the atom(s) to which each variable is bound and that the examples detailed above are not intended to be limiting.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a ¹³C- or ¹⁴C-enriched carbon are within the scope of this invention. Such compounds are useful, for example, as analytical tools or probes in biological assays.

3. Description of Exemplary Compounds:

As described generally above for compounds of general formula I, Ar¹ is an optionally substituted ring selected from: an aryl group selected from a 5-6 membered monocyclic or an 8-10 membered bicyclic ring having 0-5 heteroatoms independently selected from nitrogen, oxygen, or sulfur; a 3-8-membered saturated or partially unsaturated monocyclic ring having 0-3 heteroatoms independently selected from nitrogen, oxygen, or sulfur; or an 8-10-membered saturated or partially unsaturated bicyclic ring system having 0-5 heteroatoms independently selected from nitrogen, oxygen, or sulfur, wherein Ar¹ is optionally substituted at one or more carbon atoms with 0-5 occurrences of -Z-R⁵, and at one or more substitutable nitrogen atoms with —R⁶.

Preferred Ar¹ groups of formula I are optionally substituted rings selected from:
(a) a phenyl, indanyl, or naphthyl ring;
(b) a 5-6 membered heterocyclic ring having 1-3 heteroatoms independently selected from nitrogen, oxygen, or sulfur; or (c) a 5-6 membered monocyclic or 9-10 membered bicyclic heteroaryl ring having 1-3 heteroatoms independently selected from oxygen, nitrogen, or sulfur.

More preferred Ar¹ groups of formula I are optionally substituted rings selected from:

(a) a phenyl ring;
(b) a 5-6 membered heterocyclic ring having 1-3 heteroatoms independently selected from nitrogen, oxygen, or sulfur; or
(c) a 5-6 membered monocyclic heteroaryl ring having 1-3 heteroatoms independently selected from oxygen, nitrogen, or sulfur.

In still other embodiments, Ar¹ groups of formula I are optionally substituted rings selected from any one of a-bb:

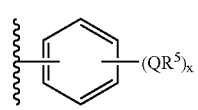
a

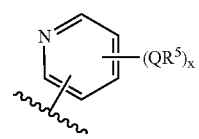
b

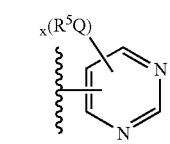
c

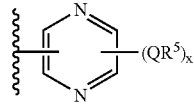
d

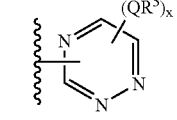
e

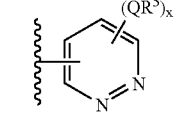
f

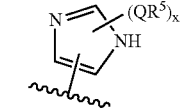
g

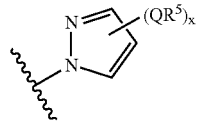
h

-continued

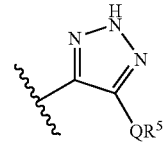
i

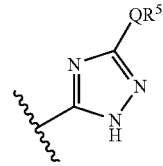
j

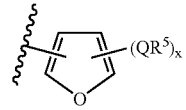
k

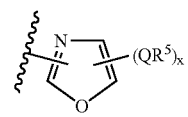
l

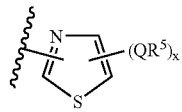
m

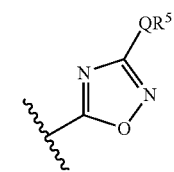
n

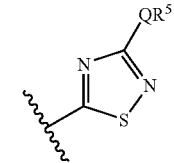
o

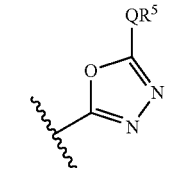
p

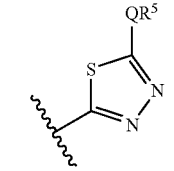
q

-continued

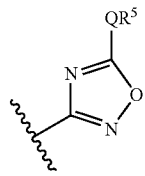
r

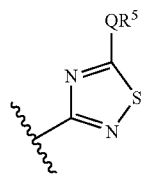
s

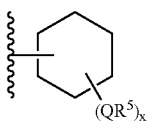
t

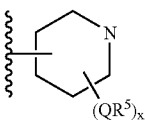
u

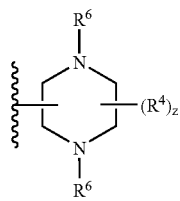
v

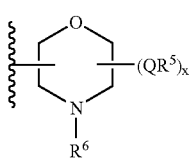
w

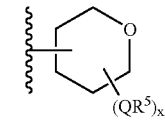
x

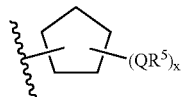
y

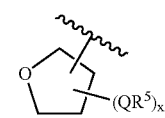
z

bb aa

-continued wherein x is 0-5.

Most preferred $Ar^1$ rings are phenyl, pyrimidinyl, or pyridyl.

In still other embodiments, for compounds described generally above and in classes and subclasses herein, $Ar^1$ is not 3,4,5-trimethoxyphenyl.

As described generally above for compounds of general formula I, $Ar^1$ is optionally substituted with up to 5 independent occurrences of $Q-R^5$, wherein each occurrence of Q is independently a bond or is an optionally substituted $C_1-C_6$ alkylidene chain wherein up to two non-adjacent methylene units of Q are optionally replaced by CO, $CO_2$, COCO, CONR, OCONR, NRNR, NRNRCO, NRCO, $NRCO_2$, NRCONR, SO, $SO_2$, $NRSO_2$, $SO_2NR$, $NRSO_2NR$, O, S, or NR; and each occurrence of $R^5$ is independently R', halogen, $NO_2$, CN, OR', SR', $N(R')_2$, NR'C(O)R', $NR'C(O)N(R')_2$, $NR'CO_2R'$, C(O)R', $CO_2R'$, OC(O)R', $C(O)N(R')_2$, $OC(O)N(R')_2$, SOR', $SO_2R'$, $SO_2N(R')_2$, $NR'SO_2R'$, $NR'SO_2N(R')_2$, $PO(OR')_2$, C(O)C(O)R', or $C(O)CH_2C(O)R'$. In preferred embodiments, x is 0, 1, 2, or 3. In other preferred embodiments, x is 1, 2, or 3.

In yet other preferred embodiments, Q is independently a bond or is an optionally substituted $C_1-C_4$ alkylidene chain wherein up to two non-adjacent methylene units of Q are optionally replaced by CO, $CO_2$, CONR, OCONR, NRCO, $NRCO_2$, $NRSO_2$, $SO_2NR$, O, S, or NR; and each occurrence of $R^5$ is independently selected from R', halogen, $NO_2$, CN, OR', SR', $N(R')_2$, NR'C(O)R', $NR'C(O)N(R')_2$, $NR'CO_2R'$, C(O)R', $CO_2R'$, OC(O)R', $C(O)N(R')_2$, $OC(O)N(R')_2$, SOR', $SO_2R'$, $SO_2N(R')_2$, $NR'SO_2R'$, $NR'SO_2N(R')_2$, $PO(OR')_2$, C(O)C(O)R', or $C(O)CH_2C(O)R'$, and x is 0, 1, 2, or 3. In preferred embodiments, x is 1, 2, or 3.

Preferred $Q-R^5$ substituents on $Ar^1$ are $CH_2$halogen, halogen, $CH_2CN$, CN, $CH_2CO_2R'$, $CO_2R'$, $CH_2COR'$, COR', R', $CH_2NO_2$, $NO_2$, $CH_2OR'$, OR', $CH_2SR'$, SR', haloalkyl, $CH_2SO_2N(R')_2$, $SO_2N(R')_2$, $CH_2N(R')_2$, $N(R')_2$, NHCOR', $CH_2NHCOR'$, $CH_2PO(OR')_2$, $PO(OR')_2$, or two adjacent occurrences of $Q-R^5$, taken together with the atoms to which they are bound, form an optionally substituted saturated, partially unsaturated, or fully unsaturated 5-8-membered ring having 0-3 heteroatoms selected from nitrogen, oxygen, or sulfur.

More preferred $Q-R^5$ substituents on $Ar^1$ are fluoro, iodo, chloro, bromo, $COCH_3$, $CO_2CH_3$, $C_{1-4}$alkyl (for example, methyl, ethyl, propyl, cyclopropyl, n-butyl, cyclobuyl, or t-butyl), $NH_2$, $CH_2NH_2$, NHMe, $CH_2NHMe$, $N(Me)_2$, $CH_2N(Me)_2$, $N(Et)_2$, $CH_2N(Et)_2$, NH(phenyl), $CO(C_{1-4}$ alkyl), $CH_2CO(C_{1-4}$alkyl), $NHCO(C_{1-4}$alkyl), $CH_2NHCO(C_{1-4}$alkyl), CN, $CH_2CN$, OH, $C_{1-4}$alkoxy (for example, $OCH_3$, $OCH_2CH_3$, $O(CH_2)_2CH_3$, or $O(CH_2)_3CH_3$), optionally substituted benzyloxy, optionally substituted phenyloxy, $CF_3$, $SO_2NH_2$, $SO_2NHMe$, optionally substituted $SO_2$(phenyl), $SO_2(C_{1-4}$alkyl), $CONH_2$, $CH_2PO(OR')_2$, or an optionally substituted group selected from a saturated, partially unsaturated, or fully unsaturated 5- or 6-membered ring having 0-3 heteroatoms independently selected from nitrogen, oxygen, or sulfur. Other preferred $Ar^1$ substituents are those substituents where two adjacent occurrences of $Q-R^5$, taken together with the atoms to which they are bound, and include a fused optionally substituted saturated, partially unsaturated, or fully unsaturated 5- or 6-membered ring having 0-3 heteroatoms selected from nitrogen, oxygen, or sulfur. In more preferred embodiments, these fused substituents formed by two adjacent occurrences of Q-R$^5$ include an optionally substituted group selected from methylenedioxy, ethylenedioxy, propylenedioxy, thiazolyl, oxazolyl, pyrrolyl, pyrazolyl, imidazolyl, phenyl, pyridyl, pyrimidinyl, furyl, thiophene, pyran, pyrrolidinyl, piperidinyl, piperazinyl, or morpholinyl.

In yet other embodiments, Ar$^1$ is phenyl and is substituted with two occurrences (x=2) of Q-R$^5$ and Ar$^1$ is:

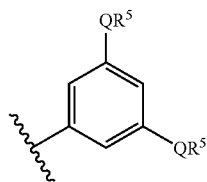

wherein each occurrence of QR$^5$ is independently CH$_2$halogen, halogen, CH$_2$CN, CN, CH$_2$CO$_2$R', CO$_2$R', CH$_2$COR', COR', R', CH$_2$NO$_2$, NO$_2$, CH$_2$OR', OR', CH$_2$SR', SR', haloalkyl, CH$_2$SO$_2$N(R')$_2$, SO$_2$N(R')$_2$, CH$_2$N(R')$_2$, N(R')$_2$, NHCOR', CH$_2$NHCOR', CH$_2$PO(OR')$_2$, PO(OR')$_2$. In certain preferred embodiments, each occurrence of QR$^5$ is independently fluoro, iodo, chloro, bromo, COCH$_3$, CO$_2$CH$_3$, C$_{1-4}$alkyl (for example, methyl, ethyl, propyl, cyclopropyl, n-butyl, cyclobuyl, or t-butyl), NH$_2$, CH$_2$NH$_2$, NHMe, CH$_2$NHMe, N(Me)$_2$, CH$_2$N(Me)$_2$, N(Et)$_2$, CH$_2$N(Et)$_2$, NH(phenyl), CO(C$_{1-4}$alkyl), CH$_2$CO(C$_{1-4}$alkyl), NHCO(C$_{1-4}$alkyl), CH$_2$NHCO(C$_{1-4}$alkyl), CN, CH$_2$CN, OH, C$_{1-4}$alkoxy (for example, OCH$_3$, OCH$_2$CH$_3$, O(CH$_2$)$_2$CH$_3$, or O(CH$_2$)$_3$CH$_3$), optionally substituted benzyloxy, optionally substituted phenyloxy, CF$_3$, SO$_2$NH$_2$, SO$_2$NHMe, optionally substituted SO$_2$(phenyl), SO$_2$(C$_{1-4}$alkyl), CONH$_2$, CH$_2$PO(OR')$_2$, or an optionally substituted group selected from a saturated, partially unsaturated, or fully unsaturated 5- or 6-membered ring having 0-3 heteroatoms independently selected from nitrogen, oxygen, or sulfur. In still other preferred embodiments, both occurrences of QR$^5$ are methyl. In yet other embodiments, at least one occurrence of QR$^5$ is CF$_3$.

In yet other embodiments, Ar$^1$ is phenyl and is substituted with three occurrences (x=3) of Q-R$^5$ and Ar$^1$ is:

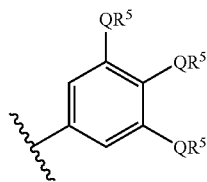

wherein each occurrence of QR$^5$ is independently CH$_2$halogen, halogen, CH$_2$CN, CN, CH$_2$CO$_2$R', CO$_2$R', CH$_2$COR', COR', R', CH$_2$NO$_2$, NO$_2$, CH$_2$OR', OR', CH$_2$SR', SR', haloalkyl, CH$_2$SO$_2$N(R')$_2$, SO$_2$N(R')$_2$, CH$_2$N(R')$_2$, N(R')$_2$, NHCOR', CH$_2$NHCOR', CH$_2$PO(OR')$_2$, PO(OR')$_2$. In certain preferred embodiments, each occurrence of QR$^5$ is independently fluoro, iodo, chloro, bromo, COCH$_3$, CO$_2$CH$_3$, C$_{1-4}$alkyl (for example, methyl, ethyl, propyl, cyclopropyl, n-butyl, cyclobuyl, or t-butyl), NH$_2$, CH$_2$NH$_2$, NHMe, CH$_2$NHMe, N(Me)$_2$, CH$_2$N(Me)$_2$, N(Et)$_2$, CH$_2$N(Et)$_2$, NH(phenyl), CO(C$_{1-4}$alkyl), CH$_2$CO(C$_{1-4}$alkyl), NHCO(C$_{1-4}$alkyl), CH$_2$NHCO(C$_{1-4}$alkyl), CN, CH$_2$CN, OH, C$_{1-4}$alkoxy (for example, OCH$_3$, OCH$_2$CH$_3$, O(CH$_2$)$_2$CH$_3$, or O(CH$_2$)$_3$CH$_3$), optionally substituted benzyloxy, optionally substituted phenyloxy, CF$_3$, SO$_2$NH$_2$, SO$_2$NHMe, optionally substituted SO$_2$(phenyl), SO$_2$(C$_{1-4}$alkyl), CONH$_2$, CH$_2$PO(OR')$_2$, or an optionally substituted group selected from a saturated, partially unsaturated, or fully unsaturated 5- or 6-membered ring having 0-3 heteroatoms independently selected from nitrogen, oxygen, or sulfur. In still other preferred embodiments, each occurrence of QR$^5$ is independently fluoro, iodo, chloro, bromo, COCH$_3$, CO$_2$CH$_3$, C$_{1-4}$alkyl (for example, methyl, ethyl, propyl, cyclopropyl, n-butyl, cyclobuyl, or t-butyl), NH$_2$, CH$_2$NH$_2$, NHMe, CH$_2$NHMe, N(Me)$_2$, CH$_2$N(Me)$_2$, N(Et)$_2$, CH$_2$N(Et)$_2$, NH(phenyl), CO(C$_{1-4}$alkyl), CH$_2$CO(C$_{1-4}$alkyl), NHCO(C$_{1-4}$alkyl), CH$_2$NHCO(C$_{1-4}$alkyl), CN, CH$_2$CN, OH, optionally substituted benzyloxy, optionally substituted phenyloxy, CF$_3$, SO$_2$NH$_2$, SO$_2$NHMe, optionally substituted SO$_2$(phenyl), SO$_2$(C$_{1-4}$alkyl), CONH$_2$, CH$_2$PO(OR')$_2$, or an optionally substituted group selected from a saturated, partially unsaturated, or fully unsaturated 5- or 6-membered ring having 0-3 heteroatoms independently selected from nitrogen, oxygen, or sulfur.

Each of the Q-R$^5$ substituents described above are also optionally further substituted with one or more groups independently selected from R, OR, N(R')$_2$, SO$_2$R, halogen, NO$_2$, CN, SR, SO$_2$N(R)$_2$, CO$_2$R, C(O)R, or oxo. In more preferred embodiments, each of the Q-R$^5$ groups described above are also optionally further substituted with one or two groups independently selected from methyl, ethyl, t-butyl, fluoro, chloro, bromo, oxo, CF$_3$, OMe, OEt, CN, SO$_2$Me, SO$_2$NH$_2$, NH$_2$, NHMe, N(Me)$_2$, SMe, SEt, OH, C(O)Me, NO$_2$, or CH$_2$OH.

As described generally above for compounds of general formula I, R$^1$ and R$^2$ are each independently R, halogen, CN, NO$_2$, or TR, or R$^1$ and R$^2$ taken together form an optionally substituted saturated, partially unsaturated, or fully unsaturated 5- or 6-membered ring having 0-3 heteroatoms independently selected from N, O, or S. Preferred R$^1$ and R$^2$ groups of formula I are hydrogen, N(R)$_2$, SR, OR, or TR, or R$^1$ and R$^2$, taken together form an optionally substituted saturated, partially unsaturated, or fully unsaturated 5-membered ring having 0-2 heteroatoms independently selected from N, O, or S. More preferred R$^1$ and R$^2$ groups are hydrogen, OH, CH$_3$, CH$_2$CH$_3$, OCH$_3$, CH$_2$OH, CH$_2$OCH$_3$, CH$_2$NH$_2$, CH$_2$NHCH$_3$, NH$_2$, or CH$_2$NH$_2$, or R$^1$ and R$^2$, taken together, form a fused optionally substituted pyrrolyl, pyrazolyl, or imidazolyl ring. Still other preferred groups include hydrogen, NH$_2$, or CH$_2$NH$_2$.

As described generally above for compounds of formula I, R$^3$ and R$^4$ are each independently Z-R$^7$, wherein Z is an optionally substituted C$_{1-6}$alkylidene chain wherein up to three non-adjacent methylene units are optionally replaced by CO, CO$_2$, COCO, CONR, OCONR, NRNR, NRNRCO, NRCO, NRCO$_2$, NRCONR, SO, SO$_2$, NRSO$_2$, SO$_2$NR, NRSO$_2$NR, O, S, or NR, and each occurrence of R$^7$ is independently R', halogen, NO$_2$, CN, OR', SR', N(R')$_2$, NR'C(O)R', NR'C(O)N(R')$_2$, NR'CO$_2$R', C(O)R', CO$_2$R', OC(O)R', C(O)N(R')$_2$, OC(O)N(R')$_2$, SOR', SO$_2$R', SO$_2$N(R')$_2$, NR'SO$_2$R', NR'SO$_2$N(R')$_2$, PO(OR')$_2$, C(O)C(O)R', or C(O)CH$_2$C(O)R', or R$^3$ and R$^4$ are taken together to form an optionally substituted saturated, partially unsaturated, or fully unsaturated 3-8 membered ring having 0-3 heteroatoms independently selected from nitrogen, oxygen, or sulfur.

In preferred embodiments $R^3$ and $R^4$ are each independently $Z-R^7$ wherein Z is an optionally substituted $C_{0-4}$ alkylidene chain wherein one methylene unit of Z is optionally replaced by O, NR, NRCO, $NRCO_2$, $NRSO_2$, CONR, C(O), C(O)O, and wherein $R^7$ is selected from halogen, CN, $N(R')_2$, NHCOR', or R', or wherein $R^3$ and $R^4$, taken together form an optionally substituted saturated, partially unsaturated, or fully unsaturated 5- or 6-membered ring having 0-3 heteroatoms independently selected from nitrogen, oxygen, or sulfur.

In other preferred embodiments, $R^3$ and $R^4$ are each independently hydrogen, CN, halogen, OH, SH, $NH_2$, $CO_2H$, COH, $CONH_2$, $SO_2NH_2$, $NO_2$, $(CH_2)_nNRR^7$, wherein R and $R^7$, taken together with the nitrogen atom to which they are bound form an optionally substituted 3-8-membered saturated or partially unsaturated ring having 1-3 heteroatoms selected from nitrogen, oxygen, or sulfur, or $R^3$ and $R^4$, taken together with the atoms to which they are bound, form an optionally substituted saturated, partially unsaturated, or fully unsaturated 5- or 6-membered ring having 0-3 heteroatoms independently selected from nitrogen, oxygen, or sulfur, and n is 0, 1, 2, 3, 4, or 5.

In still other preferred embodiments, one of $R^3$ or $R^4$ is hydrogen, and the other of $R^3$ or $R^4$ is $(CH_2)_n$halogen, $(CH_2)_nCN$, $(CH_2)_nOR^7$, $(CH_2)_nNRR^7$, $(CH_2)_nC(O)R^7$, $(CH_2)_nC(O)R^7$ $(CH_2)_nCH_3$, $(CH_2)_nC(O)NRR^7$, $(CH_2)_nSR^7$, wherein $R^7$ is hydrogen, $(CH_2)_mN(R')_2$, $C_1$-$C_4$alkyl, an optionally substituted 5- or 6-membered aryl, aralkyl, heteroaryl, or heteroaralkyl group, or R and $R^7$, taken together with the nitrogen atom to which they are bound form an optionally substituted 3-8-membered saturated or partially unsaturated ring having 1-3 heteroatoms selected from nitrogen, oxygen, or sulfur. In some embodiments, for compounds described directly above, $R^3$ is hydrogen. In other embodiments, for compounds described directly above, $R^4$ is hydrogen.

In yet other preferred embodiments, $R^3$ or $R^4$ are each independently hydrogen, $(CH_2)_nOR^7$, $(CH_2)_nNRR^7$, $(CH_2)_nCH_3$, $(CH_2)_nSR^7$, $(CH_2)_nC(O)R^7$, or $(CH_2)_nC(O)R^7$, wherein $R^7$ is $(CH_2)_mN(R')_2$, $C_1$-$C_4$alkyl, an optionally substituted 5- or 6-membered aryl, aralkyl, heteroaryl, or heteroaralkyl group, or R and $R^7$, taken together with the nitrogen atom to which they are bound form an optionally substituted 3-8-membered saturated or partially unsaturated ring having 1-3 heteroatoms selected from nitrogen, oxygen, or sulfur, wherein n is 0 or 1 and m is 0 or 1, or $R^3$ and $R^4$, taken together with the atoms to which they are bound, form an optionally substituted saturated, partially unsaturated, or fully unsaturated 5- or 6-membered ring having 0-3 heteroatoms independently selected from nitrogen, oxygen, or sulfur. In some preferred embodiments, $R^3$ is hydrogen, and $R^4$ is $(CH_2)_nOR^7$, $(CH_2)_nNRR^7$, $(CH_2)_nCH_3$, $(CH_2)_nSR^7$ $(CH_2)_nC(O)R^7$, or $(CH_2)_nC(O)R^7$, wherein $R^7$ is $(CH_2)_mN(R')_2$, $C_1$-$C_4$alkyl, an optionally substituted 5- or 6-membered aryl, aralkyl, heteroaryl, or heteroaralkyl group, or R and $R^7$, taken together with the nitrogen atom to which they are bound form an optionally substituted 3-8-membered saturated or partially unsaturated ring having 1-3 heteroatoms selected from nitrogen, oxygen, or sulfur, n is 0 or 1 and m is 0 or 1. In other preferred embodiments, $R^4$ is hydrogen and $R^3$ is $(CH_2)_nOR^7$, $(CH_2)_nNRR^7$, $(CH_2)_nCH_3$, $(CH_2)_nSR^7$, $(CH_2)_nC(O)R^7$, or $(CH_2)_nC(O)R^7$, $R^7$ is $(CH_2)_mN(R')_2$, $C_1$-$C_4$alkyl, an optionally substituted 5- or 6-membered aryl, aralkyl, heteroaryl, or heteroaralkyl group, or R and $R^7$, taken together with the nitrogen atom to which they are bound form an optionally substituted 3-8-membered saturated or partially unsaturated ring having 1-3 heteroatoms selected from nitrogen, oxygen, or sulfur, wherein n is 0 or 1 and m is 0 or 1. In still other preferred embodiments, $R^3$ and $R^4$, taken together with the atoms to which they are bound, form an optionally substituted saturated, partially unsaturated, or fully unsaturated 5- or 6-membered ring having 0-3 heteroatoms independently selected from nitrogen, oxygen, or sulfur, and wherein said ring is optionally substituted with 0, 1, 2, 3, 4, or 5 occurrences of Y—$R^8$. In preferred embodiments, each occurrence of Y—$R^8$ is independently methyl, ethyl, t-butyl, fluoro, chloro, bromo, oxo, $CF_3$, OMe, OEt, CN, $SO_2Me$, $SO_2NH_2$, $NH_2$, NHMe, $N(Me)_2$, SMe, SEt, OH, C(O)Me, $NO_2$, or $CH_2OH$.

The present invention additionally provides compounds wherein at least one of $R^3$ or $R^4$ is methyl and compounds have one of formulas I-A-i or I-A-ii:

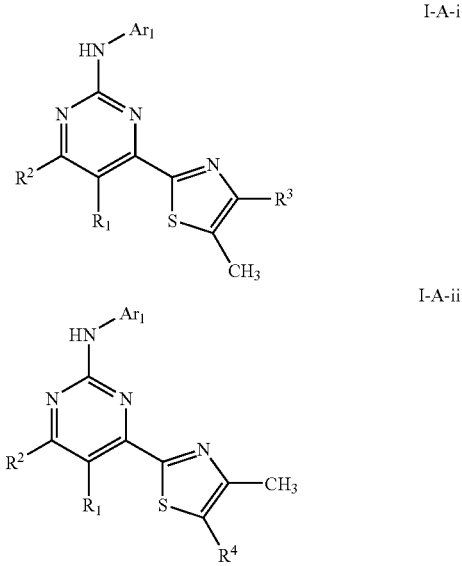

In other preferred embodiments at least one of $R^3$ or $R^4$ is $(CH_2)_nNRR^7$ and compounds have one of formulas I-B-i or I-B-ii:

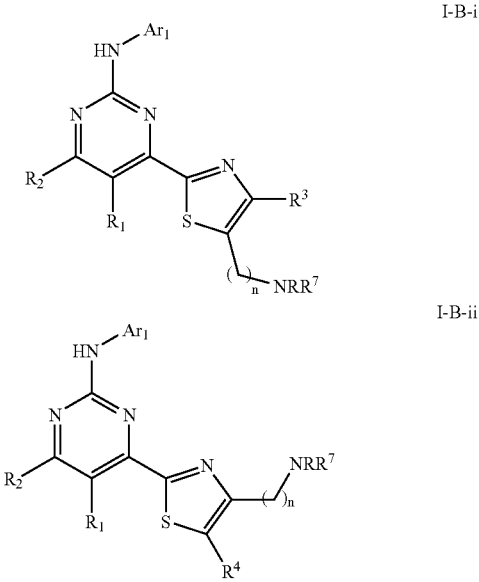

In other preferred embodiments at least one of $R^3$ or $R^4$ is $(CH_2)_nOR^7$ and compounds have one of formulas I-C-i or I-C-ii:

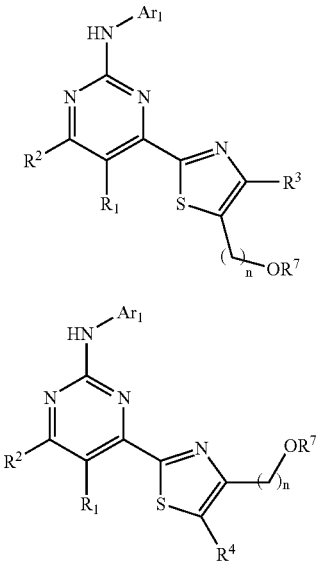

In yet other preferred embodiments both $R^3$ and $R^4$ are methyl and compounds have formula I-D-i, or $R^3$ and $R^4$, taken together, form an optionally substituted phenyl ring and compounds have formula I-E-i:

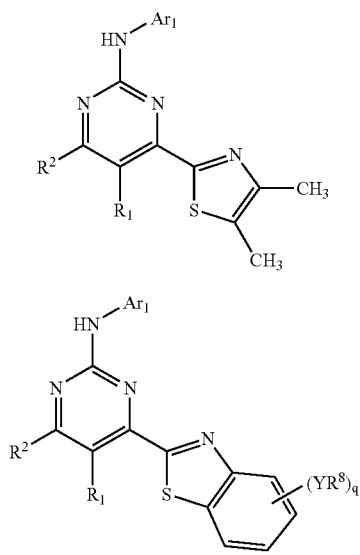

wherein q is 0-5.

In general, for compounds of formulas I-A-i, I-A-ii, I-B-i, I-B-ii, I-C-i, I-C-ii, I-D-i, and I-E-i, $Ar^1$ is an optionally substituted ring selected from: an aryl group selected from a 5-6 membered monocyclic or an 8-10 membered bicyclic ring having 0-5 heteroatoms independently selected from nitrogen, oxygen, or sulfur; a 3-8-membered saturated or partially unsaturated monocyclic ring having 0-3 heteroatoms independently selected from nitrogen, oxygen, or sulfur; or an 8-10-membered saturated or partially unsaturated bicyclic ring system having 0-5 heteroatoms independently selected from nitrogen, oxygen, or sulfur, wherein $Ar^1$ is optionally substituted at one or more carbon atoms with 0-5 occurrences of $-Z-R^5$, and at one or more substitutable nitrogen atoms with $-R^6$.

Preferred $Ar^1$ groups for compounds of formulas I-A-i, I-A-ii, I-B-i, I-B-ii, I-C-i, I-C-ii, I-D-i, and I-E-i are optionally substituted rings selected from:

(a) a phenyl, indanyl, or naphthyl ring;
(b) a 5-6 membered heterocyclic ring having 1-3 heteroatoms independently selected from nitrogen, oxygen, or sulfur; or
(c) a 5-6 membered monocyclic or 9-10 membered bicyclic heteroaryl ring having 1-3 heteroatoms independently selected from oxygen, nitrogen, or sulfur.

More preferred $Ar^1$ groups for compounds of formulas I-A-i, I-A-ii, I-B-i, I-B-ii, I-C-i, I-C-ii, I-D-i, and I-E-i are optionally substituted rings selected from:

(a) a phenyl ring;
(b) a 5-6 membered heterocyclic ring having 1-3 heteroatoms independently selected from nitrogen, oxygen, or sulfur; or
(c) a 5-6 membered monocyclic heteroaryl ring having 1-3 heteroatoms independently selected from oxygen, nitrogen, or sulfur.

In still other embodiments, preferred $Ar^1$ groups for compounds of formulas I-A-i, I-A-ii, I-B-i, I-B-ii, I-C-i, I-C-ii, I-D-i, and I-E-i are optionally substituted rings selected from any one of a-bb:

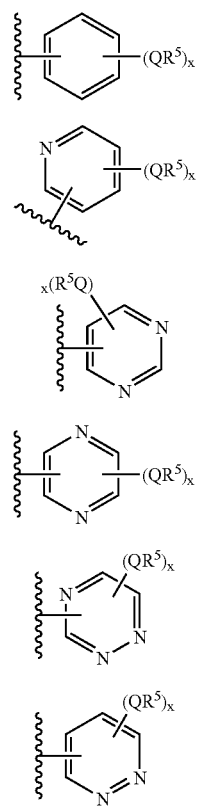

-continued
g
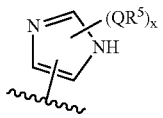
h
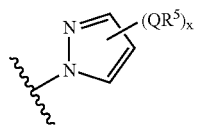
i
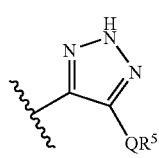
j
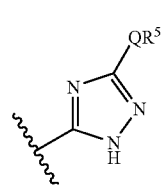
k
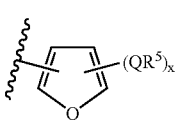
l
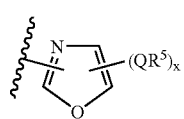
m
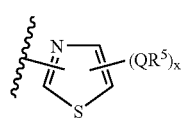
n
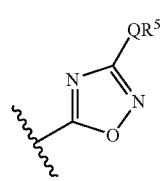
o
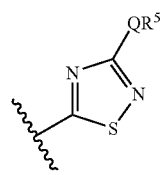
-continued
p
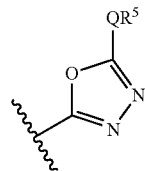
q
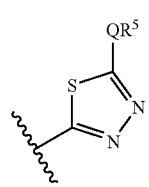
r
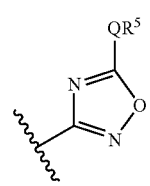
s
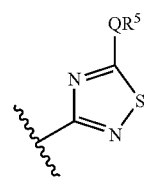
t
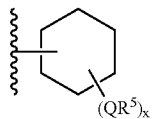
u
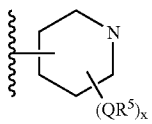
v
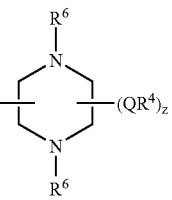
w
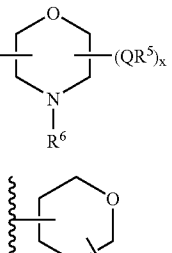
x
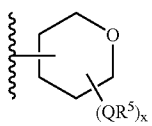

-continued y
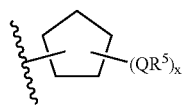

z
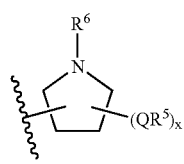

aa
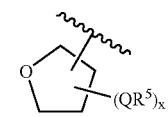

bb
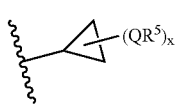

wherein Q and $R^5$ are as defined generally above and in subsets herein, and x is 0-5.

Preferred $Ar^1$ rings for compounds of formulas I-A-i, I-A-ii, I-B-i, I-B-ii, I-C-i, I-C-ii, I-D-i, and I-E-i are phenyl, pyrimidinyl, or pyridyl.

In still other embodiments, for compounds of formulas I-A-i, I-A-ii, I-B-i, I-B-ii, I-C-i, I-C-ii, I-D-i, and I-E-i, $Ar^1$ is not 3,4,5-trimethoxyphenyl.

In preferred embodiments, for compounds of formulas I-A-i, I-A-ii, I-B-i, I-B-ii, I-C-i, I-C-ii, I-D-i, and I-E-i, $Ar^1$ is optionally substituted phenyl and compounds have one of formulas II-A-i, II-A-ii, II-B-i, II-B-ii, II-C-i, II-C-ii, II-D-i, and II-E-i:

II-A-i

II-A-ii

-continued

II-B-i
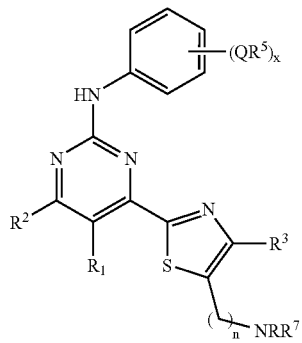

II-B-ii
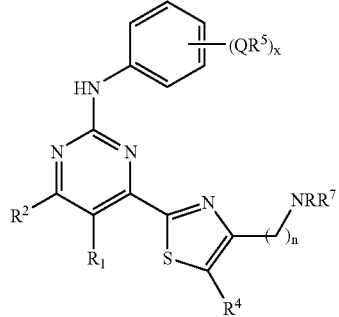

II-C-i
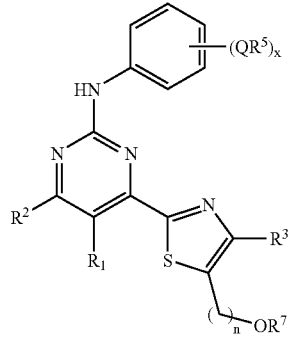

II-C-ii
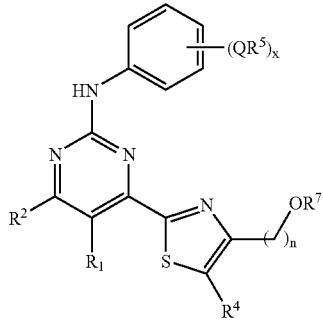

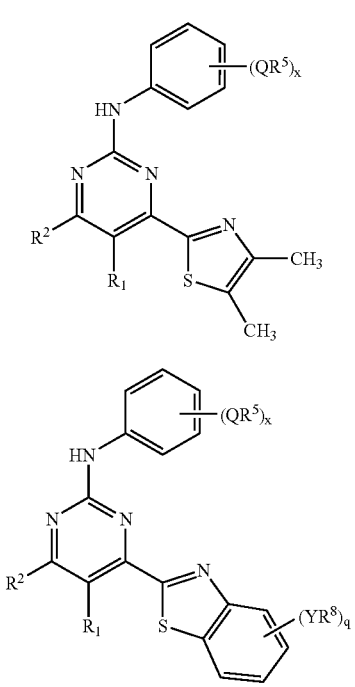

where x and q are each independently 0-5.

As described generally above, $Ar^1$ is optionally substituted with up to 5 independent occurrences of $Q-R^5$, wherein each occurrence of Q is independently a bond or is an optionally substituted $C_1-C_6$ alkylidene chain wherein up to two non-adjacent methylene units of Q are optionally replaced by CO, $CO_2$, COCO, CONR, OCONR, NRNR, NRNRCO, NRCO, $NRCO_2$, NRCONR, SO, $SO_2$, $NRSO_2$, $SO_2NR$, $NRSO_2NR$, O, S, or NR; and each occurrence of $R^5$ is independently selected from R', halogen, $NO_2$, CN, OR', SR', $N(R')_2$, NR'C(O)R', $NR'C(O)N(R')_2$, $NR'CO_2R'$, C(O)R', $CO_2R'$, OC(O)R', $C(O)N(R')_2$, $OC(O)N(R')_2$, SOR', $SO_2R'$, $SO_2N(R')_2$, $NR'SO_2R'$, $NR'SO_2N(R')_2$, $PO(OR')_2$, C(O)C(O)R', or $C(O)CH_2C(O)R'$. In preferred embodiments, x is 0, 1, 2, or 3. In other preferred embodiments, x is 1, 2, or 3.

In preferred embodients, for compounds of formulas I-A-i, I-A-ii, I-B-i, I-B-ii, I-C-i, I-C-ii, I-D-i, I-E-i, II-A-i, II-A-ii, II-B-i, II-B-ii, II-C-i, II-C-ii, II-D-i, and II-E-i, Q is independently a bond or is an optionally substituted $C_1-C_4$ alkylidene chain wherein up to two non-adjacent methylene units of Q are optionally replaced by CO, $CO_2$, CONR, OCONR, NRCO, $NRCO_2$, $NRSO_2$, $SO_2NR$, O, S, or NR; and each occurrence of $R^5$ is independently selected from R', halogen, $NO_2$, CN, OR', SR', $N(R')_2$, NR'C(O)R', $NR'C(O)N(R')_2$, $NR'CO_2R'$, C(O)R', $CO_2R'$, OC(O)R', $C(O)N(R')_2$, $OC(O)N(R')_2$, SOR', $SO_2R'$, $SO_2N(R')_2$, $NR'SO_2R'$, $NR'SO_2N(R')_2$, $PO(OR')_2$, C(O)C(O)R', or $C(O)CH_2C(O)$ R', and x is 0, 1, 2, or 3. In preferred embodiments, x is 1, 2, or 3.

Preferred $Q-R^5$ substituents on $Ar^1$ for compounds of formulas I-A-i, I-A-ii, I-B-i, I-B-ii, I-C-i, I-C-ii, I-D-i, I-E-i, II-A-i, II-A-ii, II-B-i, II-B-ii, II-C-i, II-C-ii, II-D-i, and II-E-i are $CH_2$halogen, halogen, $CH_2CN$, CN, $CH_2CO_2R'$, $CO_2R'$, $CH_2COR'$, COR', R', $CH_2NO_2$, $NO_2$, $CH_2OR'$, OR', $CH_2SR'$, SR', haloalkyl, $CH_2SO_2N(R')_2$, $SO_2N(R')_2$, $CH_2N(R')_2$, $N(R')_2$, NHCOR', $CH_2NHCOR'$, $CH_2PO(OR')_2$, $PO(OR')_2$, or two adjacent occurrences of $Q-R^5$, taken together with the atoms to which they are bound, form an optionally substituted saturated, partially unsaturated, or fully unsaturated 5-8-membered ring having 0-3 heteroatoms selected from nitrogen, oxygen, or sulfur.

More preferred $Q-R^5$ substituents on $Ar^1$ for compounds of formulas I-A-i, I-A-ii, I-B-i, I-B-ii, I-C-i, I-C-ii, I-D-i, I-E-i, II-A-i, II-A-ii, II-B-i, II-B-ii, II-C-i, II-C-ii, II-D-i, and II-E-i are fluoro, iodo, chloro, bromo, $COCH_3$, $CO_2CH_3$, $C_{1-4}$alkyl (for example, methyl, ethyl, propyl, cyclopropyl, n-butyl, cyclobuyl, or t-butyl), $NH_2$, $CH_2NH_2$, NHMe, $CH_2NHMe$, $N(Me)_2$, $CH_2N(Me)_2$, $N(Et)_2$, $CH_2N(Et)_2$, NH(phenyl), $CO(C_{1-4}alkyl)$, $CH_2CO(C_{1-4}alkyl)$, NHCO ($C_{1-4}$ alkyl), $CH_2NHCO(C_{1-4}alkyl)$, CN, $CH_2CN$, OH, $C_{1-4}$alkoxy (for example, $OCH_3$, $OCH_2CH_3$, $O(CH_2)_2CH_3$, or $O(CH_2)_3CH_3$), optionally substituted benzyloxy, optionally substituted phenyloxy, $CF_3$, $SO_2NH_2$, $SO_2NHMe$, optionally substituted $SO_2(phenyl)$, $SO_2(C_{1-4}alkyl)$, $CONH_2$, $CH_2PO(OR')_2$, or an optionally substituted group selected from a saturated, partially unsaturated, or fully unsaturated 5- or 6-membered ring having 0-3 heteroatoms independently selected from nitrogen, oxygen, or sulfur. Other preferred $Ar^1$ substituents are those substituents where two adjacent occurrences of $Q-R^5$, taken together with the atoms to which they are bound, and include a fused optionally substituted saturated, partially unsaturated, or fully unsaturated 5- or 6-membered ring having 0-3 heteroatoms selected from nitrogen, oxygen, or sulfur. In more preferred embodiments, these fused substituents formed by two adjacent occurrences of $Q-R^5$ include an optionally substituted group selected from methylenedioxy, ethylenedioxy, propylenedioxy, thiazolyl, oxazolyl, pyrrolyl, pyrazolyl, imidazolyl, phenyl, pyridyl, pyrimidinyl, furyl, thiophene, pyran, pyrrolidinyl, piperidinyl, piperazinyl, or morpholinyl.

In yet other embodiments, $Ar^1$ is phenyl and is substituted with two occurrences (x=2) of $Q-R^5$ and $Ar^1$ is:

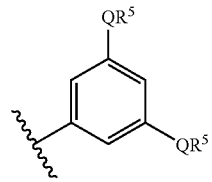

wherein each occurrence of $QR^5$ is independently $CH_2$halogen, halogen, $CH_2CN$, CN, $CH_2CO_2R'$, $CO_2R'$, $CH_2COR'$, COR', R', $CH_2NO_2$, $NO_2$, $CH_2OR'$, OR', $CH_2SR'$, SR', haloalkyl, $CH_2SO_2N(R')_2$, $SO_2N(R')_2$, $CH_2N(R')_2$, $N(R')_2$, NHCOR', $CH_2NHCOR'$, $CH_2PO(OR')_2$, $PO(OR')_2$, In certain preferred embodiments, each occurrence of $QR^5$ is independently fluoro, iodo, chloro, bromo, $COCH_3$, $CO_2CH_3$, $C_{1-4}$alkyl (for example, methyl, ethyl, propyl, cyclopropyl, n-butyl, cyclobuyl, or t-butyl), $NH_2$, $CH_2NH_2$, NHMe, $CH_2NHMe$, $N(Me)_2$, $CH_2N(Me)_2$, $N(Et)_2$, $CH_2N(Et)_2$, NH(phenyl), $CO(C_{1-4}alkyl)$, $CH_2CO$ $(C_{1-4}alkyl)$, $NHCO(C_{1-4}alkyl)$, $CH_2NHCO(C_{1-4}alkyl)$, CN, $CH_2CN$, OH, $C_{1-4}$alkoxy (for example, $OCH_3$, $OCH_2CH_3$, $O(CH_2)_2CH_3$, or $O(CH_2)_3CH_3$), optionally substituted benzyloxy, optionally substituted phenyloxy, $CF_3$, $SO_2NH_2$, $SO_2NHMe$, optionally substituted $SO_2(phenyl)$, $SO_2(C_{1-4}$ alkyl), $CONH_2$, $CH_2PO(OR')_2$, or an optionally substituted group selected from a saturated, partially unsaturated, or fully unsaturated 5- or 6-membered ring having 0-3 heteroatoms independently selected from nitrogen, oxygen, or sulfur. In still other preferred embodiments, both occurrences of $QR^5$ are methyl. In yet other preferred embodiments, at least one occurrence of $QR^5$ is $CF_3$.

In yet other embodiments, $Ar^1$ is phenyl and is substituted with three occurrences (x=3) of Q-$R^5$ and $Ar^1$ is:

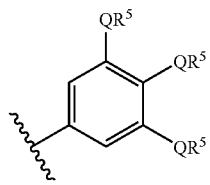

wherein each occurrence of $QR^5$ is independently $CH_2$halogen, halogen, $CH_2CN$, CN, $CH_2CO_2R'$, $CO_2R'$, $CH_2COR'$, $COR'$, $R'$, $CH_2NO_2$, $NO_2$, $CH_2OR'$, $OR'$, $CH_2SR'$, $SR'$, haloalkyl, $CH_2SO_2N(R')_2$, $SO_2N(R')_2$, $CH_2N(R')_2$, $N(R')_2$, $NHCOR'$, $CH_2NHCOR'$, $CH_2PO(OR')_2$, $PO(OR')_2$. In certain preferred embodiments, each occurrence of $QR^5$ is independently fluoro, iodo, chloro, bromo, $COCH_3$, $CO_2CH_3$, $C_{1-4}$alkyl (for example, methyl, ethyl, propyl, cyclopropyl, n-butyl, cyclobuyl, or t-butyl), $NH_2$, $CH_2NH_2$, NHMe, $CH_2NHMe$, $N(Me)_2$, $CH_2N(Me)_2$, $N(Et)_2$, $CH_2N(Et)_2$, NH(phenyl), $CO(C_{1-4}alkyl)$, $CH_2CO(C_{1-4}alkyl)$, $NHCO(C_{1-4}alkyl)$, $CH_2NHCO(C_{1-4}alkyl)$, CN, $CH_2CN$, OH, $C_{1-4}$alkoxy (for example, $OCH_3$, $OCH_2CH_3$, $O(CH_2)_2CH_3$, or $O(CH_2)_3CH_3$), optionally substituted benzyloxy, optionally substituted phenyloxy, $CF_3$, $SO_2NH_2$, $SO_2NHMe$, optionally substituted $SO_2(phenyl)$, $SO_2(C_{1-4}alkyl)$, $CONH_2$, $CH_2PO(OR')_2$, or an optionally substituted group selected from a saturated, partially unsaturated, or fully unsaturated 5- or 6-membered ring having 0-3 heteroatoms independently selected from nitrogen, oxygen, or sulfur. In still other preferred embodiments, each occurrence of $QR^5$ is independently fluoro, iodo, chloro, bromo, $COCH_3$, $CO_2CH_3$, $C_{1-4}$alkyl (for example, methyl, ethyl, propyl, cyclopropyl, n-butyl, cyclobuyl, or t-butyl), $NH_2$, $CH_2NH_2$, NHMe, $CH_2NHMe$, $N(Me)_2$, $CH_2N(Me)_2$, $N(Et)_2$, $CH_2N(Et)_2$, NH(phenyl), $CO(C_{1-4}alkyl)$, $CH_2CO(C_{1-4}alkyl)$, $NHCO(C_{1-4}alkyl)$, $CH_2NHCO(C_{1-4}alkyl)$, CN, $CH_2CN$, OH, optionally substituted benzyloxy, optionally substituted phenyloxy, $CF_3$, $SO_2NH_2$, $SO_2NHMe$, optionally substituted $SO_2(phenyl)$, $SO_2(C_{1-4}alkyl)$, $CONH_2$, $CH_2PO(OR')_2$, or an optionally substituted group selected from a saturated, partially unsaturated, or fully unsaturated 5- or 6-membered ring having 0-3 heteroatoms independently selected from nitrogen, oxygen, or sulfur.

Each of the Q-$R^5$ substituents described above are also optionally further substituted with one or more groups independently selected from R, OR, $N(R')_2$, $SO_2R$, halogen, $NO_2$, CN, SR, $SO_2N(R')_2$, $CO_2R$, C(O)R, or oxo. In more preferred embodiments, each of the Q-$R^5$ groups described above are also optionally further substituted with one or two groups independently selected from methyl, ethyl, t-butyl, fluoro, chloro, bromo, oxo, $CF_3$, OMe, OEt, CN, $SO_2Me$, $SO_2NH_2$, $NH_2$, NHMe, $N(Me)_2$, SMe, SEt, OH, C(O)Me, $NO_2$, or $CH_2OH$.

Preferred $R^1$ and $R^2$ groups for compounds of formulas I-A-i, I-A-ii, I-B-i, I-B-ii, I-C-i, I-C-ii, I-D-i, I-E-ii, II-A-i, II-A-ii, II-B-i, II-B-ii, II-C-i, II-C-ii, II-D-i, and II-E-i are selected from hydrogen, $N(R')_2$, SR, OR, or TR, or $R^1$ and $R^2$, taken together form an optionally substituted saturated, partially unsaturated, or fully unsaturated 5-membered ring having 0-2 heteroatoms independently selected from N, O, or S. More preferred $R^1$ and $R^2$ groups are hydrogen, OH, $CH_3$, $CH_2CH_3$, $OCH_3$, $CH_2OH$, $CH_2OCH_3$, $CH_2NH_2$, $CH_2NHCH_3$, $NH_2$, or $CH_2NH_2$, or $R^1$ and $R^2$, taken together, form a fused optionally substituted pyrrolyl, pyrazolyl, or imidazolyl ring. Still other preferred groups include hydrogen, $NH_2$, or $CH_2NH_2$.

Preferred $R^3$ groups of for compounds of formulas I-A-i and II-A-i are those wherein Z is a bond or is an optionally substituted $C_{0-4}$ alkylidene chain wherein one methylene unit of Z is optionally replaced by O, NR, NRCO, $NRCO_2$, $NRSO_2$, CONR, C(O), C(O)O, and wherein $R^7$ is selected from halogen, CN, $N(R')_2$, $NHCOR'$, or $R'$. In more preferred embodiments, $R^3$ is $(CH_2)_n$halogen, $(CH_2)_nCN$, $(CH_2)_nOR^7$, $(CH_2)_nNRR^7$, $(CH_2)_nC(O)R^7$, $(CH_2)_nC(O)R^7$ $(CH_2)_nCH_3$, $(CH_2)_nC(O)NRR^7$, $(CH_2)_nSR^7$, wherein $R^7$ is $(CH_2)_mN(R')_2$, $C_1$-$C_4$alkyl, an optionally substituted 5- or 6-membered aryl, aralkyl, heteroaryl, or heteroaralkyl group, or R and $R^7$, taken together with the nitrogen atom to which they are bound form an optionally substituted 3-8-membered saturated or partially unsaturated ring having 1-3 heteroatoms selected from nitrogen, oxygen, or sulfur, n is 0 or 1, and m is 0 or 1. In most preferred embodiments, $R^3$ is hydrogen or methyl.

Preferred $R^4$ groups of for compounds of formulas I-A-ii and II-A-ii are those wherein Z is a bond or is an optionally substituted $C_{0-4}$ alkylidene chain wherein one methylene unit of Z is optionally replaced by O, NR, NRCO, $NRCO_2$, $NRSO_2$, CONR, C(O), C(O)O, and wherein $R^7$ is selected from halogen, CN, $N(R')_2$, $NHCOR'$, or $R'$. In more preferred embodiments, $R^4$ is $(CH_2)_n$halogen, $(CH_2)_nCN$, $(CH_2)_nOR^7$, $(CH_2)_nNRR^7$, $(CH_2)_nC(O)R^7$, $(CH_2)_nC(O)R^7$ $(CH_2)_nCH_3$, $(CH_2)_nC(O)NRR^7$, $(CH_2)_nSR^7$, wherein $R^7$ is $(CH_2)_mN(R')_2$, $C_1$-$C_4$alkyl, an optionally substituted 5- or 6-membered aryl, aralkyl, heteroaryl, or heteroaralkyl group, or R and $R^7$, taken together with the nitrogen atom to which they are bound form an optionally substituted 3-8-membered saturated or partially unsaturated ring having 1-3 heteroatoms selected from nitrogen, oxygen, or sulfur, n is 0 or 1, and m is 0 or 1. In still other preferred embodiments, $R^4$ is hydrogen or methyl.

Preferred $R^3$ groups of for compounds of formulas I-B-i and II-B-i are those wherein Z is a bond or is an optionally substituted $C_{0-4}$ alkylidene chain wherein one methylene unit of Z is optionally replaced by O, NR, NRCO, $NRCO_2$, $NRSO_2$, CONR, C(O), C(O)O, and wherein $R^7$ is selected from halogen, CN, $N(R')_2$, $NHCOR'$, or $R'$. In more preferred embodiments, $R^3$ is $(CH_2)_n$halogen, $(CH_2)_nCN$, $(CH_2)_nOR^7$, $(CH_2)_nNRR^7$, $(CH_2)_nC(O)R^7$, $(CH_2)_nC(O)R^7$ $(CH_2)_nCH_3$, $(CH_2)_nC(O)NRR^7$, $(CH_2)_nSR^7$, wherein $R^7$ is $(CH_2)_mN(R')_2$, $C_1$-$C_4$alkyl, an optionally substituted 5- or 6-membered aryl, aralkyl, heteroaryl, or heteroaralkyl group, or R and $R^7$, taken together with the nitrogen atom to which they are bound form an optionally substituted 3-8-membered saturated or partially unsaturated ring having 1-3 heteroatoms selected from nitrogen, oxygen, or sulfur, n is 0 or 1, and m is 0 or 1. In most preferred embodiments, $R^3$ is hydrogen or methyl.

Preferred $R^4$ groups of for compounds of formulas I-B-ii and II-B-ii are those wherein Z is a bond or is an optionally substituted $C_{0-4}$ alkylidene chain wherein one methylene unit of Z is optionally replaced by O, NR, NRCO, $NRCO_2$, $NRSO_2$, CONR, C(O), C(O)O, and wherein $R^7$ is selected from halogen, CN, $N(R')_2$, $NHCOR'$, or $R'$. In more preferred embodiments, $R^4$ is $(CH_2)_n$halogen, $(CH_2)_nCN$, $(CH_2)_nOR^7$, $(CH_2)_nNRR^7$, $(CH_2)_nC(O)R^7$, $(CH_2)_nC(O)R^7$ $(CH_2)_nCH_3$, $(CH_2)_nC(O)NRR^7$, $(CH_2)_nSR^7$, wherein $R^7$ is $(CH_2)_mN(R')_2$, $C_1$-$C_4$alkyl, an optionally substituted 5- or 6-membered aryl, aralkyl, heteroaryl, or heteroaralkyl group, or R and $R^7$, taken together with the nitrogen atom to which they are bound form an optionally substituted 3-8-membered saturated or partially unsaturated ring having 1-3 heteroatoms selected from nitrogen, oxygen, or sulfur, n is 0 or 1, and m is 0 or 1. In still other preferred embodiments, $R^4$ is hydrogen or methyl.

Preferred $R^3$ groups of for compounds of formulas I-C-i and II-C-i are those wherein Z is a bond or is an optionally substituted $C_{0-4}$ alkylidene chain wherein one methylene unit of Z is optionally replaced by O, NR, NRCO, $NRCO_2$, $NRSO_2$, CONR, C(O), C(O)O, and wherein $R^7$ is selected from halogen, CN, $N(R')_2$, NHCOR', or R'. In more preferred embodiments, $R^3$ is $(CH_2)_n$halogen, $(CH_2)_n$CN, $(CH_2)_nOR^7$, $(CH_2)_nNRR^7$, $(CH_2)_nC(O)R^7$, $(CH_2)_nC(O)R^7$ $(CH_2)_nCH_3$, $(CH_2)_nC(O)NRR^7$, $(CH_2)_nSR^7$, wherein $R^7$ is $(CH_2)_mN(R')_2$, $C_1$-$C_4$alkyl, an optionally substituted 5- or 6-membered aryl, aralkyl, heteroaryl, or heteroaralkyl group, or R and $R^7$, taken together with the nitrogen atom to which they are bound form an optionally substituted 3-8-membered saturated or partially unsaturated ring having 1-3 heteroatoms selected from nitrogen, oxygen, or sulfur, n is 0 or 1, and m is 0 or 1. In most preferred embodiments, $R^3$ is hydrogen or methyl.

Preferred $R^4$ groups of for compounds of formulas I-C-ii and II-C-ii are those wherein Z is a bond or is an optionally substituted $C_{0-4}$ alkylidene chain wherein one methylene unit of Z is optionally replaced by O, NR, NRCO, $NRCO_2$, $NRSO_2$, CONR, C(O), C(O)O, and wherein $R^7$ is selected from halogen, CN, $N(R')_2$, NHCOR', or R'. In more preferred embodiments, $R^4$ is $(CH_2)_n$halogen, $(CH_2)_n$CN, $(CH_2)_nOR^7$, $(CH_2)_nNRR^7$, $(CH_2)_nC(O)R^7$, $(CH_2)_nC(O)R^7$ $(CH_2)_nCH_3$, $(CH_2)_nC(O)NRR^7$, $(CH_2)_nSR^7$, wherein $R^7$ is $(CH_2)_mN(R')_2$, $C_1$-$C_4$alkyl, an optionally substituted 5- or 6-membered aryl, aralkyl, heteroaryl, or heteroaralkyl group, or R and $R^7$, taken together with the nitrogen atom to which they are bound form an optionally substituted 3-8-membered saturated or partially unsaturated ring having 1-3 heteroatoms selected from nitrogen, oxygen, or sulfur, n is 0 or 1, and m is 0 or 1. In still other preferred embodiments, $R^4$ is hydrogen or methyl.

In still other preferred embodiments, for each of the embodiments described directly above n is 0. In yet other preferred embodiments, for each of the embodiments described directly above n is 1.

In still other preferred embodiments, for compounds of formulas I-E-i and II-E-i, where $R^3$ and $R^4$, taken together with the atoms to which they are bound, form an optionally substituted phenyl ring optionally substituted with 0, 1, 2, 3, 4, or 5 occurrences of Y—$R^8$, each occurrence of Y—$R^8$ is independently methyl, ethyl, t-butyl, fluoro, chloro, bromo, oxo, $CF_3$, OMe, OEt, CN, $SO_2Me$, $SO_2NH_2$, $NH_2$, NHMe, $N(Me)_2$, SMe, SEt, OH, C(O)Me, $NO_2$, or $CH_2OH$. In preferred embodiments, q is 0, 1, or 2.

In yet other preferred embodiments compounds have one of formulas II-A-i, II-B-i, or II-C-i, wherein the compound variables are defined as:

a) x is 0, 1, 2, or 3 and Q-$R^5$ is $CH_2$halogen, halogen, $CH_2$CN, CN, $CH_2CO_2R'$, $CO_2R'$, $CH_2$COR', COR', R', $CH_2NO_2$, $NO_2$, $CH_2OR'$, OR', $CH_2SR'$, SR', haloalkyl, $CH_2SO_2N(R')_2$, $SO_2N(R')_2$, $CH_2N(R')_2$, $N(R')_2$, NHCOR', $CH_2$NHCOR', $CH_2PO(OR')_2$, $PO(OR')_2$, or Q-$R^5$, taken together with the atoms to which they are bound, form an optionally substituted saturated, partially unsaturated, or fully unsaturated 5-8-membered ring having 0-3 heteroatoms selected from nitrogen, oxygen, or sulfur;

b) $R^1$ and $R^2$ are each independently hydrogen, $N(R')_2$, SR, OR, or TR, or $R^1$ and $R^2$, taken together form an optionally substituted saturated, partially unsaturated, or fully unsaturated 5-membered ring having 0-2 heteroatoms independently selected from N, O, or S; and c) $R^3$ is $(CH_2)_n$halogen, $(CH_2)_n$CN, $(CH_2)_nOR^7$, $(CH_2)_nNRR^7$, $(CH_2)_nC(O)R^7$, $(CH_2)_nC(O)R^7$ $(CH_2)_nCH_3$, $(CH_2)_nC(O)NRR^7$, $(CH_2)_nSR^7$, wherein $R^7$ is $(CH_2)_mN(R')_2$, $C_1$-$C_4$alkyl, an optionally substituted 5- or 6-membered aryl, aralkyl, heteroaryl, or heteroaralkyl group, or R and $R^7$, taken together with the nitrogen atom to which they are bound form an optionally substituted 3-8-membered saturated or partially unsaturated ring having 1-3 heteroatoms selected from nitrogen, oxygen, or sulfur, n is 0 or 1, and m is 0 or 1.

In yet other preferred embodiments compounds have one of formulas II-A-ii, II-B-ii, or II-C-ii, wherein one or more of the compound variables are defined as:

a) x is 0, 1, 2, or 3, and Q-$R^5$ is $CH_2$halogen, halogen, $CH_2$CN, CN, $CH_2CO_2R'$, $CO_2R'$, $CH_2$COR', COR', R', $CH_2NO_2$, $NO_2$, $CH_2OR'$, OR', $CH_2SR'$, SR', haloalkyl, $CH_2SO_2N(R')_2$, $SO_2N(R')_2$, $CH_2N(R')_2$, $N(R')_2$, NHCOR', $CH_2$NHCOR', $CH_2PO(OR')_2$, $PO(OR')_2$, or Q-$R^5$, taken together with the atoms to which they are bound, form an optionally substituted saturated, partially unsaturated, or fully unsaturated 5-8-membered ring having 0-3 heteroatoms selected from nitrogen, oxygen, or sulfur;

b) $R^1$ and $R^2$ are each independently hydrogen, $N(R')_2$, SR, OR, or TR, or $R^1$ and $R^2$ taken together form an optionally substituted saturated, partially unsaturated, or fully unsaturated 5-membered ring having 0-2 heteroatoms independently selected from N, O, or S; and c) $R^4$ is $(CH_2)_n$halogen, $(CH_2)_n$CN, $(CH_2)_nOR^7$, $(CH_2)_nNRR^7$, $(CH_2)_nC(O)R^7$, $(CH_2)_nC(O)R^7$ $(CH_2)_nCH_3$, $(CH_2)_nC(O)NRR^7$, $(CH_2)_nSR^7$, wherein $R^7$ is $(CH_2)_mN(R')_2$, $C_1$-$C_4$alkyl, an optionally substituted 5- or 6-membered aryl, aralkyl, heteroaryl, or heteroaralkyl group, or R and $R^7$, taken together with the nitrogen atom to which they are bound form an optionally substituted 3-8-membered saturated or partially unsaturated ring having 1-3 heteroatoms selected from nitrogen, oxygen, or sulfur, n is 0 or 1, and m is 0 or 1.

In yet other preferred embodiments compounds have formula II-E-i, wherein one or more of the compound variables are defined as:

a) x is 0, 1, 2, or 3, and Q-$R^5$ is $CH_2$halogen, halogen, $CH_2$CN, CN, $CH_2CO_2R'$, $CO_2R'$, $CH_2$COR', COR', R', $CH_2NO_2$, $NO_2$, $CH_2OR'$, OR', $CH_2SR'$, SR', haloalkyl, $CH_2SO_2N(R')_2$, $SO_2N(R')_2$, $CH_2N(R')_2$, $N(R')_2$, NHCOR', $CH_2$NHCOR', $CH_2PO(OR')_2$, $PO(OR')_2$, or Q-$R^5$, taken together with the atoms to which they are bound, form an optionally substituted saturated, partially unsaturated, or fully unsaturated 5-8-membered ring having 0-3 heteroatoms selected from nitrogen, oxygen, or sulfur;

b) $R^1$ and $R^2$ are each independently hydrogen, $N(R')_2$, SR, OR, or TR, or $R^1$ and $R^2$, taken together form an optionally substituted saturated, partially unsaturated, or fully unsaturated 5-membered ring having 0-2 heteroatoms independently selected from N, O, or S; and c) q is 0, 1, or 2, and each occurrence of Y—$R^8$ is independently methyl, ethyl, t-butyl, fluoro, chloro, bromo, oxo, $CF_3$, OMe, OEt, CN, $SO_2Me$, $SO_2NH_2$, $NH_2$, NHMe, $N(Me)_2$, SMe, SEt, OH, C(O)Me, $NO_2$, or $CH_2OH$.

Exemplary compounds of Formula I (and classes and subclasses thereof) are depicted in Table 1 below:
Table 1. Examples of Compounds of Formula I:
TABLE 1
Examples of Compounds of Formula I:
I-1
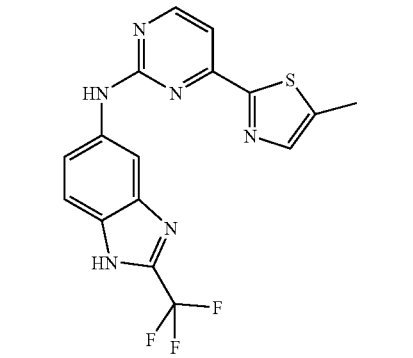
I-2
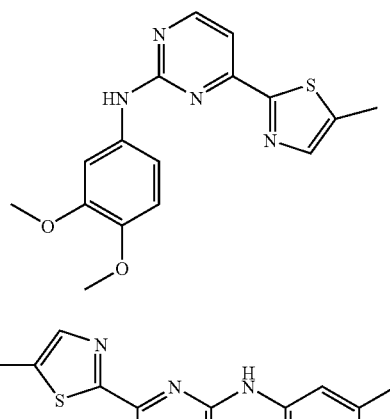
I-3
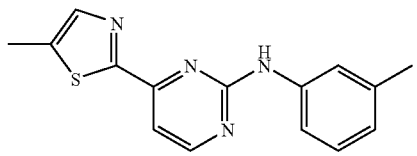
I-4
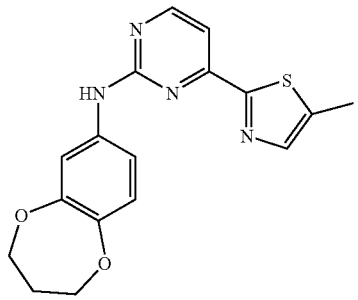
I-5
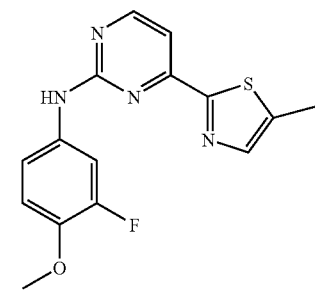
TABLE 1-continued
Examples of Compounds of Formula I:
I-6
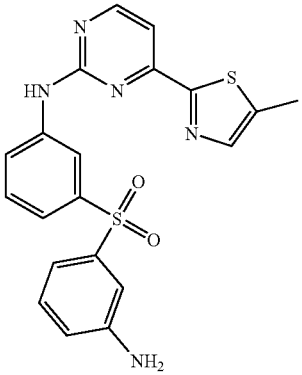
I-7
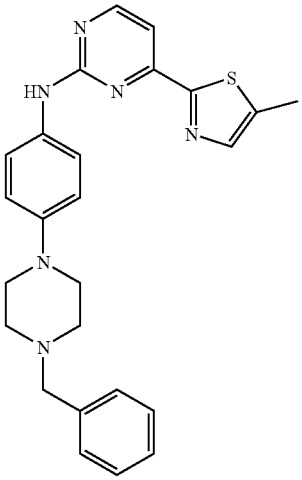
I-8
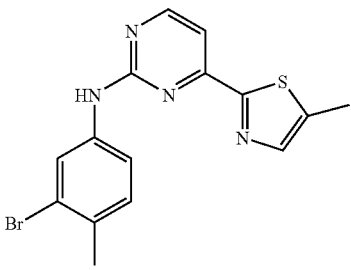
I-9
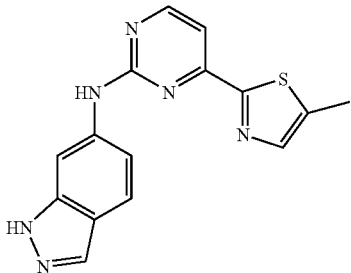

TABLE 1-continued

Examples of Compounds of Formula I:

I-10, I-11, I-12, I-13, I-14, I-15, I-16, I-17, I-18, I-9

TABLE 1-continued
Examples of Compounds of Formula I:
I-20
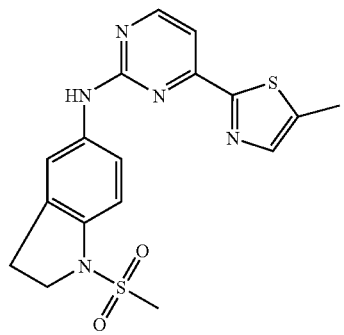
I-21
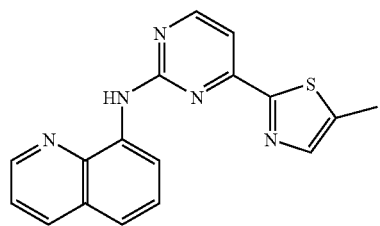
I-22
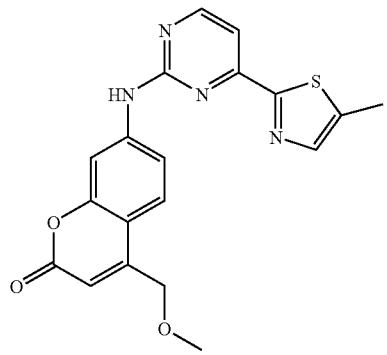
I-23
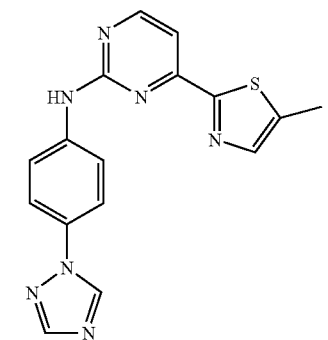
TABLE 1-continued
Examples of Compounds of Formula I:
I-24
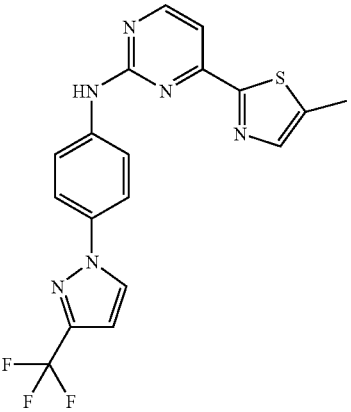
I-25
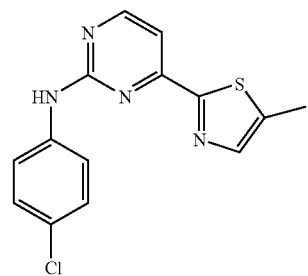
I-26
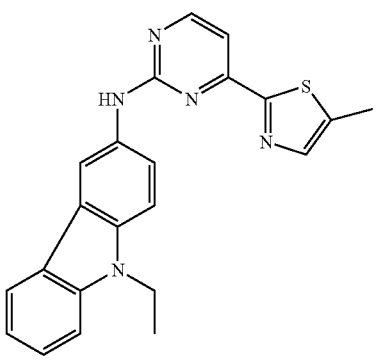
I-27
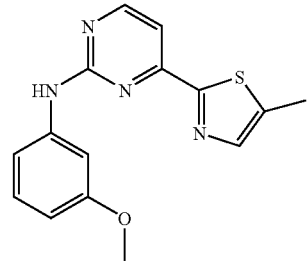

TABLE 1-continued
Examples of Compounds of Formula I:
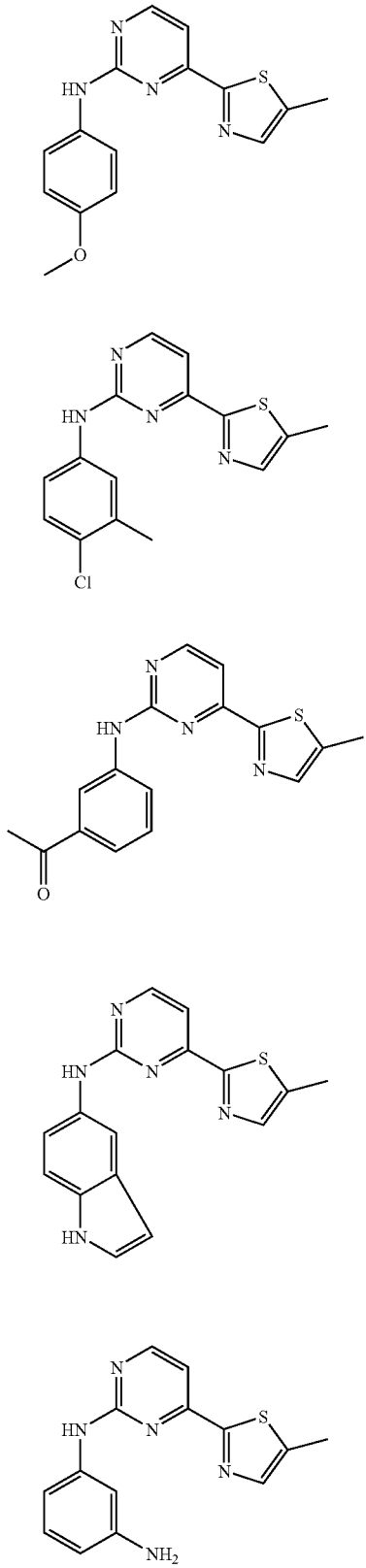
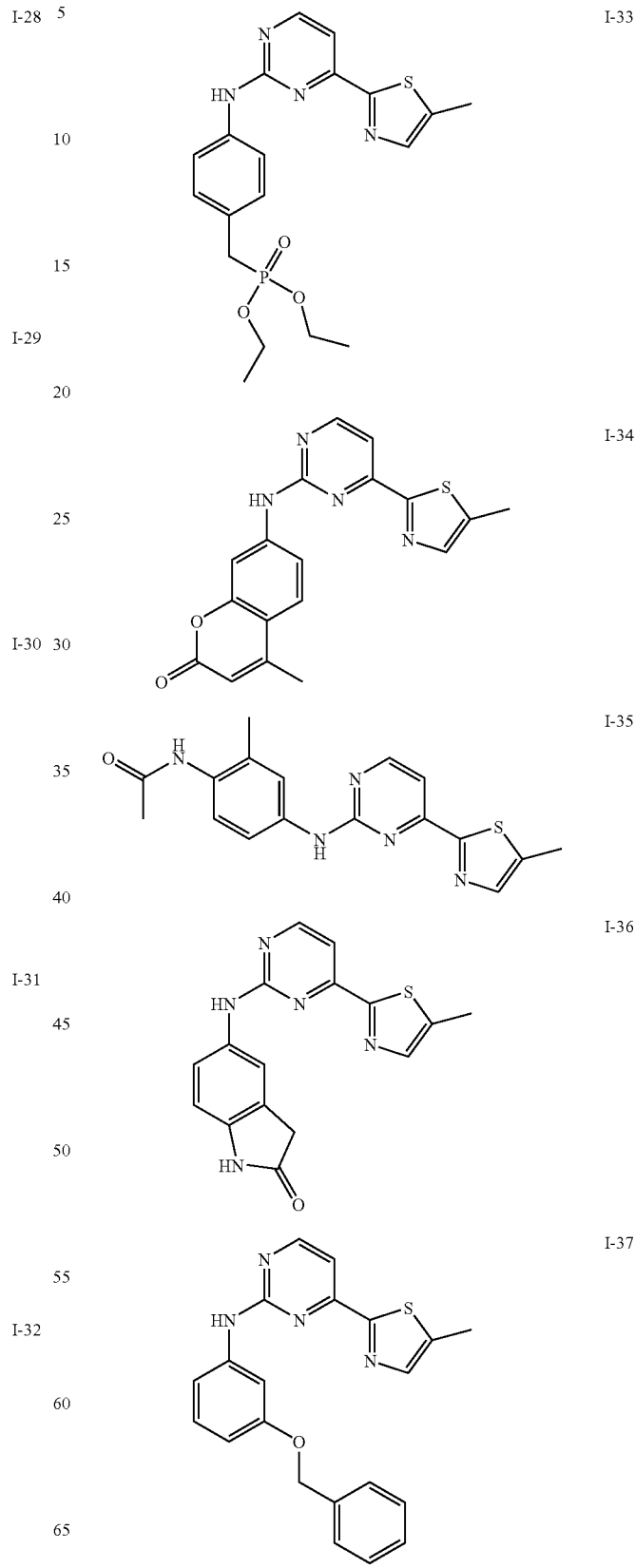

TABLE 1-continued
Examples of Compounds of Formula I:
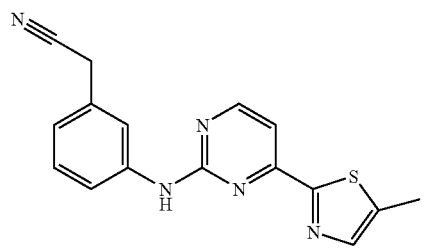
I-38
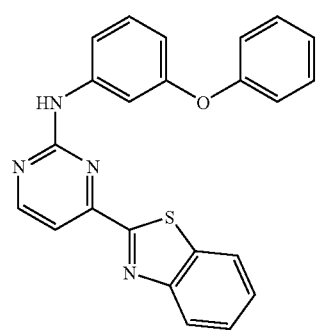
I-39
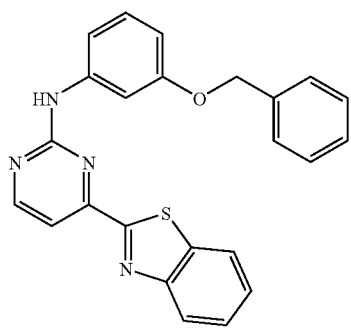
I-40
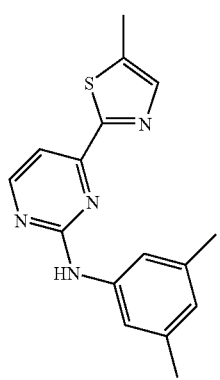
I-41
TABLE 1-continued
Examples of Compounds of Formula I:
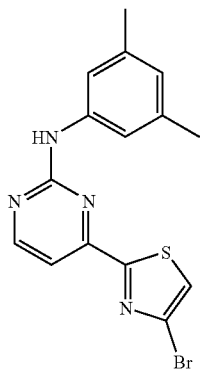
I-42
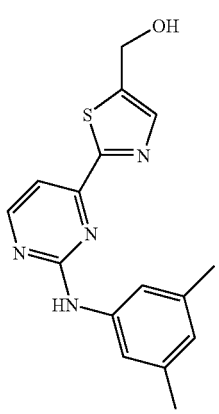
I-43
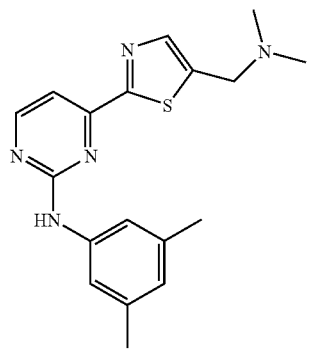
I-44
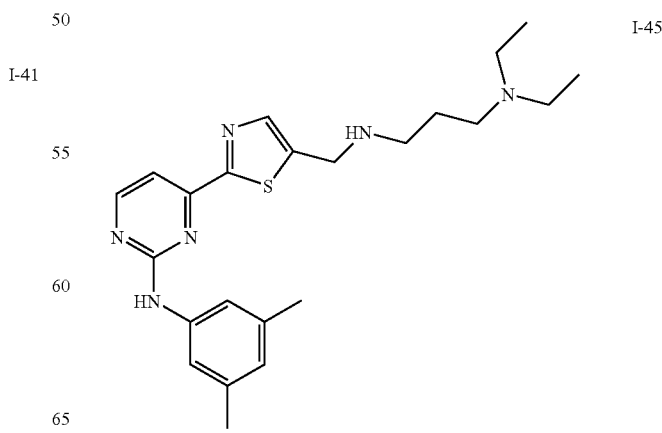
I-45

TABLE 1-continued
Examples of Compounds of Formula I:
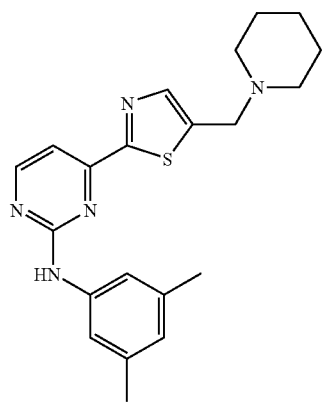
I-46
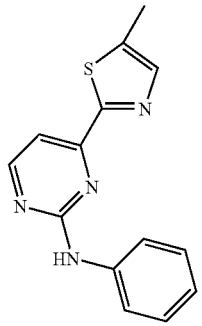
I-49
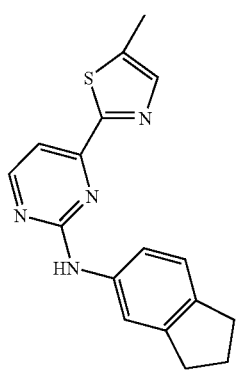
I-50
I-47
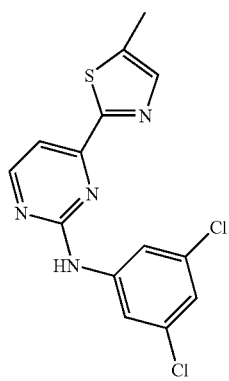
I-51
I-48
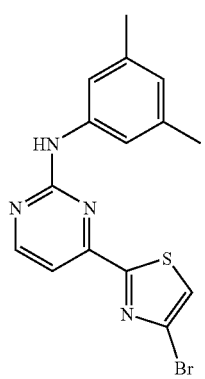
I-52

TABLE 1-continued
Examples of Compounds of Formula I:
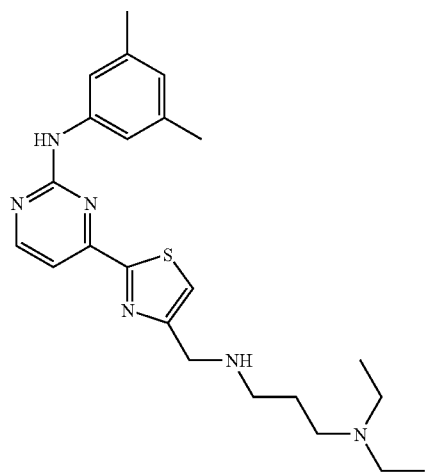
I-53
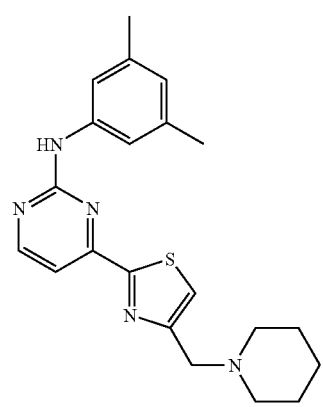
I-54
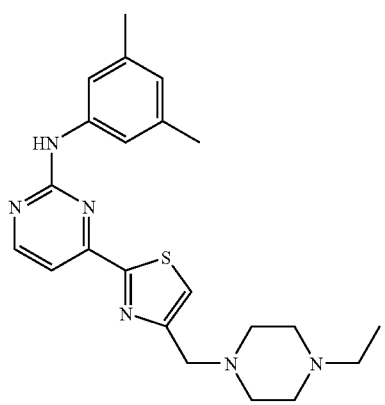
I-55
TABLE 1-continued
Examples of Compounds of Formula I:
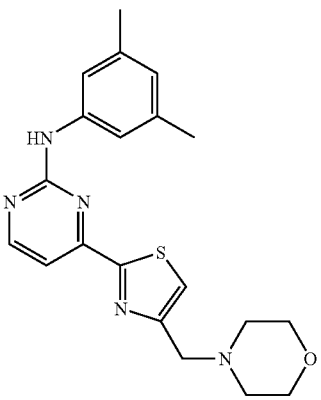
I-56
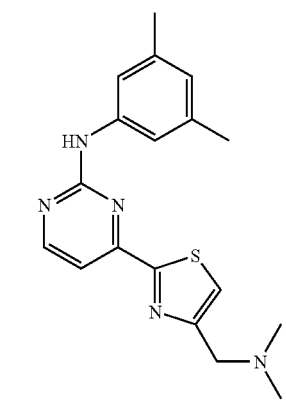
I-57
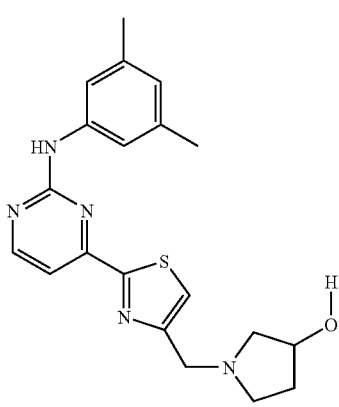
I-58

TABLE 1-continued
Examples of Compounds of Formula I:
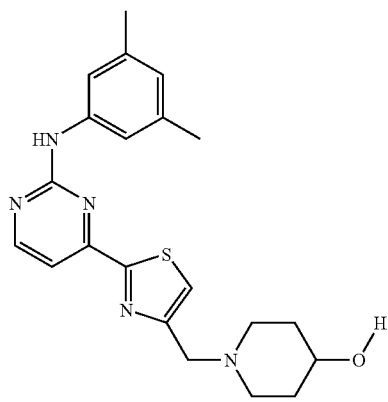
I-59
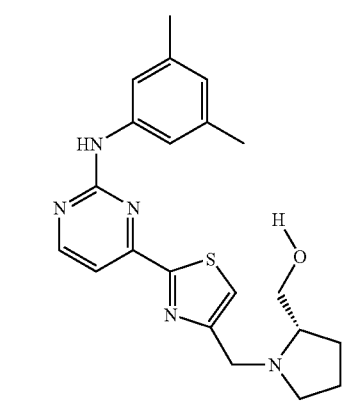
I-60
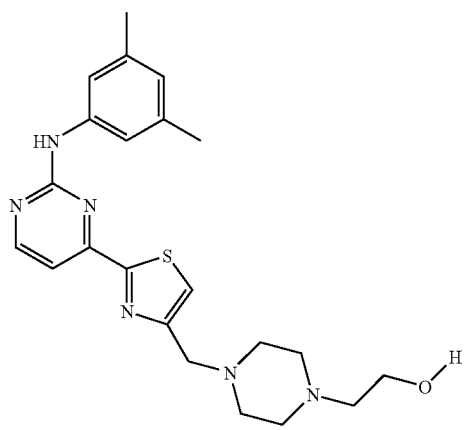
I-61
TABLE 1-continued
Examples of Compounds of Formula I:
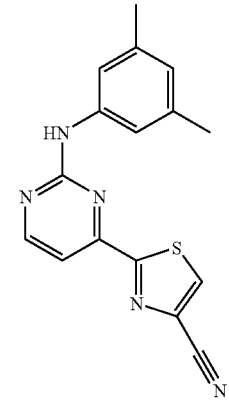
I-62
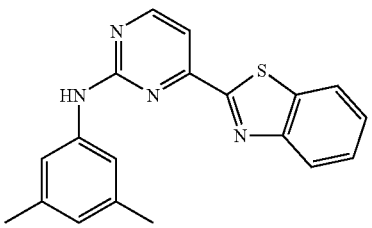
I-63
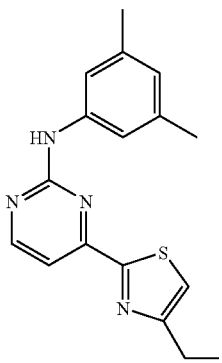
I-64
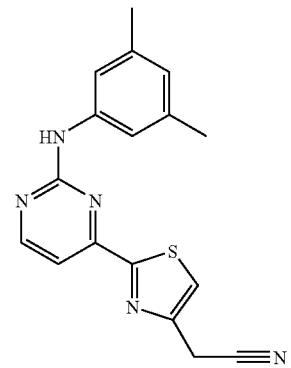
I-65

TABLE 1-continued
Examples of Compounds of Formula I:
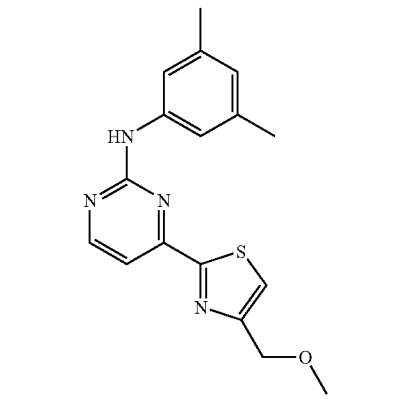
I-66
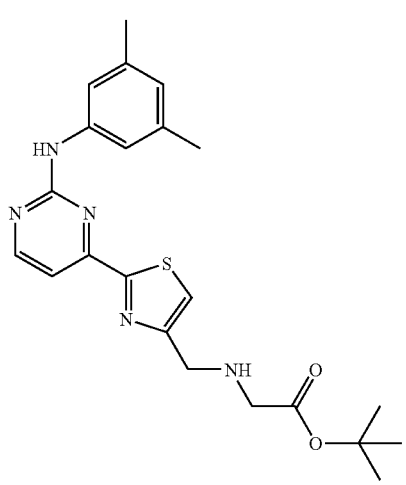
I-67
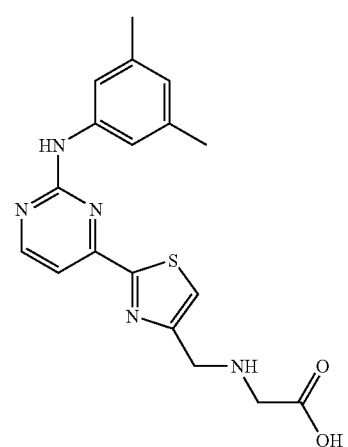
I-68
TABLE 1-continued
Examples of Compounds of Formula I:
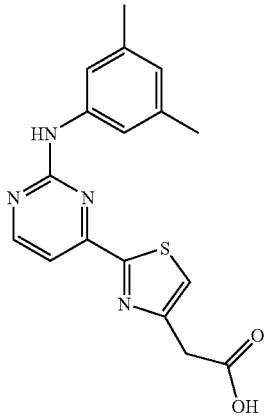
I-69
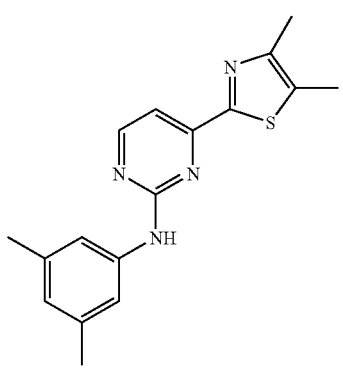
I-70
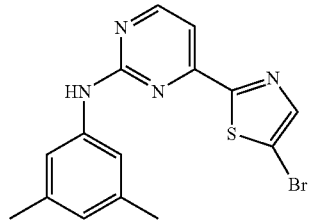
I-71
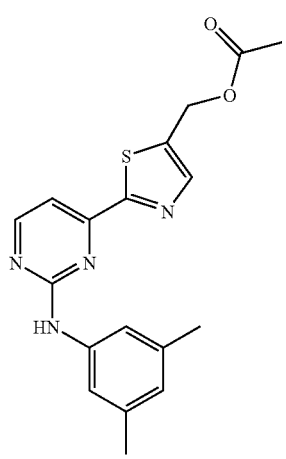
I-72

TABLE 1-continued
Examples of Compounds of Formula I:
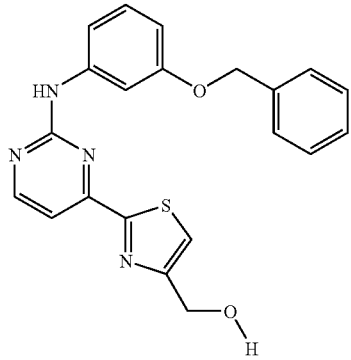
I-73
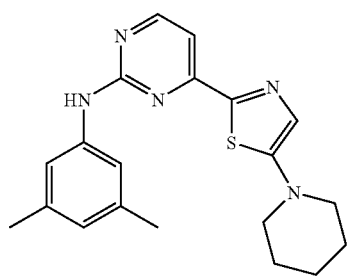
I-74
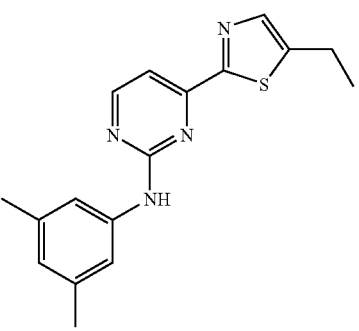
I-75
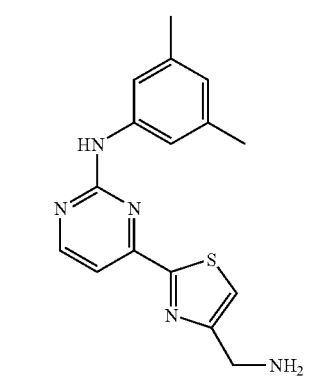
I-76
TABLE 1-continued
Examples of Compounds of Formula I:
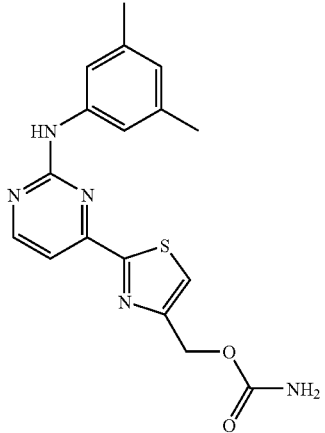
I-77
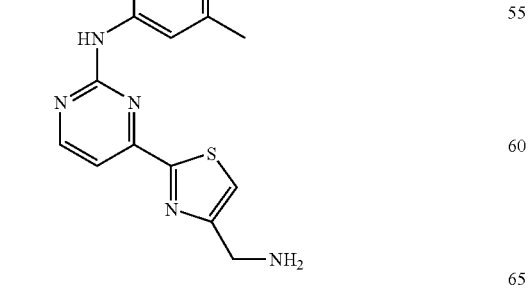
I-78
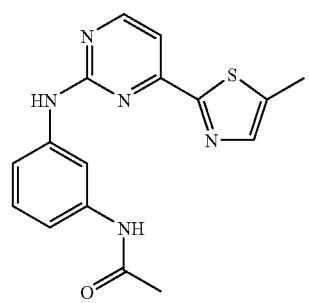
I-79

TABLE 1-continued
Examples of Compounds of Formula I:
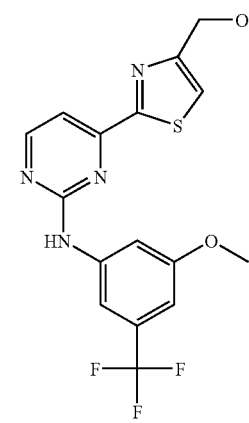

TABLE 1-continued
Examples of Compounds of Formula I:
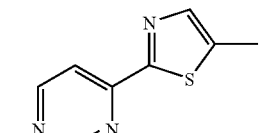
I-88
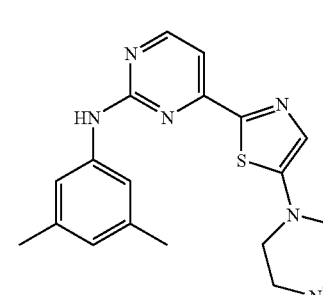
I-89
I-90
I-91
TABLE 1-continued
Examples of Compounds of Formula I:
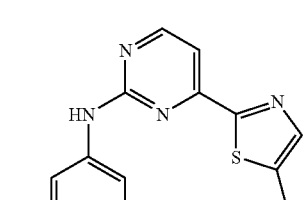
I-92
I-93
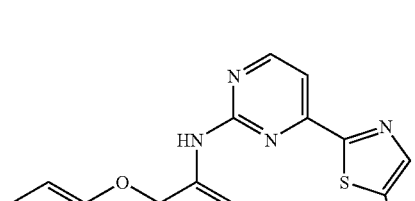
I-94
I-95
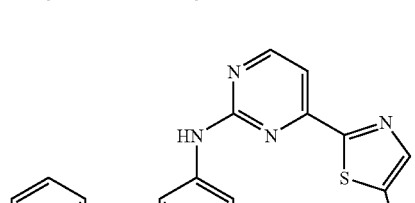
I-96

TABLE 1-continued
Examples of Compounds of Formula I:
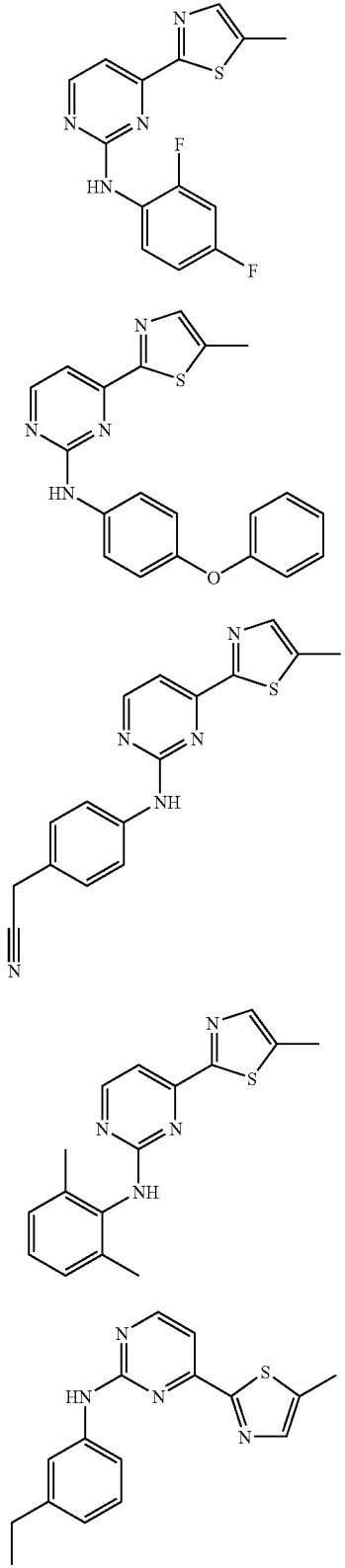
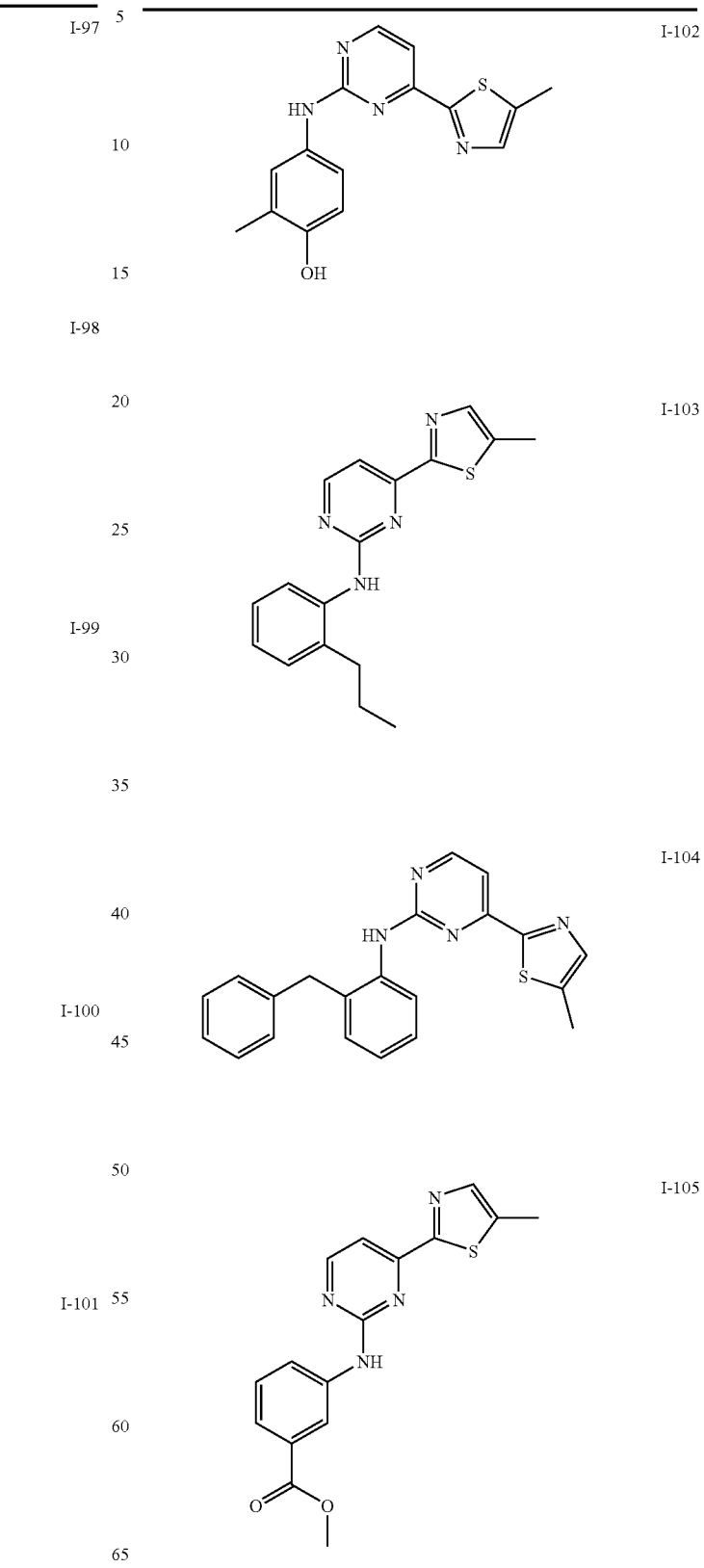

TABLE 1-continued

Examples of Compounds of Formula I:

TABLE 1-continued
Examples of Compounds of Formula I:
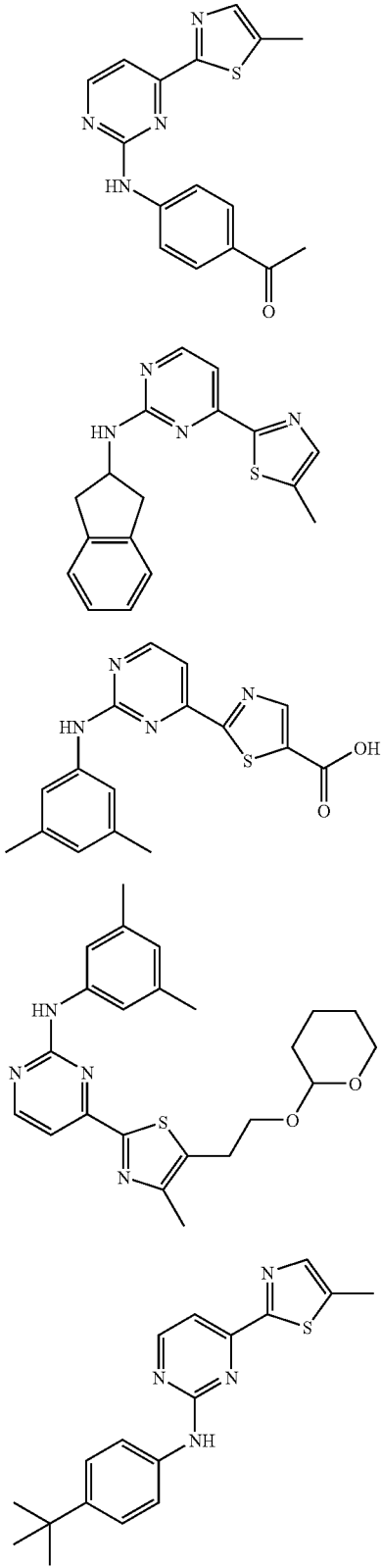
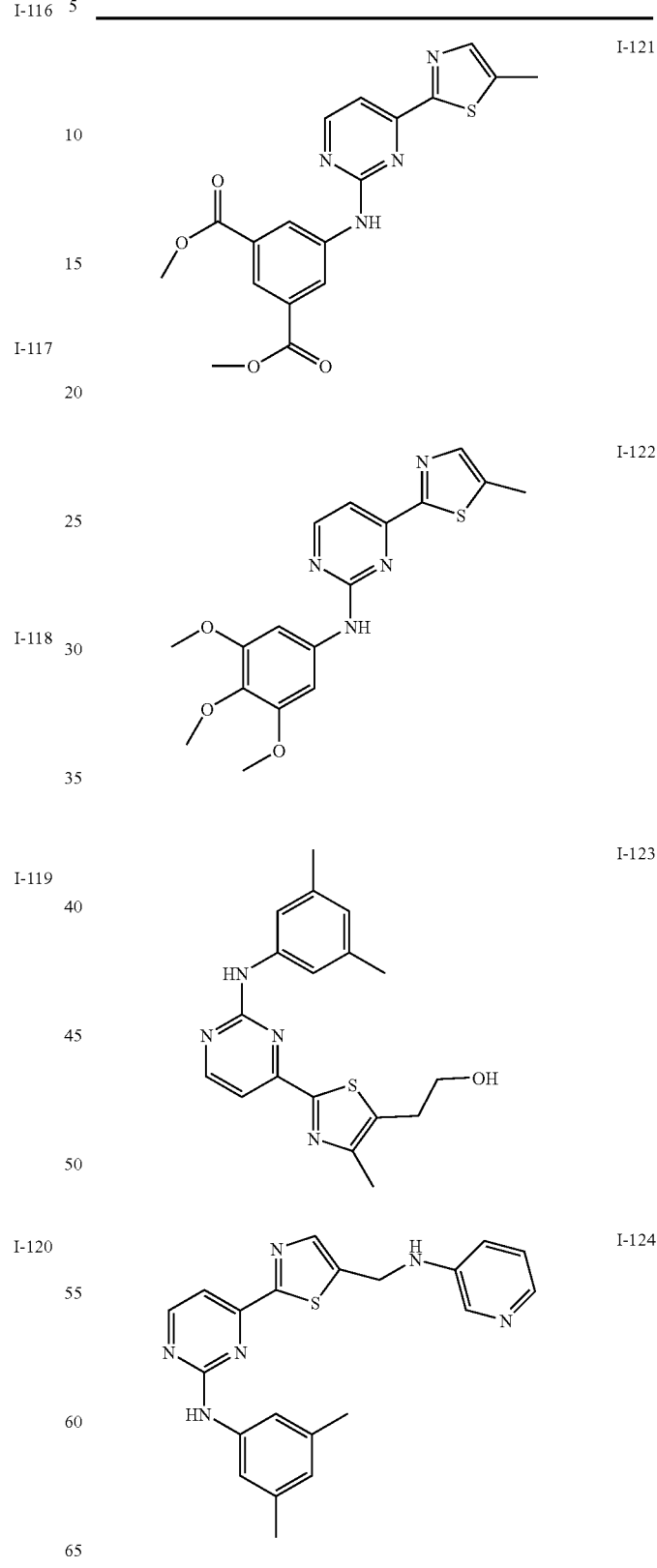

TABLE 1-continued
Examples of Compounds of Formula I:
I-125
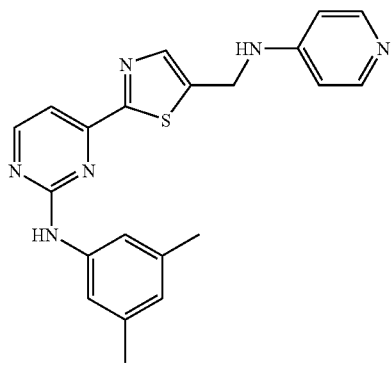
I-126
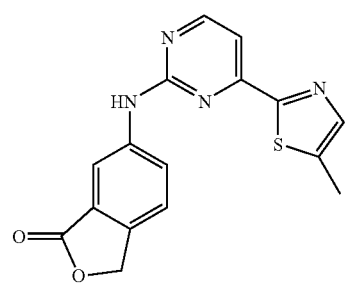
I-127
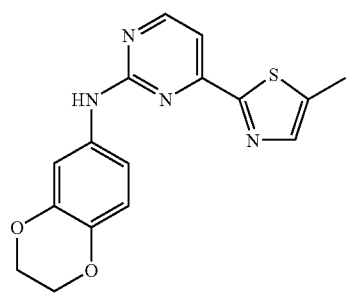
I-128
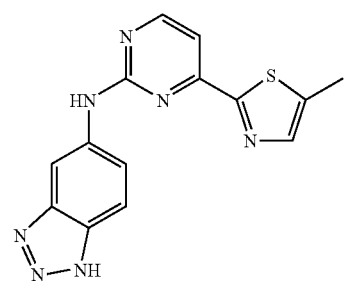
I-129
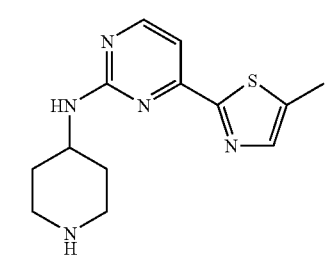
TABLE 1-continued
Examples of Compounds of Formula I:
I-130
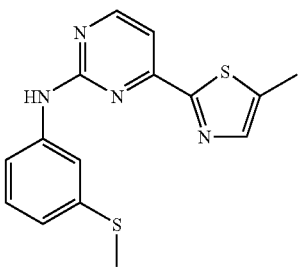
I-131
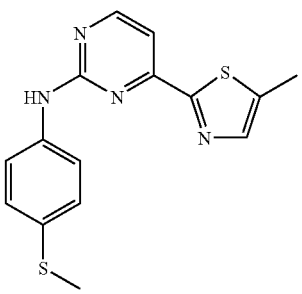
I-132
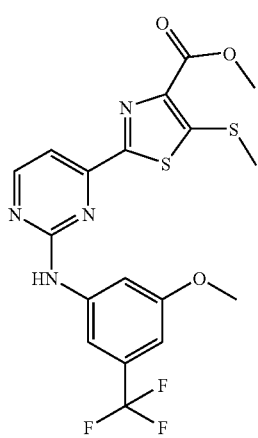
I-133
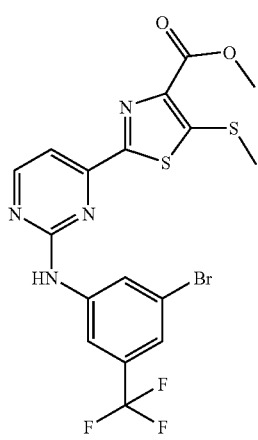

TABLE 1-continued
Examples of Compounds of Formula I:
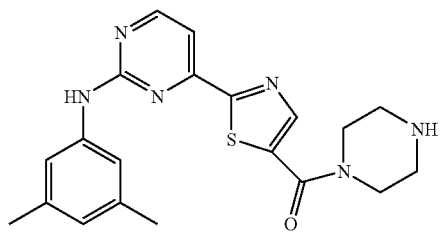
I-134
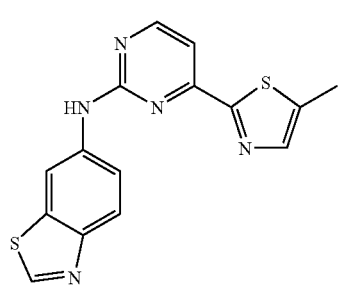
I-135
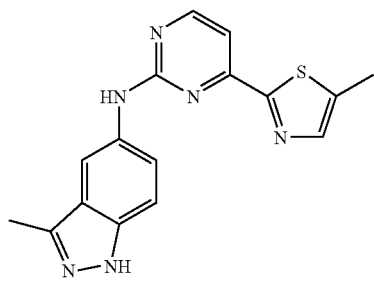
I-136
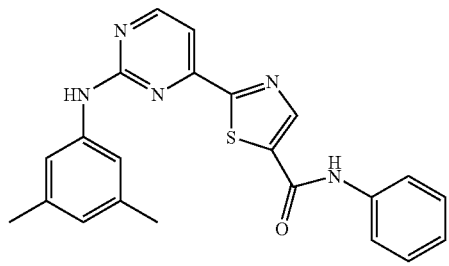
I-137
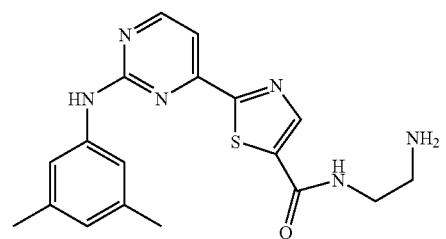
I-138
TABLE 1-continued
Examples of Compounds of Formula I:
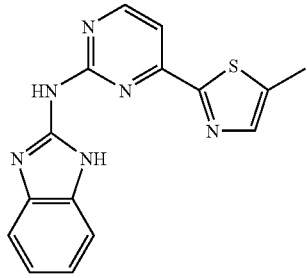
I-139
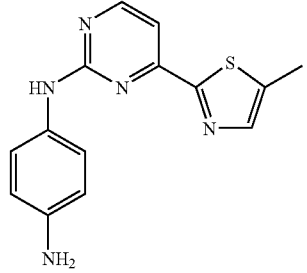
I-140
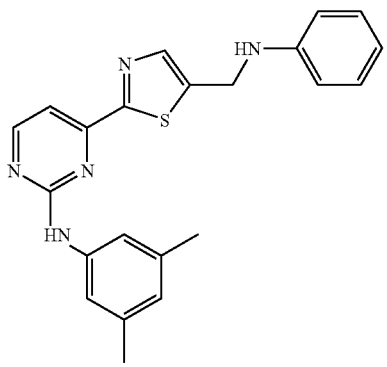
I-141
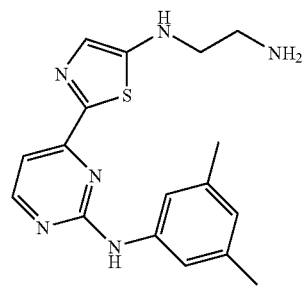
I-142
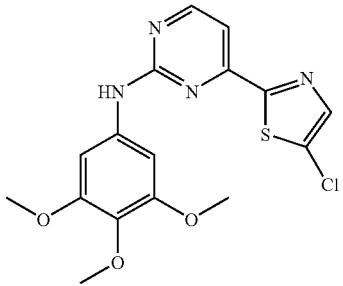
I-143

TABLE 1-continued
Examples of Compounds of Formula I:
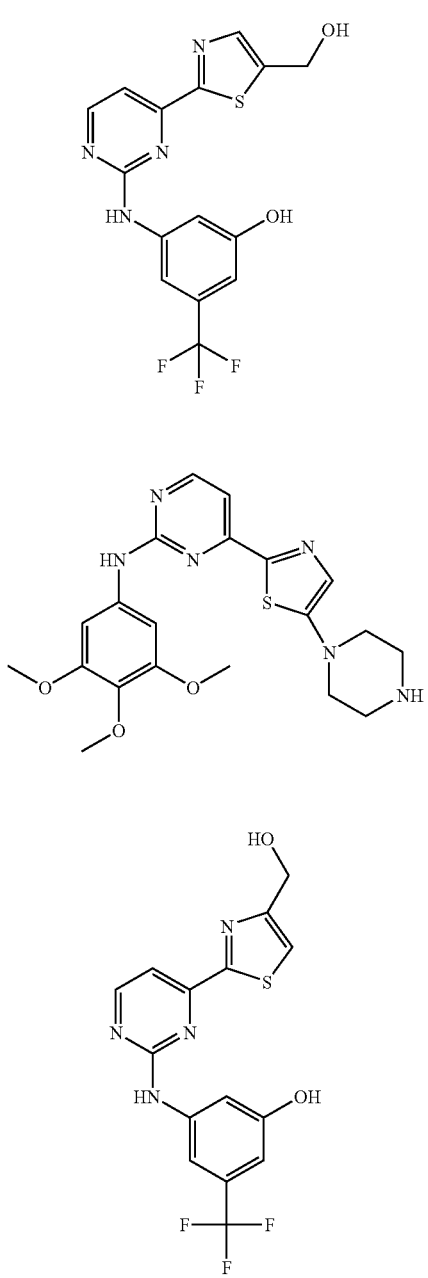
I-144
I-145
I-146
I-147
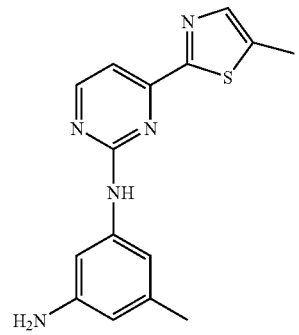
I-148
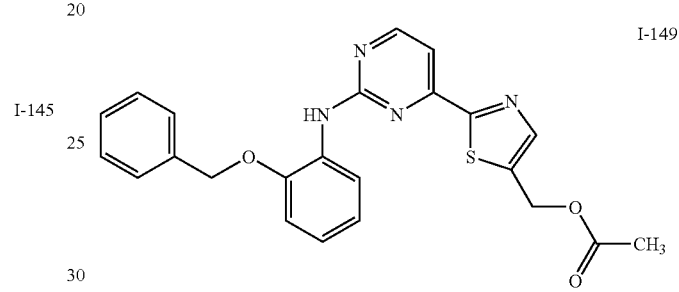
I-149
I-150
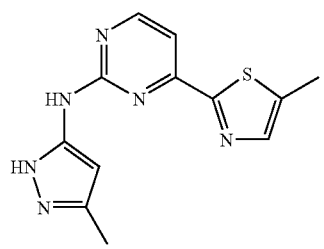
I-151
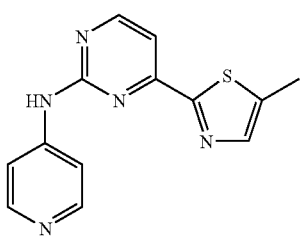
I-152

TABLE 1-continued
Examples of Compounds of Formula I:
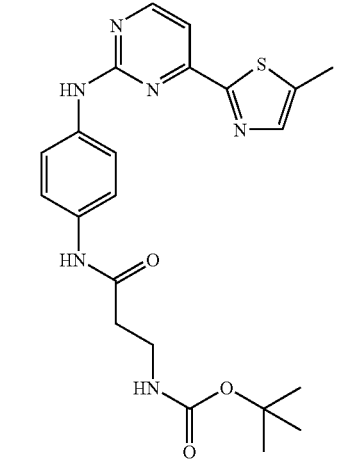
I-153
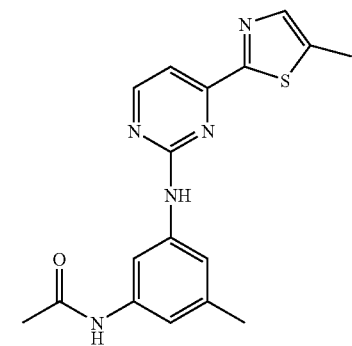
I-154
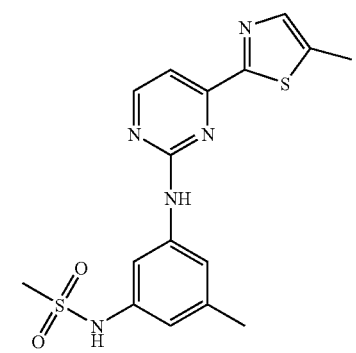
I-155
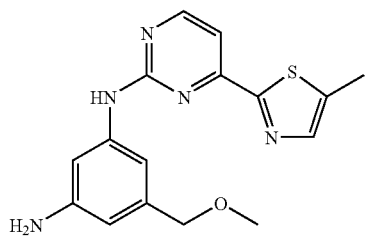
I-156
TABLE 1-continued
Examples of Compounds of Formula I:
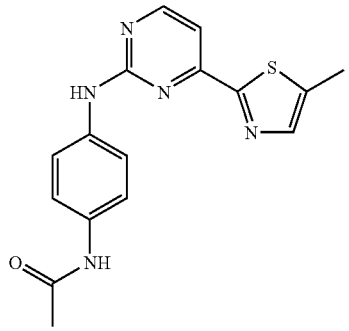
I-157
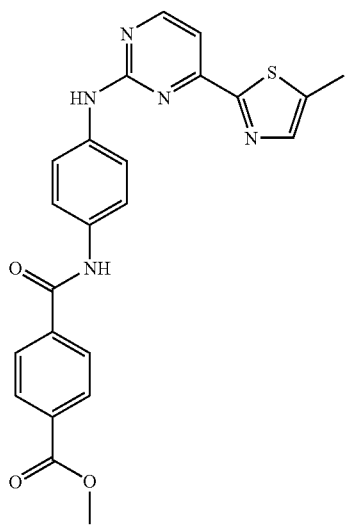
I-158
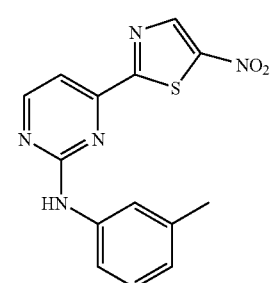
I-159
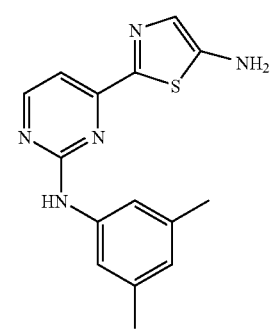
I-160

TABLE 1-continued
Examples of Compounds of Formula I:
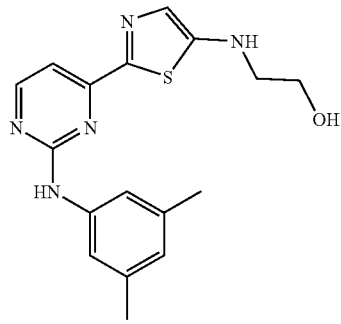
I-161
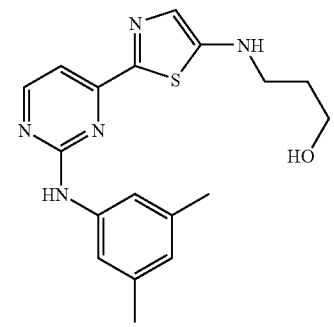
I-162
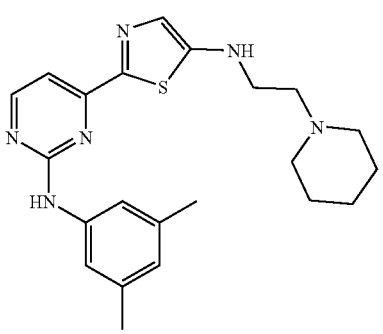
I-163
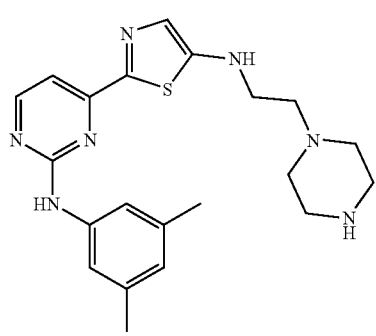
I-164
TABLE 1-continued
Examples of Compounds of Formula I:
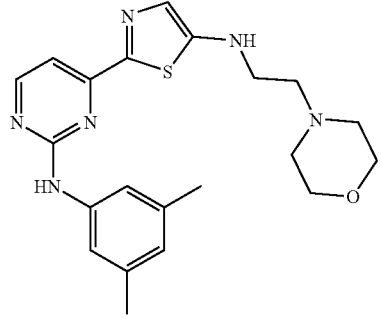
I-165
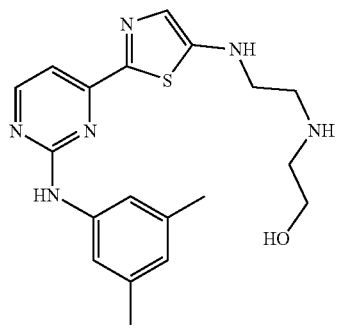
I-166
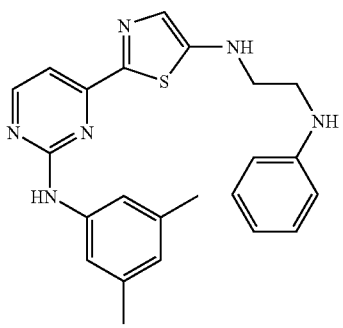
I-167
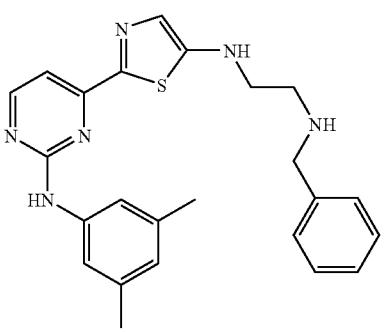
I-168

TABLE 1-continued
Examples of Compounds of Formula I:
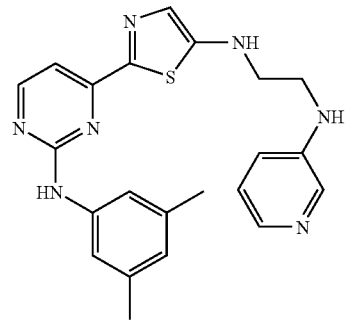
I-169
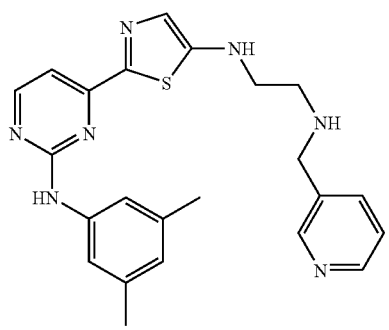
I-170
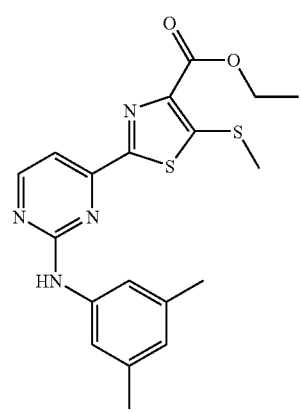
I-171
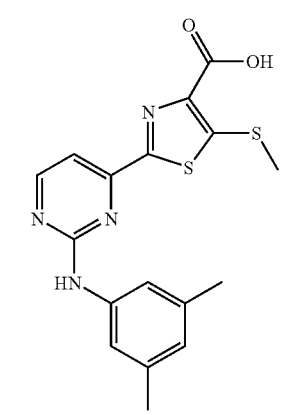
I-172
TABLE 1-continued
Examples of Compounds of Formula I:
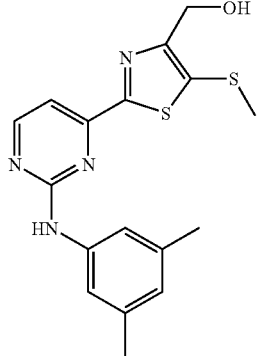
I-173
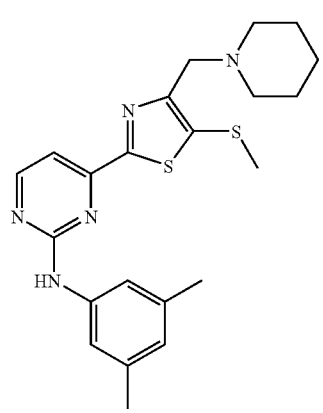
I-174
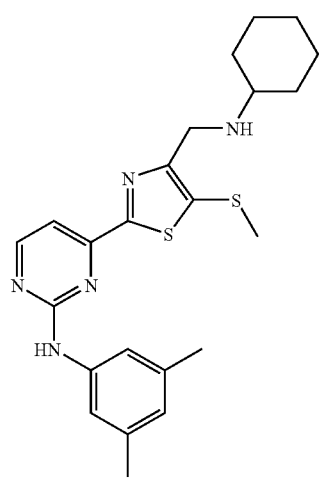
I-175

TABLE 1-continued
Examples of Compounds of Formula I:
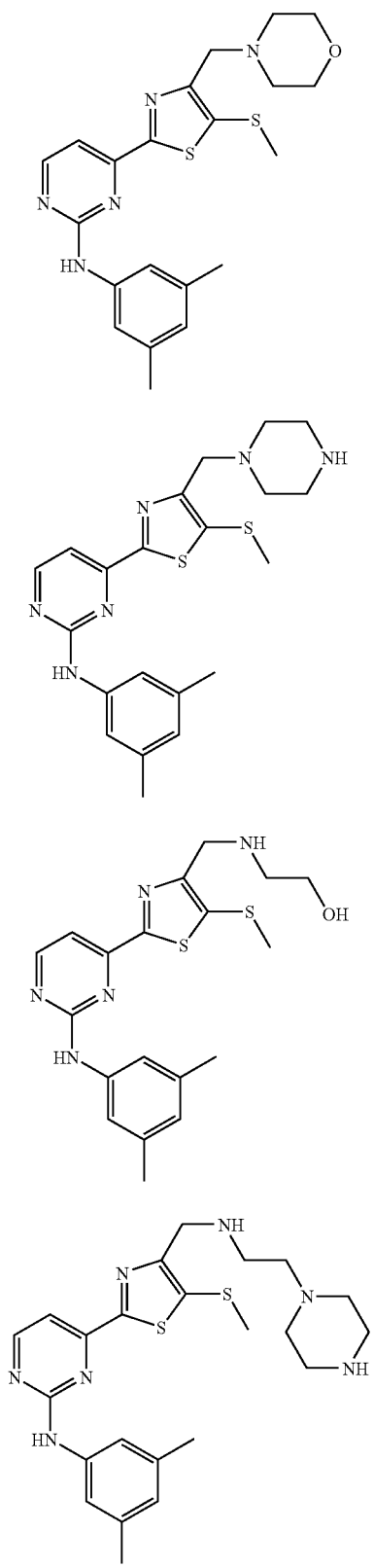
I-176
I-177
I-178
I-179
TABLE 1-continued
Examples of Compounds of Formula I:
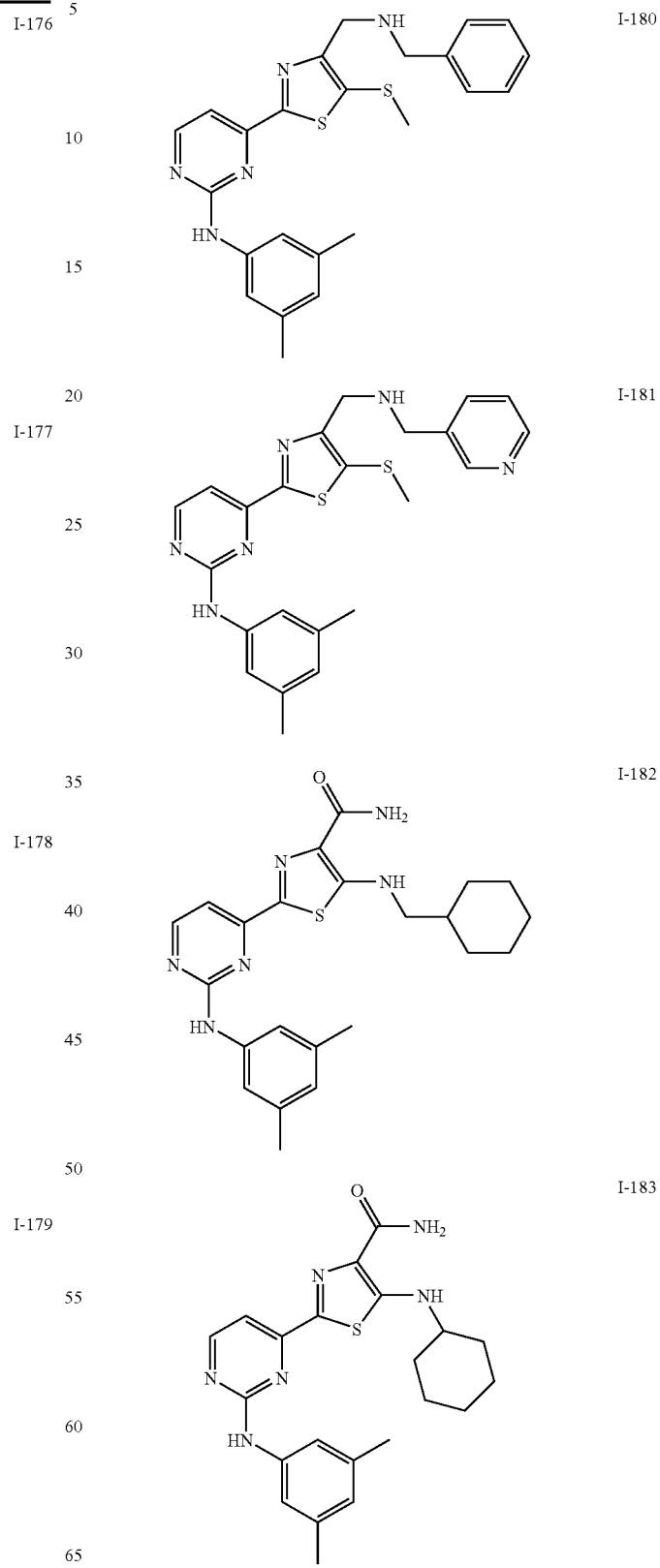
I-180
I-181
I-182
I-183

TABLE 1-continued
Examples of Compounds of Formula I:
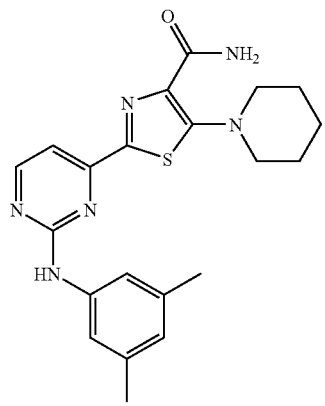
I-184
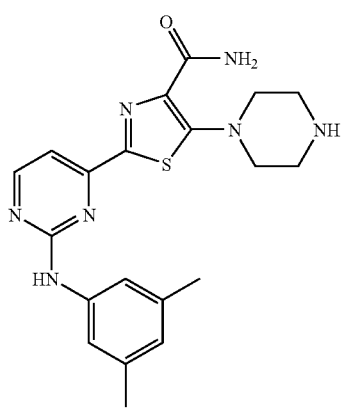
I-185
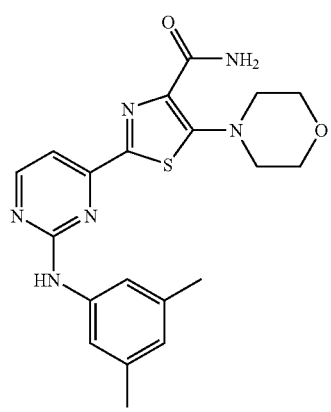
I-186
TABLE 1-continued
Examples of Compounds of Formula I:
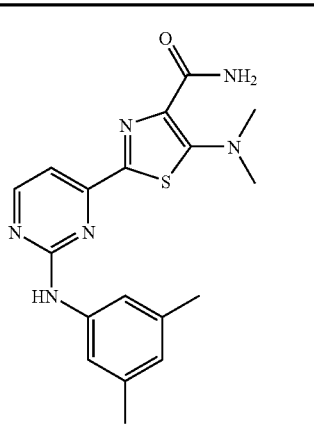
I-187
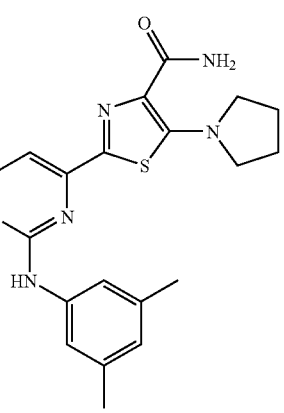
I-188
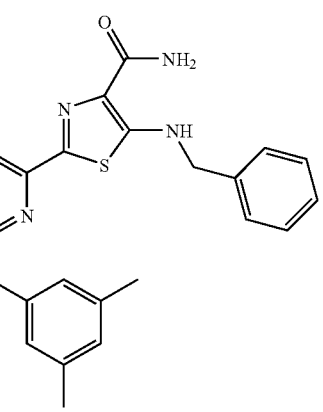
I-189

TABLE 1-continued

Examples of Compounds of Formula I:

I-190, I-191, I-192, I-193, I-194, I-195, I-196

TABLE 1-continued
Examples of Compounds of Formula I:
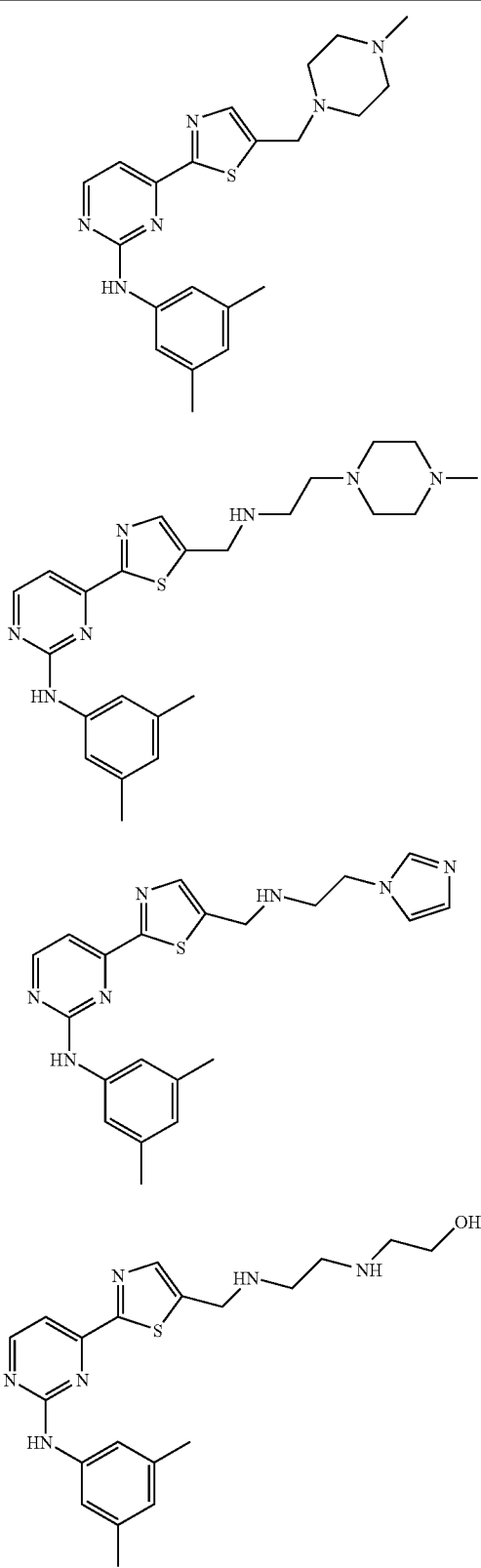
I-197
I-198
I-199
I-200
TABLE 1-continued
Examples of Compounds of Formula I:
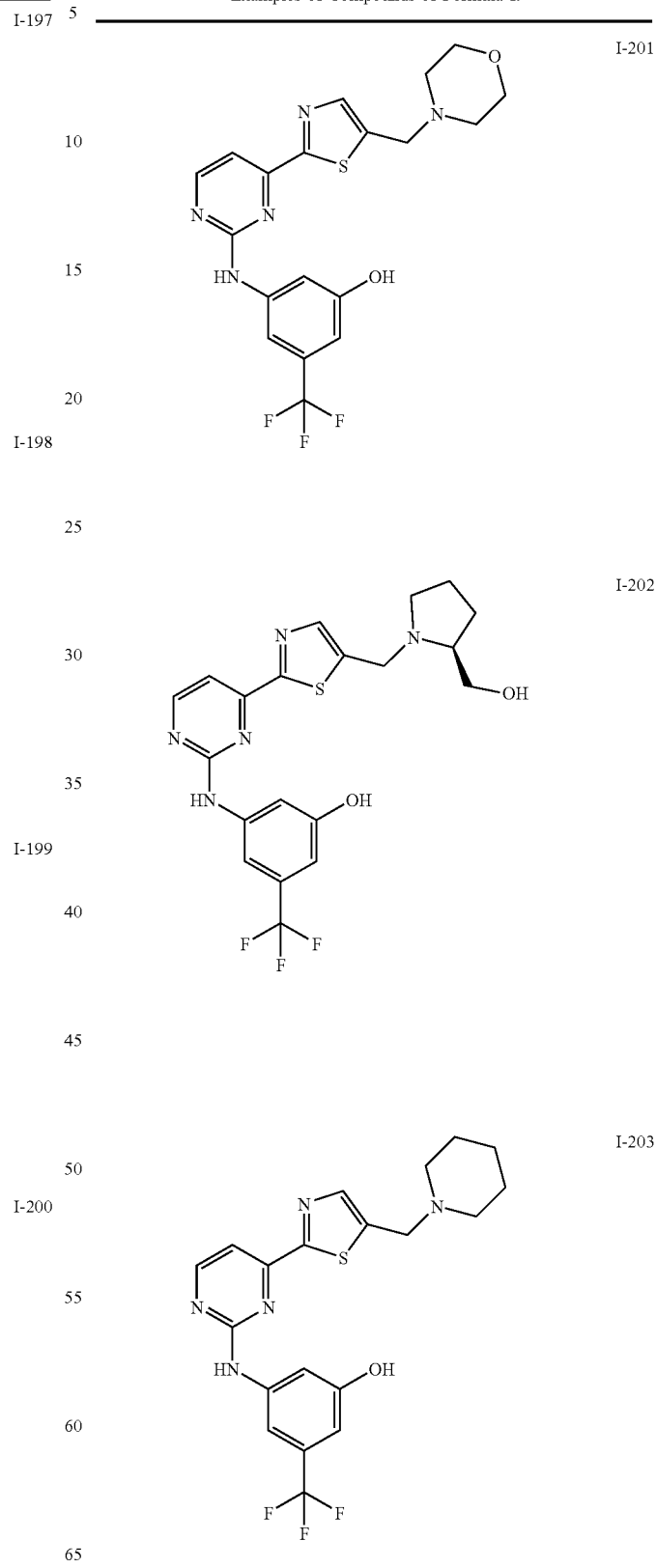
I-201
I-202
I-203

TABLE 1-continued

Examples of Compounds of Formula I:

I-204, I-205, I-206, I-207, I-208, I-209

TABLE 1-continued
Examples of Compounds of Formula I:
I-210
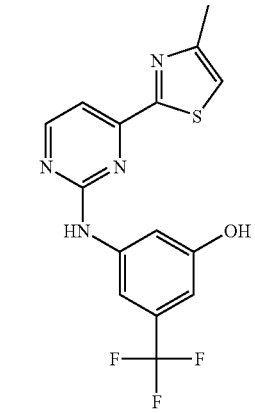
I-211
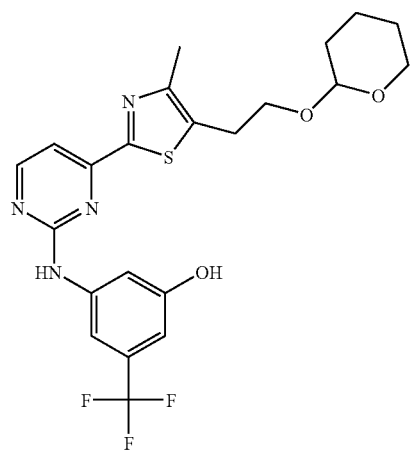
I-212
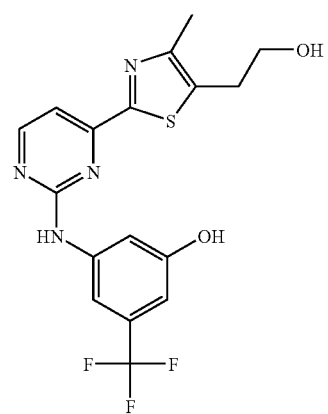
TABLE 1-continued
Examples of Compounds of Formula I:
I-213
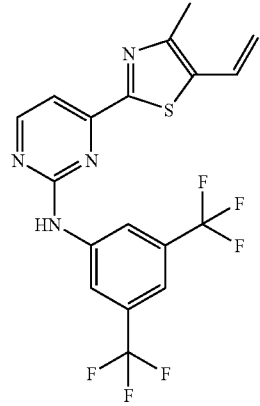
I-214
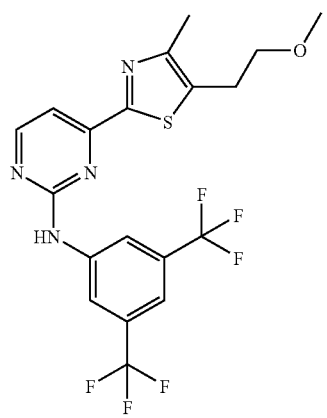
I-215
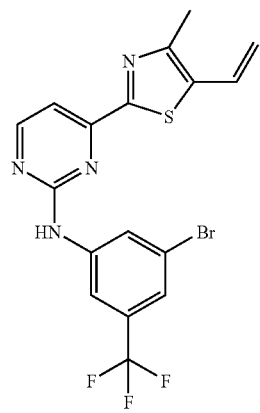

TABLE 1-continued
Examples of Compounds of Formula I:
I-216 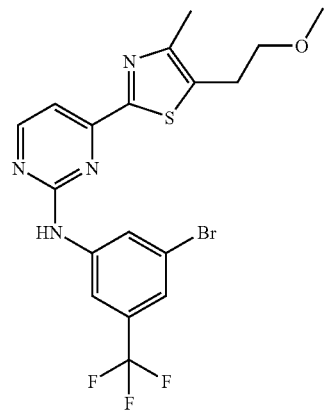
I-217 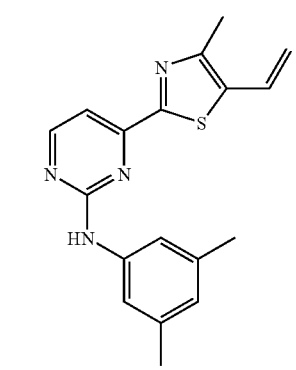
I-218 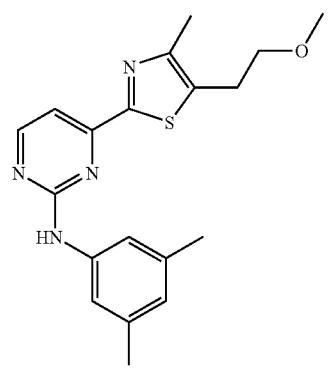
I-219 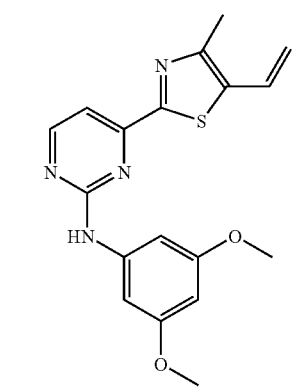
TABLE 1-continued
Examples of Compounds of Formula I:
I-220 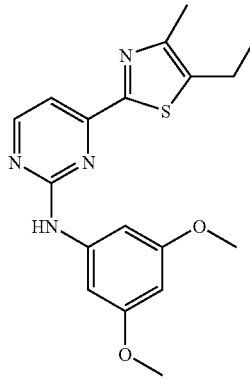
I-221 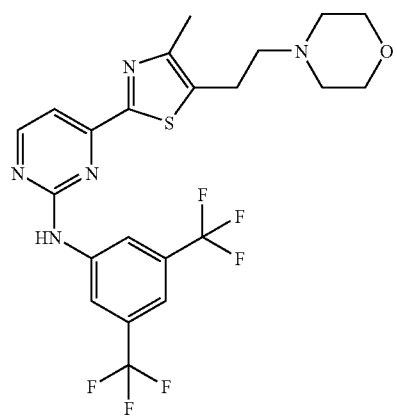
I-222 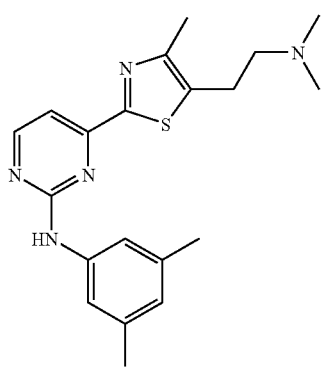
I-223 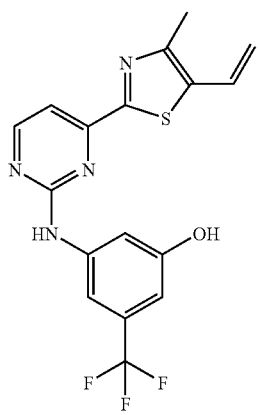

TABLE 1-continued
Examples of Compounds of Formula I:
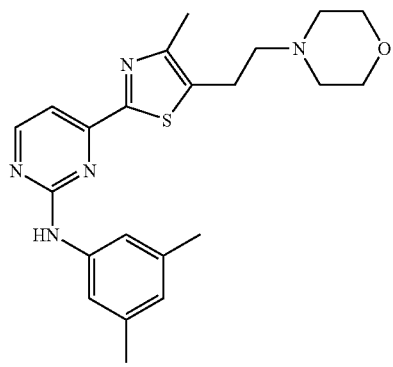
I-224
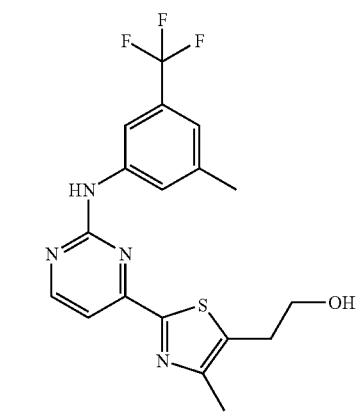
I-225
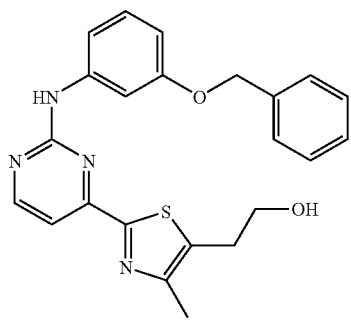
I-226
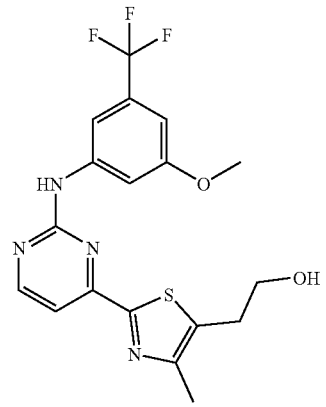
I-227
TABLE 1-continued
Examples of Compounds of Formula I:
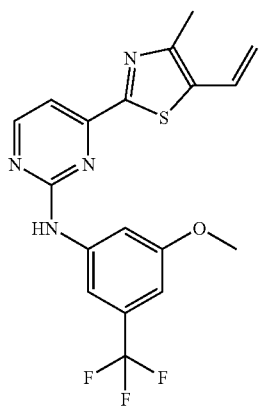
I-228
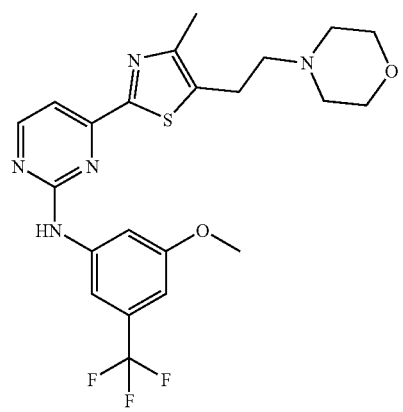
I-229
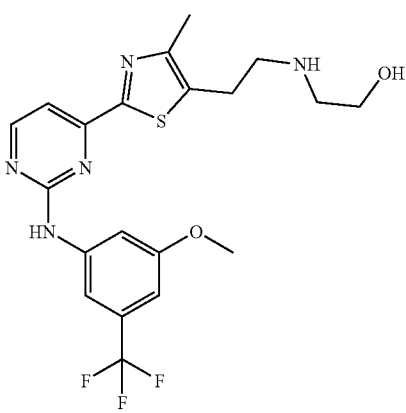
I-230

TABLE 1-continued

Examples of Compounds of Formula I:

I-231, I-232, I-233, I-234, I-235, I-236, I-237

TABLE 1-continued
Examples of Compounds of Formula I:
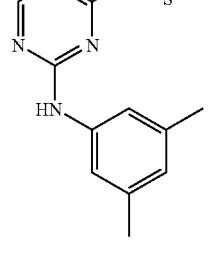
I-238
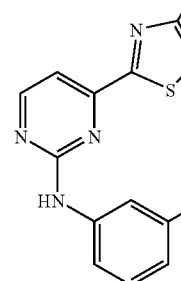
I-239
I-240
I-241
TABLE 1-continued
Examples of Compounds of Formula I:
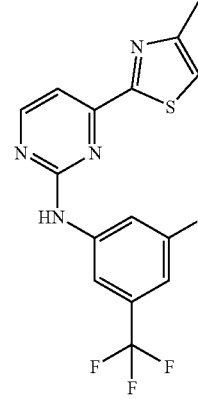
I-242
I-243
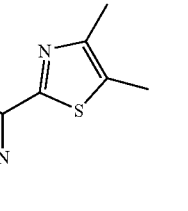
I-244
I-245

TABLE 1-continued
Examples of Compounds of Formula I:
I-246
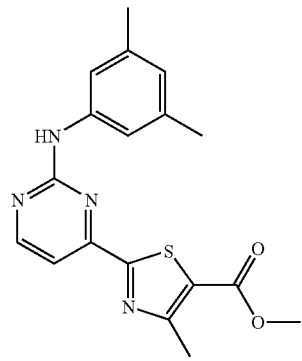
I-247
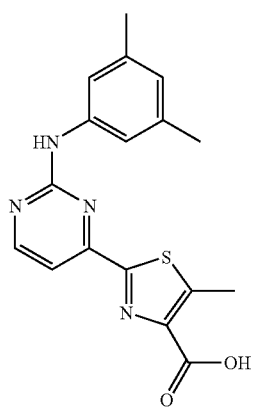
I-248
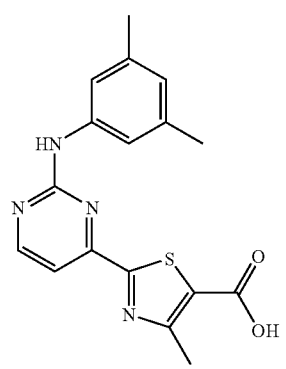
I-249
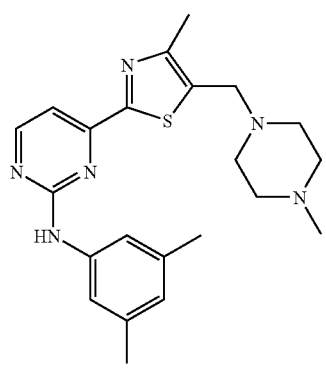
TABLE 1-continued
Examples of Compounds of Formula I:
I-250
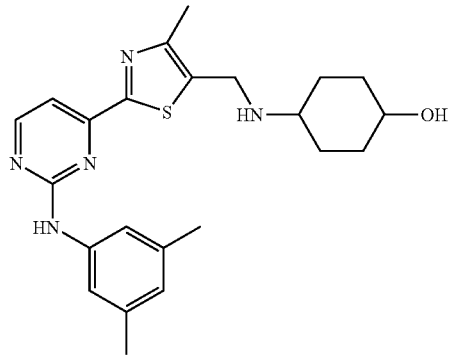
I-251
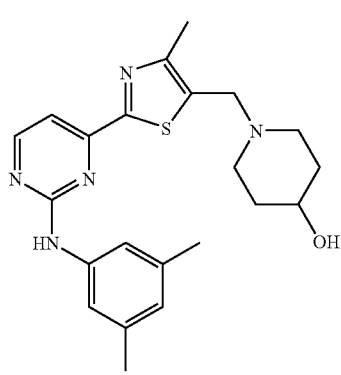
I-252
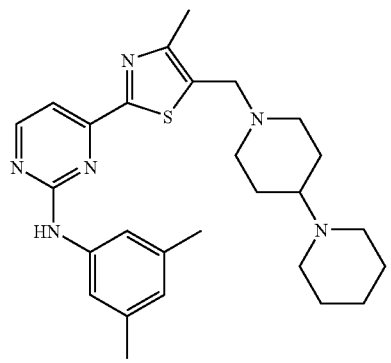
I-253
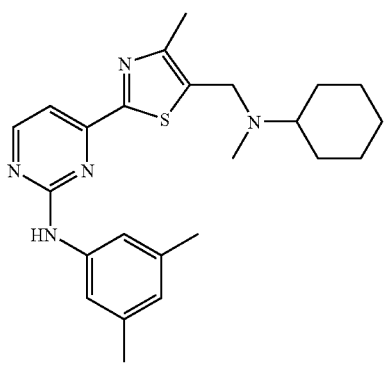

TABLE 1-continued
Examples of Compounds of Formula I:
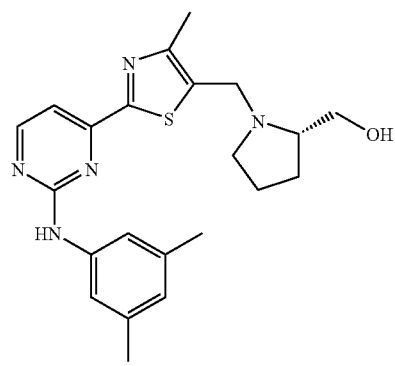
I-254
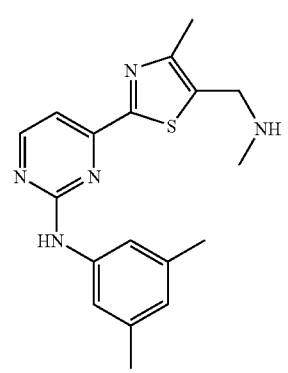
I-255
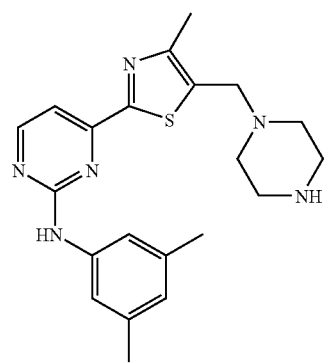
I-256
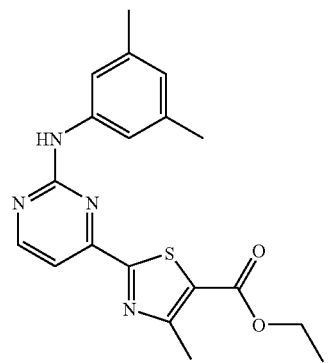
I-257
TABLE 1-continued
Examples of Compounds of Formula I:
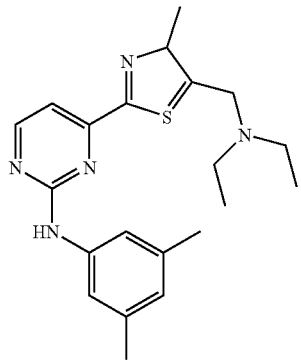
I-258
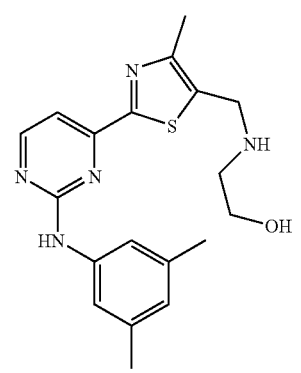
I-259
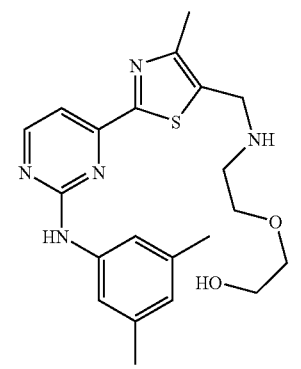
I-260
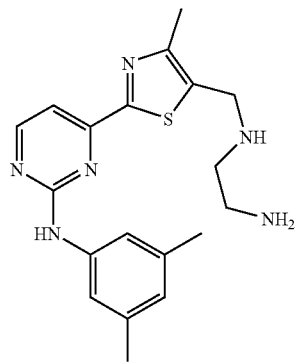
I-261

TABLE 1-continued
Examples of Compounds of Formula I:
I-262
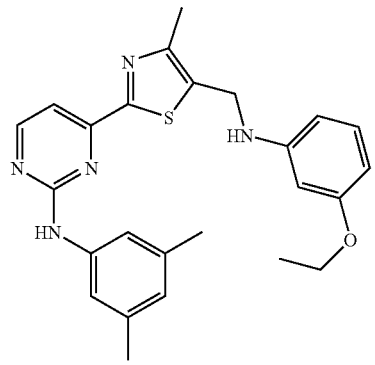
I-263
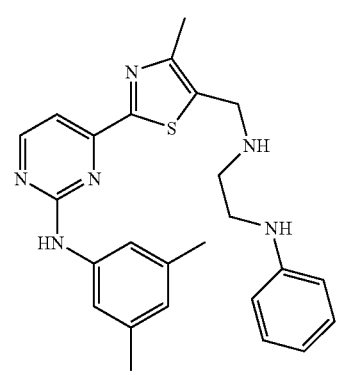
I-264
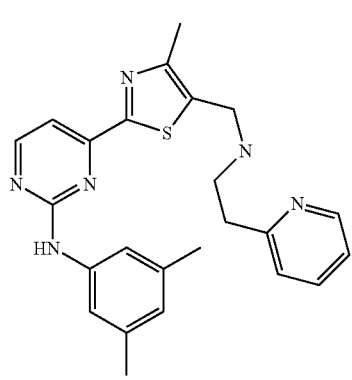
I-265
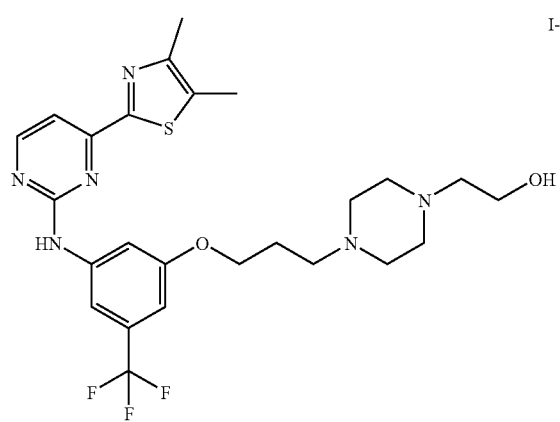
TABLE 1-continued
Examples of Compounds of Formula I:
I-266
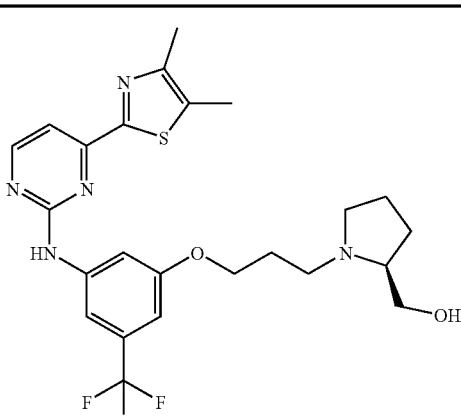
I-267
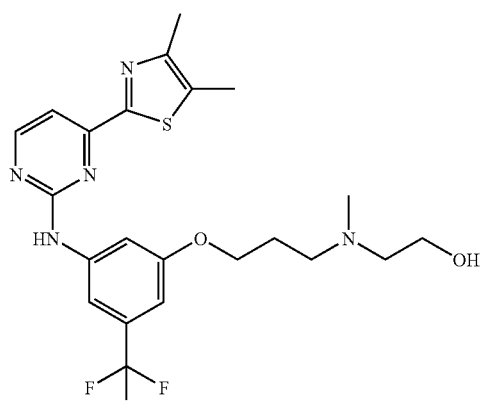
I-268
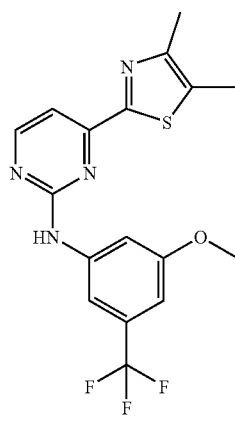

TABLE 1-continued

Examples of Compounds of Formula I:

I-269

I-270

I-271

I-272

I-273

I-274

I-275

TABLE 1-continued
Examples of Compounds of Formula I:
I-276
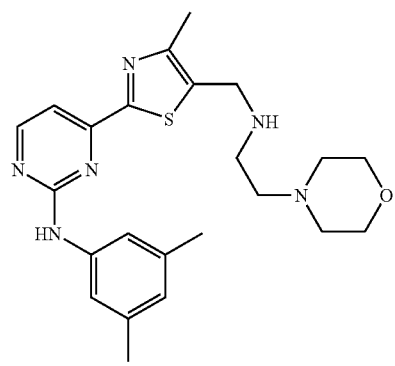
I-277
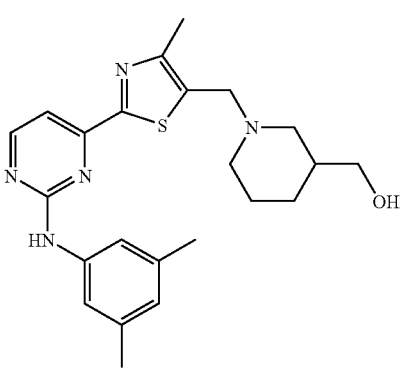
I-278
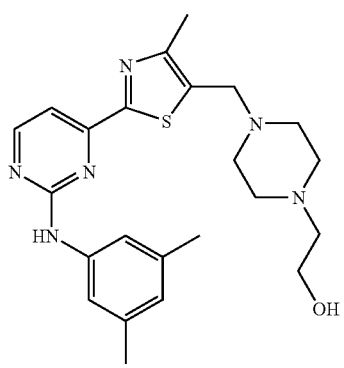
I-279
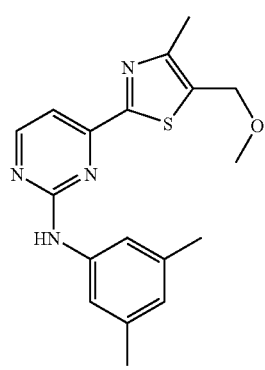
TABLE 1-continued
Examples of Compounds of Formula I:
I-280
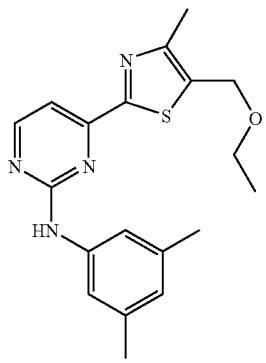
I-281
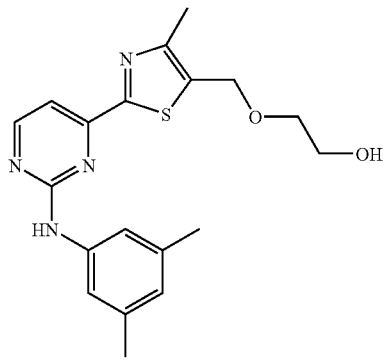
I-282
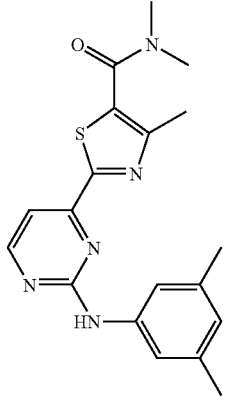
I-283
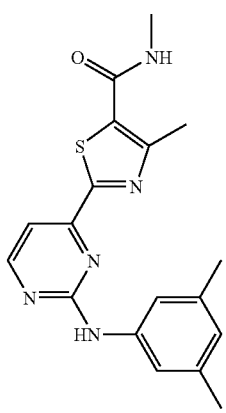

TABLE 1-continued

Examples of Compounds of Formula I:

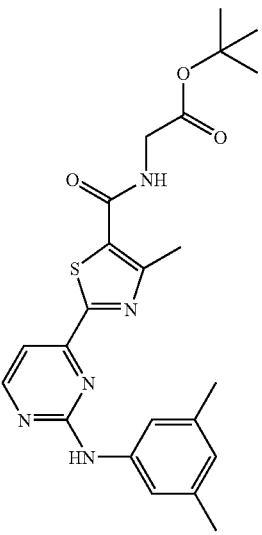
I-284

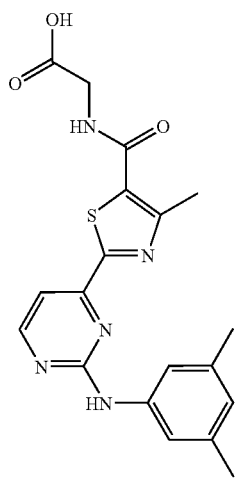
I-285

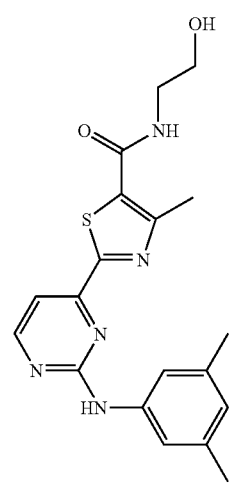
I-286

4. General Synthetic Methodology:

The compounds of this invention may be prepared in general by methods known to those skilled in the art for analogous compounds, as illustrated by the general scheme below, and the preparative examples that follow.

Scheme I below shows a general synthetic route that may be used used for preparing compounds of formula I.

Scheme I:

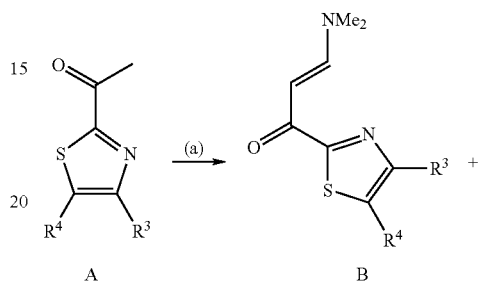

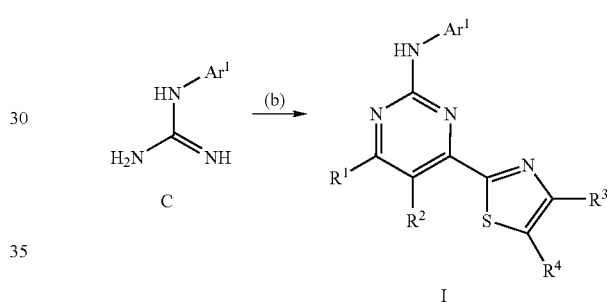

Reagents and conditions: (a) DMF-DMA, THF, 12-18 hours, room temperature; (b) Ethanol, reflux, 12-18 hours.

In step (a), a solution of 2-acetyl thiazole A in TBF is treated with dimethylformamide-dimethylacetal and the resulting mixture stirred at room temperature over night. The reaction mixture is concentrated in vacuo and the concentrate triturated with diethyl ether to afford B.

To prepare intermediate C, a mixture of $Ar^1NH_2$ and cyanamide in HCl (4N in dioxane) is heated at 120° C. overnight. After cooling to room temperature, aqueous work-up affords the desired guanidine compound C. One of skill in the art would recognize that a wide variety of aryl guanidines may be prepared and may thus be used to prepare compounds of formula I with a wide variety of $Ar^1$ rings.

In step (b), guanidine C is combined with enaminone B in ethanol in a sealed tube. The resulting mixture is heated at reflux overnight then concentrated and the crude product purified by column chromatography to afford the desired pyrimidine compound I. The details of the conditions used for producing these compounds are set forth in the Examples.

In one exemplary embodiment, phenylguanidine C-i is prepared and used to generate compounds of general formula II, as depicted generally below.

Scheme II:
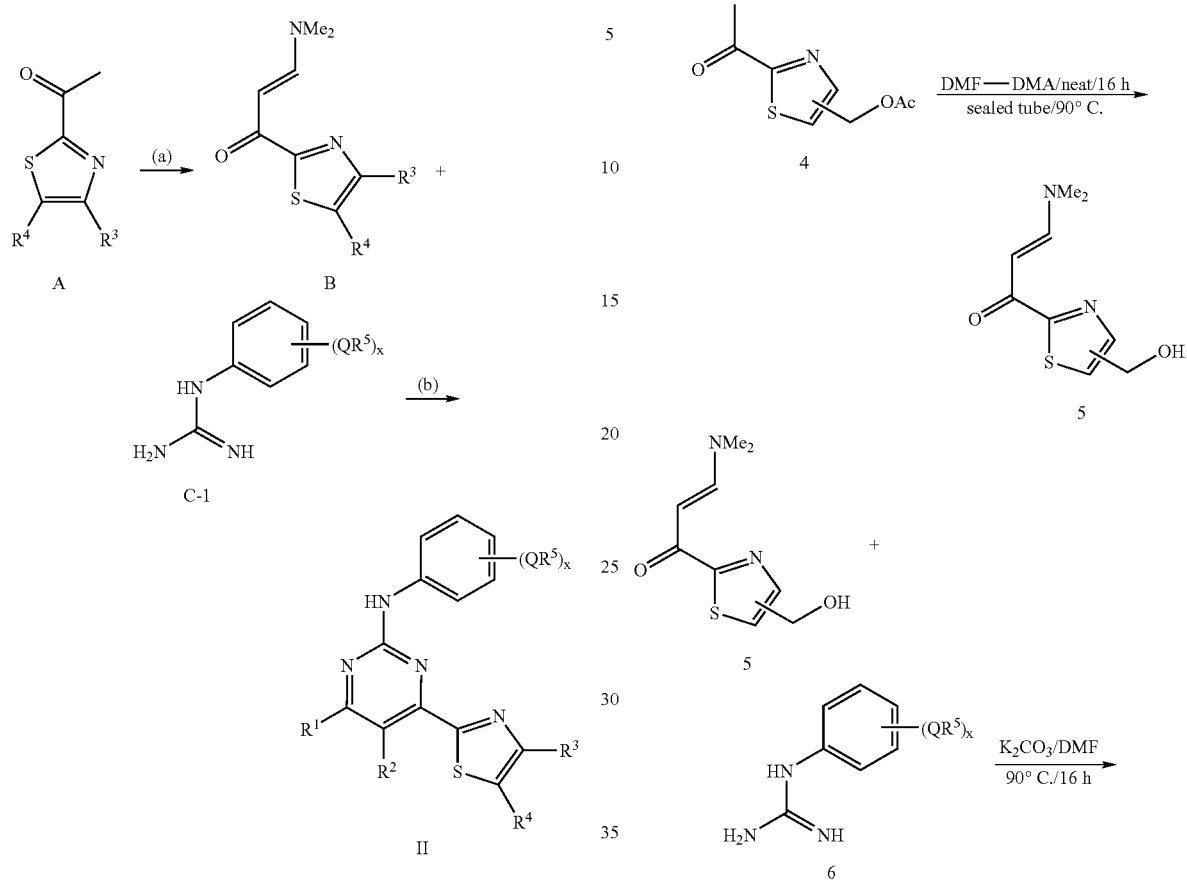
Schemes III, IV, V, VI, VII, VIII, IX, X, XI, XII, and XIII below depict the synthesis of certain exemplary compounds of the invention.
Scheme III below depicts the synthesis of exemplary compounds where $R^3$ or $R^4$ is $CH_2OH$ or $CH_2NRR^7$:
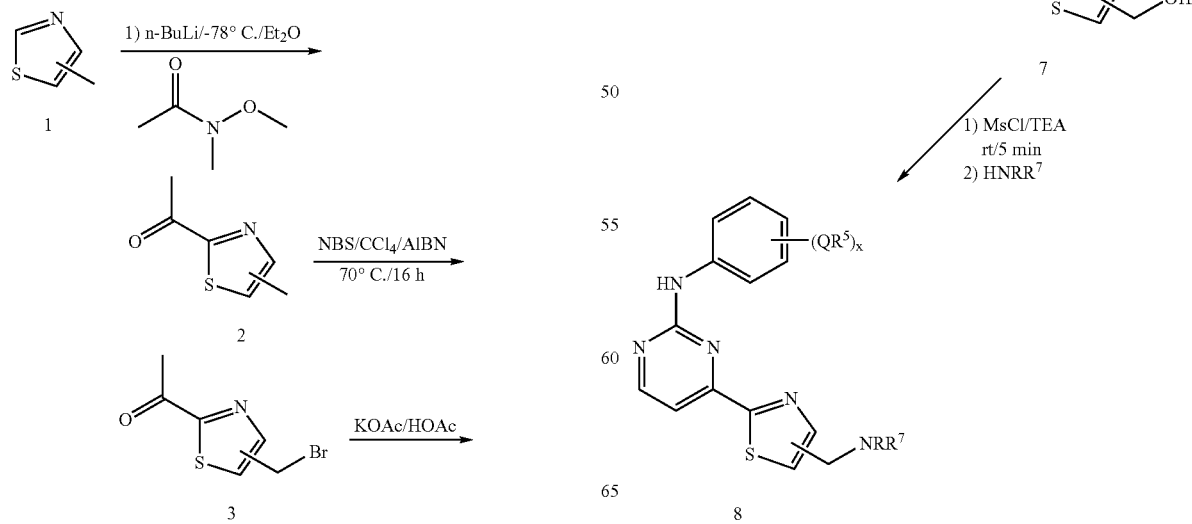

Scheme IV below depicts the synthesis of exemplary compounds where $R^3$ is CN or $CH_2Br$.
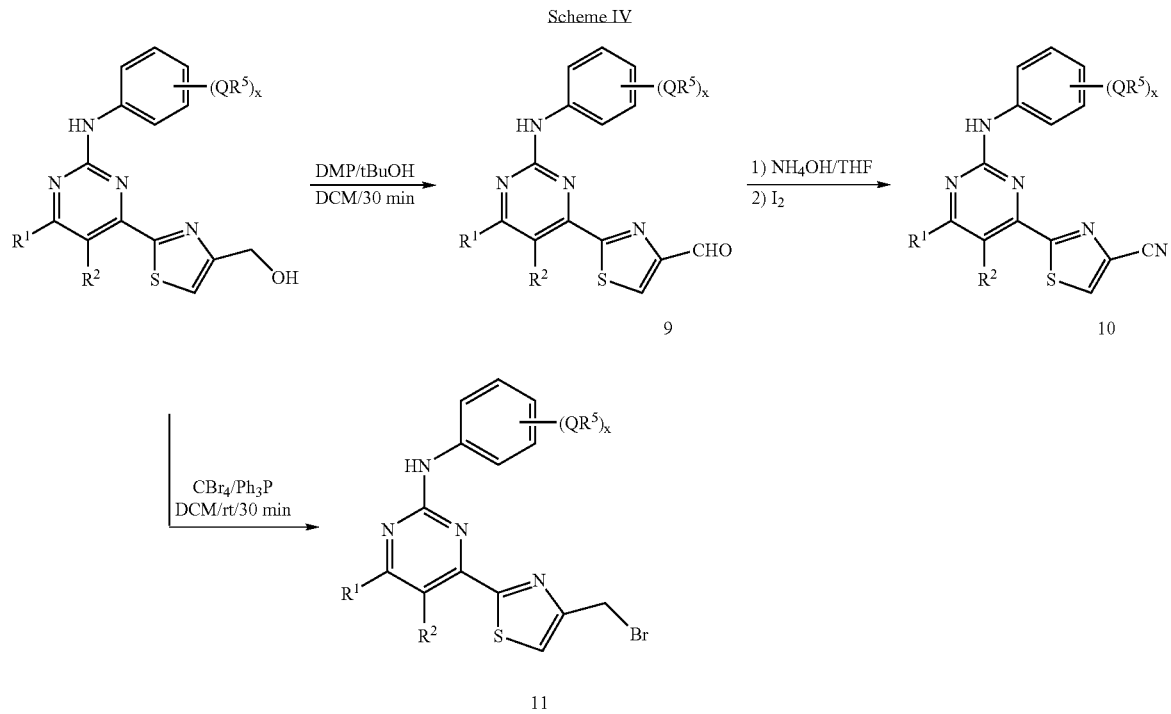
Scheme V depicts the synthesis of exemplary compounds where $R^3$ is $CH_2OMe$ or $CH_2CN$.
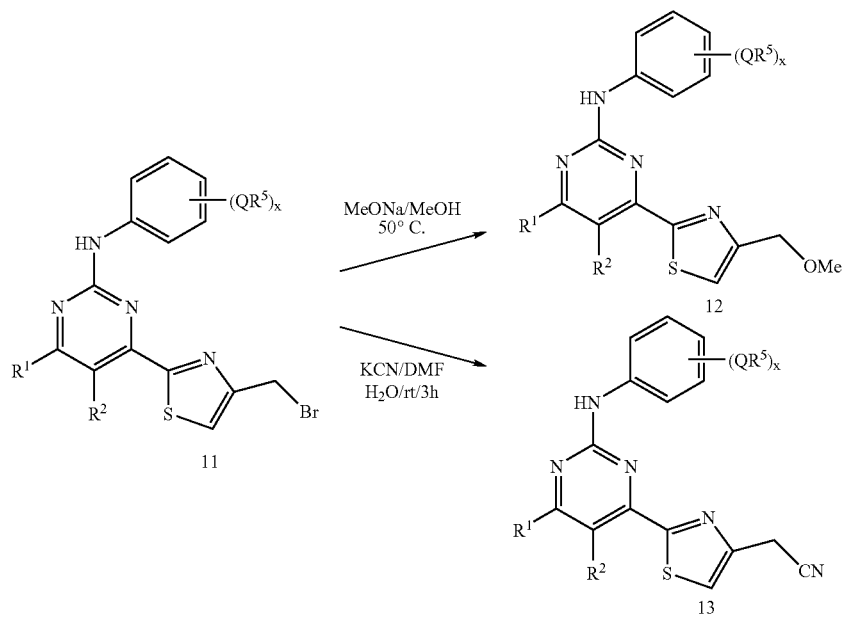

Scheme VI depicts the synthesis of exemplary compounds where $R^3$ is $CH_2COOH$.

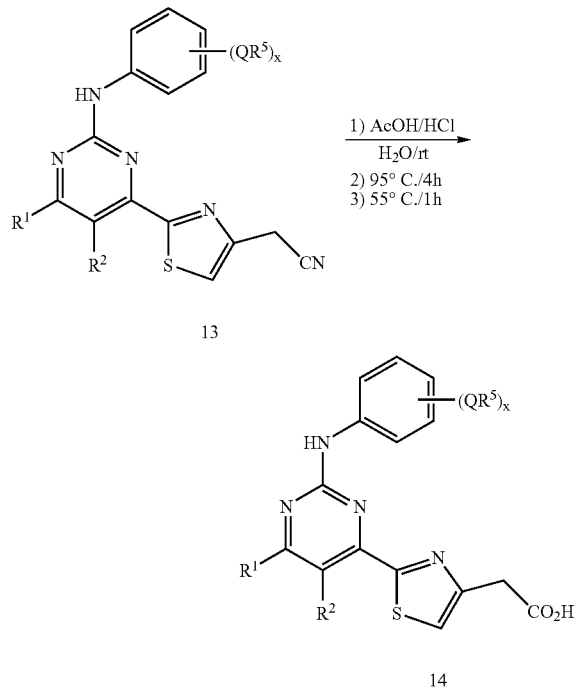

Scheme VII below depicts the synthesis of exemplary compounds where both $R^3$ and $R^4$ are substituted (as depicted, where $R^3$ is Me and $R^4$ is $(CH_2)_2OH$).

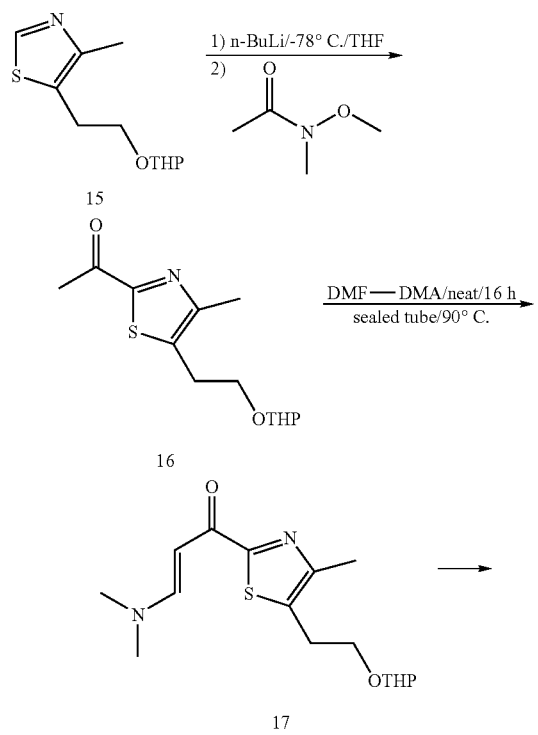

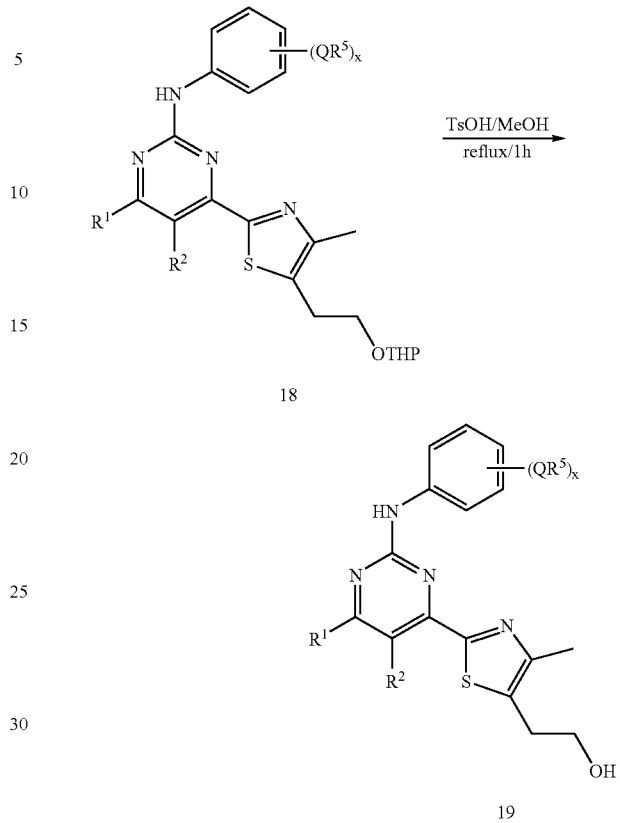

Schemes VIII and IX below depict the synthesis of exemplary compounds where both $R^3$ and $R^4$ are substituted (as shown, where both $R^3$ and $R^4$ are methyl).

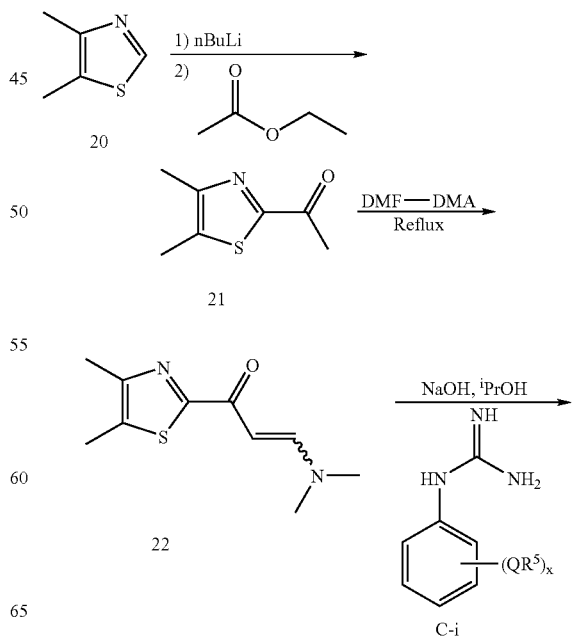

Schemes X, and XI below depict the synthesis of exemplary compounds where one of $R^3$ or $R^4$ is hydrogen and the other of $R^3$ or $R^4$ is $NRR^7$. For both Schemes X and XI reaction conditions are as follows: (a) n-BuLi, ethylacetate; (b) PTSA, HC(OMe)$_3$, MeOH; (c) n-BuLi, CCl4; (d) TFA, DCM; (e) DMF.DMA; (f) EPA, NaOH; (g) piperazine, DMSO; (h) ethylene diamine; (i) n-BuLi, CBr$_4$.
Scheme X
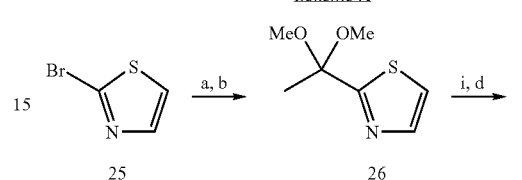
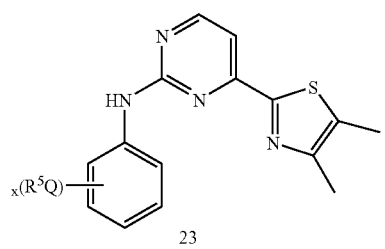
Scheme IX
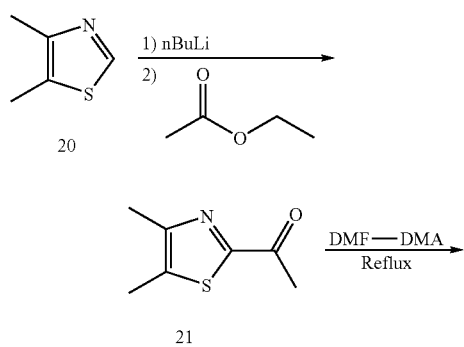
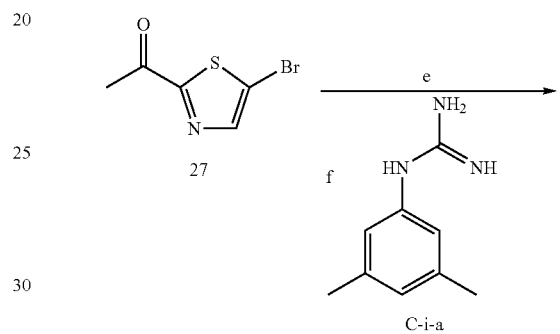
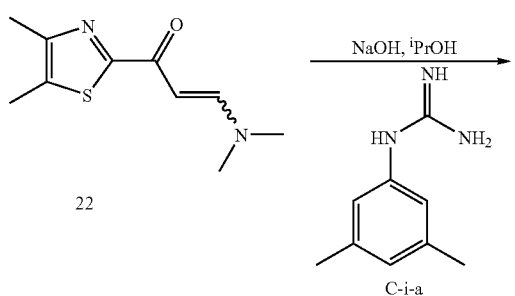
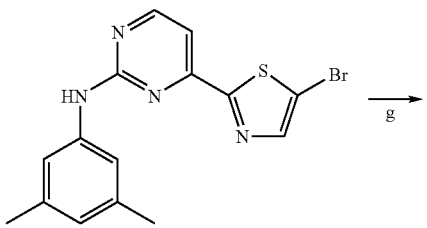
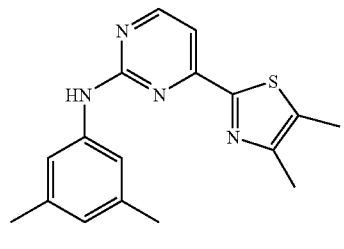
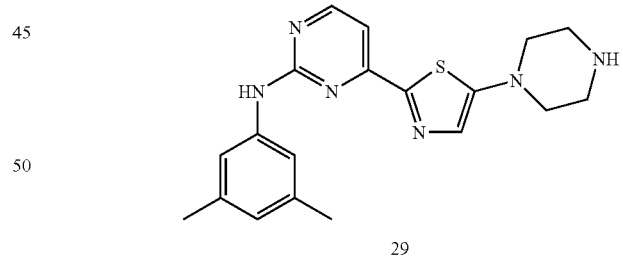
Scheme XI:
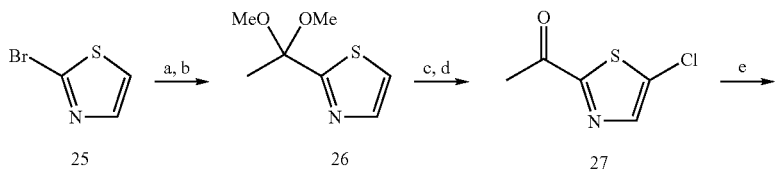

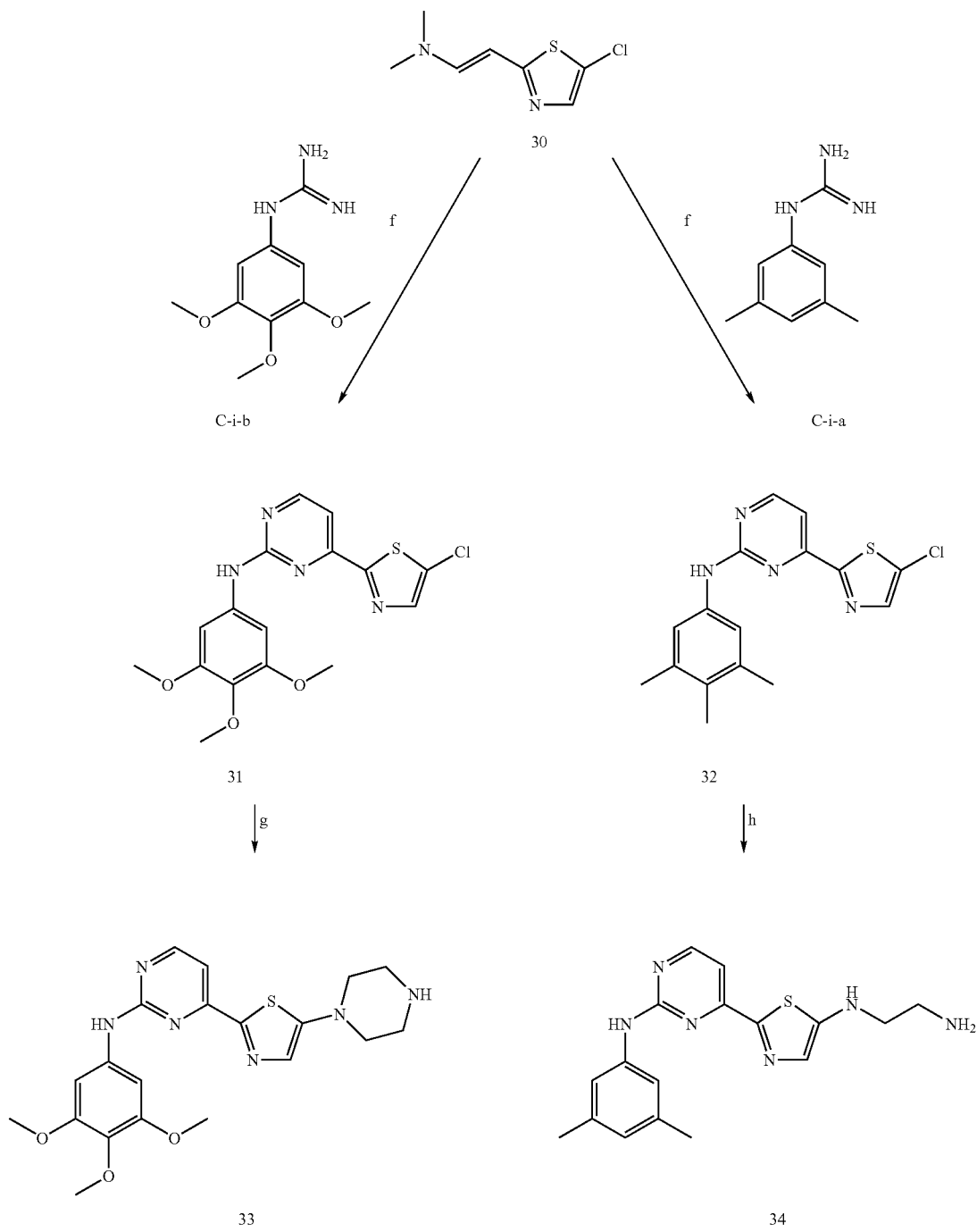

Schemes XII, and XIII below depict the synthesis of exemplary compounds where $R^3$ and $R^4$ are taken together to form an optionally substituted saturated, partially unsaturated, or Fully unsaturated 3-8-membered ring having 0-3 heteroatoms independently selected from nitrogen, oxygen, or sulfur. In certain exemplary embodiments, as depicted below, $R^3$ and $R^4$ are taken together to form an optionally substituted phenyl ring.

Scheme XII

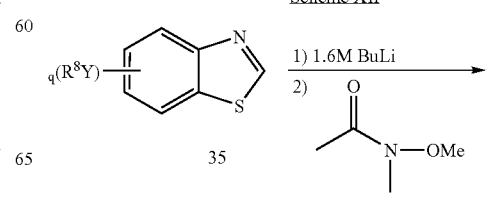

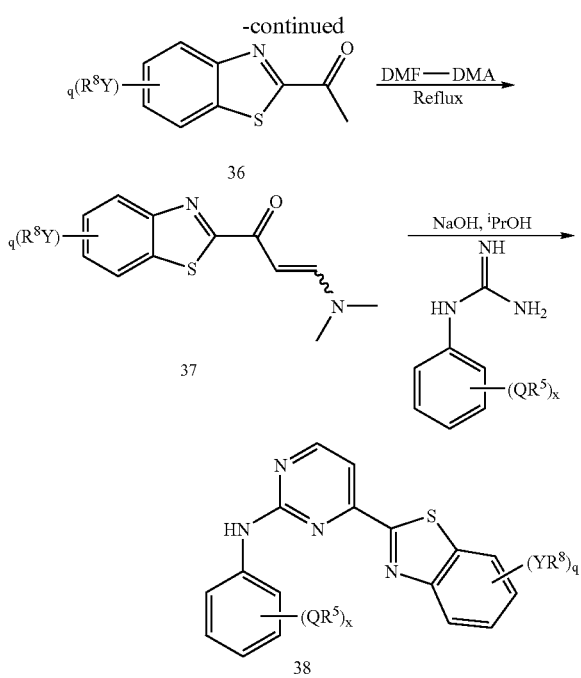

Scheme XIII:

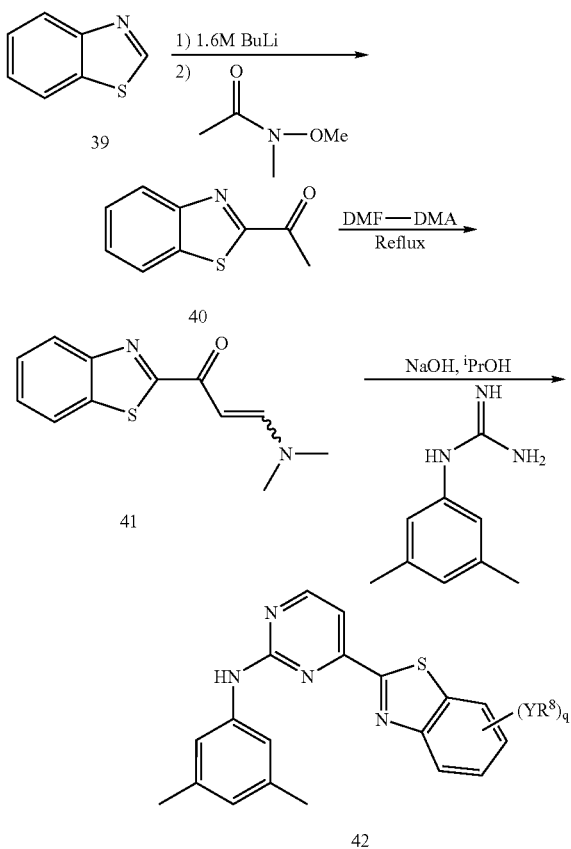

Although certain exemplary embodiments are depicted and described above and herein, it will be appreciated that additional compounds of the invention can be prepared according to the methods described generally above using appropriate starting materials by methods generally available to one of ordinary skill in the art.

5. Uses, Formulation and Administration

Pharmaceutically Acceptable Compositions

As discussed above, the present invention provides compounds that are inhibitors of protein kinases, and thus the present compounds are useful for the treatment of diseases, disorders, and conditions including, but not limited to immunodeficiency disorders, inflammatory diseases, allergic diseases, autoimmune diseases, proliferative disorders, immunologically-mediated diseases, or respiratory disorders. Accordingly, in another aspect of the present invention, pharmaceutically acceptable compositions are provided, wherein these compositions comprise any of the compounds as described herein, and optionally comprise a pharmaceutically acceptable carrier, adjuvant or vehicle. In certain embodiments, these compositions optionally further comprise one or more additional therapeutic agents.

It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable salts, esters, salts of such esters, or any other adduct or derivative which upon administration to a patient in need is capable of providing, directly or indirectly, a compound as otherwise described herein, or a metabolite or residue thereof.

As used herein, the term "pharmaceutically acceptable salt" refers to those salts which are, within the scope of sound medical judgement, suitable for use in contact with the tissues of humans and lower animals without undue toxicity, irritation, allergic response and the like, and are commensurate with a reasonable benefit/risk ratio. A "pharmaceutically acceptable salt" means any non-toxic salt or salt of an ester of a compound of this invention that, upon administration to a recipient, is capable of providing, either directly or indirectly, a compound of this invention or an inhibitorily active metabolite or residue thereof. As used herein, the term "inhibitorily active metabolite or residue thereof" means that a metabolite or residue thereof is also an inhibitor of SYK or ZAP-70 kinase.

Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+$ $(C_{1-4}alkyl)_4$ salts. This invention also envisions the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Uses of Compounds and Pharmaceutically Acceptable Compositions

In yet another aspect, a method for the treatment or lessening the severity of immunodeficiency disorders, inflammatory diseases, allergic diseases, autoimmune diseases, proliferative disorders, immunologically-mediated diseases, or respiratory disorders is provided comprising administering an effective amount of a compound, or a pharmaceutically acceptable composition comprising a compound to a subject in need thereof. In certain embodiments of the present invention an "effective amount" of the compound or pharmaceutically acceptable composition is that amount effective for treating or lessening the severity of immunodeficiency disorders, inflammatory diseases, allergic diseases, autoimmune diseases, proliferative disorders, immunologically-mediated diseases, or respiratory disorders. The compounds and compositions, according to the method of the present invention, may be administered using any amount and any route of administration effective for treating or lessening the severity of immunodeficiency disorders, inflammatory diseases, allergic diseases, autoimmune diseases, proliferative disorders, immunologically-mediated diseases, or respiratory disorders. The exact amount required will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

As described generally above, the compounds of the invention are useful as inhibitors of protein kinases. In one embodiment, the compounds and compositions of the invention are inhibitors of one or more of SYK or ZAP-70, and thus, without wishing to be bound by any particular theory, the compounds and compositions are particularly useful for treating or lessening the severity of a disease, condition, or disorder where activation of one or more of SYK or ZAP-70 is implicated in the disease, condition, or disorder. When activation of SYK or ZAP-70 is implicated in a particular disease, condition, or disorder, the disease, condition, or disorder may also be referred to as "SYK or ZAP-70-mediated disease" or disease symptom. Accordingly, in another aspect, the present invention provides a method for treating or lessening the severity of a disease, condition, or disorder where activation or one or more of SYK or ZAP-70 is implicated in the disease state.

The activity of a compound utilized in this invention as an inhibitor of SYK or ZAP-70, may be assayed in vitro, in vivo or in a cell line. In vitro assays include assays that determine inhibition of either the phosphorylation activity or ATPase activity of activated SYK or ZAP-70. Alternate in vitro assays quantitate the ability of the inhibitor to bind to SYK or ZAP-70. Inhibitor binding may be measured by radiolabelling the inhibitor prior to binding, isolating the inhibitor/SYK or inhibitor/ZAP-70, complex and determining the amount of radiolabel bound. Alternatively, inhibitor binding may be determined by running a competition experiment where new inhibitors are incubated with SYK or ZAP-70 bound to known radioligands.

The term "measurably inhibit", as used herein means a measurable change in SYK or ZAP-70 activity between a sample comprising said composition and a SYK or ZAP-70 kinase and an equivalent sample comprising SYK or ZAP-70 kinase in the absence of said composition.

The term "SYK-mediated disease" or "SYK-mediated condition", as used herein, means any disease or other deleterious condition in which SYK protein kinase is known to play a role. Such conditions include, without limitation, allergic disorders, especially asthma.

The term "ZAP-70-mediated condition", as used herein means any disease or other deleterious condition in which ZAP-70 is known to play a role. Such conditions include, without limitation, autoimmune, inflammatory, proliferative, and hyperproliferative diseases and immunologically-mediated diseases including rejection of transplanted organs or tissues and Acquired Immunodeficiency Syndrome (AIDS).

For example, ZAP-70-mediated conditions include diseases of the respiratory tract including, without limitation, reversible obstructive airways diseases including asthma, such as bronchial, allergic, intrinsic, extrinsic and dust asthma, particularly chronic or inveterate asthma (e.g. late asthma airways hyper-responsiveness) and bronchitis. Additionally, ZAP-70 diseases include, without limitation, those conditions characterised by inflammation of the nasal mucus membrane, including acute rhinitis, allergic, atrophic thinitis and chronic rhinitis including rhinitis caseosa, hypertrophic rhinitis, rhinitis purulenta, rhinitis sicca and rhinitis medicamentosa; membranous rhinitis including croupous, fibrinous and pseudomembranous rhinitis and scrofoulous rhinitis, seasonal rhinitis including rhinitis nervosa (hay fever) and vasomotor rhinitis, sarcoidosis, farmer's lung and related diseases, fibroid lung and idiopathic interstitial pneumonia.

ZAP-70-mediated conditions also include diseases of the bone and joints including, without limitation, (pannus formation in) rheumatoid arthritis, seronegative spondyloarthropathis (including ankylosing spondylitis, psoriatic arthritis and Reiter's disease), Behcet's disease, Sjogren's syndrome, and systemic sclerosis.

ZAP-70-mediated conditions also include diseases and disorders of the skin, including, without limiation, psoriasis, systemic sclerosis, atopical dermatitis, contact dermatitis and other eczematous dermatitis, seborrhoetic dermatitis, Lichen planus, Pemphigus, bullous Pemphigus, epidermolysis bullosa, urticaria, angiodermas, vasculitides, erythemas, cutaneous eosinophilias, uveitis, Alopecia, greata and vernal conjunctivitis.

ZAP-70-mediated conditions also include diseases and disorders of the gastrointestinal tract, including, without limitation, Coeliac disease, proctitis, eosinophilic gastroenteritis, mastocytosis, pancreatitis, Crohn's disease, ulcerative colitis, food-related allergies which have effects remote from the gut, e.g. migraine, rhinitis and eczema.

ZAP-70-mediated conditions also include those diseases and disorders of other tissues and systemic disease, including, without limiation, multiple sclerosis, artherosclerosis, acquired immunodeficiency syndrome (AIDS), lupus erythematosus, systemic lupus, erythematosus, Hashimoto's thyroiditis, myasthenia gravis, type I diabetes, nephrotic syndrome, eosinophilia fascitis, hyper IgE syndrome, lepromatous leprosy, sezary syndrome and idiopathic thrombocytopenia purpura, restenosis following angioplasty, tumours (for example leukemia, lymphomas), artherosclerosis, and systemic lupus erythematosus.

ZAP-70-mediated conditions also include allograft rejection including, without limitation, acute and chronic allograft rejection following for example transplantation of kidney, heart, liver, lung, bone marrow, skin and cornea; and chronic graft versus host disease.

It will also be appreciated that the compounds and pharmaceutically acceptable compositions of the present invention can be employed in combination therapies, that is, the compounds and pharmaceutically acceptable compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another agent used to treat the same disorder), or they may achieve different effects (e.g., control of any adverse effects). As used herein, additional therapeutic agents that are normally administered to treat or prevent a particular disease, or condition, are known as "appropriate for the disease, or condition, being treated".

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention or pharmaceutically acceptable compositions thereof may also be incorporated into compositions for coating implantable medical devices, such as prostheses, artificial valves, vascular grafts, stents and catheters. Accordingly, the present invention, in another aspect, includes a composition for coating an implantable device comprising a compound of the present invention as described generally above, and in classes and subclasses herein, and a carrier suitable for coating said implantable device. In still another aspect, the present invention includes an implantable device coated with a composition comprising a compound of the present invention as described generally above, and in classes and subclasses herein, and a carrier suitable for coating said implantable device.

Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a kinase inhibitor. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition.

Another aspect of the invention relates to inhibiting SYK or ZAP-70 activity in a biological sample or a patient, which method comprises administering to the patient, or contacting said biological sample with a compound of formula I or a composition comprising said compound. The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of SYK or ZAP-70 kinase activity in a biological sample is useful for a variety of purposes that are known to one of skill in the art. Examples of such purposes include, but are not limited to, blood transfusion, organ-transplantation, biological specimen storage, and biological assays.

EXAMPLES

A) Synthesis of Exemplary Compounds of the Invention:

Example 1

1-(4-Methyl-thiazol-2-yl)-ethanone (2a)

To a stirred solution of n-BuLi (2M in pentane; 22.4 mL, 0.045 mol) in 70 mL of dry ether at −78° C. was added dropwise 4-methylthiazole (3.7 g, 0.037 mol) in 30 mL of ether over a period of 30 minutes. The mixture was stirred for 1 h, then N-methoxy-N-methylacetamide (4.37 mL, 0.041 mol) was added dropwise over 10 minutes. After 1 h of stirring at −78° C. the reaction mixture was washed with sat'd $NaHCO_3$ and extracted with ether. The organic layer was dried with $Na_2SO_4$ and concentrated in vacuo to give 4.38 g (85%) of 2a as an oil that was used directly for the next step. $^1$H NMR ($CDCl_3$) δ 7.2 (s, 1H), 2.75 (s, 3H), 2.5 (s, 3H).

1-(4-Bromomethyl-thiazol-2-yl)-ethanone (3a).

A solution of 2a (4.38 g, 0.031 mol), NBS (5.8 g, 0.033 mol) and 100 mg of AIBN in 40 mL of carbon tetrachloride was heated at 70° C. for 16 h. Cooled to rt and the precipitate was filtered. The solvent was concentrated in vacuo to an oil that was subjected to flash chromatography (5% ethyl acetate/95% hexanes) to give 4.95 g (72%) of the desired product 3a. $^1$H NMR ($CDCl_3$) δ 7.8 (s, 1H), 4.8 (s, 2H), 2.8 (s, 3H).

Acetic acid 2-acetyl-thiazol-4-ylmethyl ester (4a).

Bromide 3a (4.95 g, 0.0224 mol) was heated with acetic acid (50 mL) and potassium acetate (2.64 g, 0.0269 mol) at 100° C. for 16 h. Diluted with ethyl acetate and washed with water 3 times. The organic layer was dried ($Na_2SO_4$) and concentrated in vacuo to give a crude oil that was subjected to flash chromatography (20% ethyl acetate/80% hexanes) to give 2.48 g (70%) of the desired product 4a. $^1$H NMR ($CDCl_3$) δ 7.8 (s, 1H), 5.2 (s, 2H), 2.8 (s, 3H), 2.2 (s, 3H).

3-Dimethylamino-1-(4-hydroxymethyl-thiazol-2-yl)-propenone (5a).

A solution of 4a (2.48 g, 0.124 mol) in 8.3 mL of DMF-DMA was heated at 90° C. in a sealed tube for 16 h. The precipitate that formed upon cooling was collected to give 2 g (76%) of the desired enaminone 5a. $^1$H NMR ($CDCl_3$) δ 7.8 (bs, 1H), 7.2 (s, 1H), 6.1 (bs, 1H), 4.8 (s, 2H), 3.1 (s, 3H), 2.9 (s, 3H).

{2-[2-(3,5-Dimethyl-phenylamino)-pyrimidin-4-yl]-thiazol-4-yl}-methanol (7a).

Guanidine 6 (868 mg, 0.0041 mol) and enaminone 5a (1 g, 0.0061 mol) were mixed together with potassium carbonate (596 mg, 0.0011 mol) in 2 mL of DMF and heated at 90° C. in a sealed tube for 16 h. Cooled and diluted with ethyl acetate and washed several time with water (3×) and brine. The organic layer was dried ($Na_2SO_4$) and concentrated in vacuo to a solid residue that was subjected to flash chromatography (10% methanol/90% dichloromethane) to give 1.14 g (89%) of the desired pyrimidine 7. $^1$H NMR ($CDCl_3$) δ 8.4 (d, 1H), 7.9 (bs, 1H), 7.4 (d, 1H), 7.3 (s, 1H), 6.8 (s, 1H), 4.8 (s, 2H), 2.2 (6H).

Example 2

[4-(4-Alkylaminomethyl-thiazol-2-yl)-pyrimidin-2-yl]-(3,5-dimethyl-phenyl)-amine (8a)

To a solution of 7a (125 mg, 0.4 mmol) in 10 mL of anhydrous DCM was added mesyl chloride (93 uL, 1.2 mmol) followed by trietylamine. TLC showed the disapearance of 7 after 5 minutes. The reaction mixture was partitioned between DCM and water. The organic was washed with water and dried ($Na_2SO_4$) and concentrated in vacuo to an oil that was used directly for the mesylate displacement by amines. The crude mesylate was dissolved in DCM and partitioned in 5 sealed test tubes and reacted with excess of amines for 16 h. The samples were blown down to dryness and dissolved in 1 mL DMSO and purified by reverse phase prep. HPLC (Water-MeCN; 10%-90%) with 0.1% TFA to give ~30 mg of amines 8a TFA salts after lyophylization.

Example 3

2-[2-(3,5-Dimethyl-phenylamino)-pyrimidin-4-yl]-thiazole-4-carbaldehyde (9a)

To a solution of 7a (100 mg, 0.320 mmol) and 163 uL of t-butanol in 2 mL of DCM was added 163 mg of Dess_Martin periodinane reagent. The reaction mixture was stirred for 1 h after which it was quenched with sodium thiosulfate (1 mL). It was stirred until the two phase became clear. The organic layer was dried ($Na_2SO_4$) and concentrated in vacuo to give 35 mg (38%) the crude aldehyde 9a that was used directly for the next step. $^1$H NMR ($CDCl_3$) δ 10.1 (s, 1H), 8.3 (d, 1H), 8.1 (s, 1H), 7.5 (d, 1H), 7.2 (s, 2H), 6.8 (s, 1H), 2.3 (s, 6H).

2-[2-(3,5-Dimethyl-phenylamino)-pyrimidin-4-yl]-thiazole-4-carbonitrile (10a).

To a stirring solution of the crude aldehyde 9a (35 mg, 0.11 mmol) in 1 mL of ammonia water 28% solution and 0.1 mL of THF at rt was added iodine (32 mg, 0.12 mmol). The dark solution became colorless after 1 h of stirring. The reaction mixture was neutralized with 0.5 mL of a 1M aqueous solution of HCl and extracted with ether. Concentrated in vacuo and passed through a short pad of silica gel (30% ethyl acetate/70% hexanes) to give 20 mg (59%) of pure 10.

Example 4

[4-(4-Bromomethyl-thiazol-2-yl)-pyrimidin-2-yl]-(3,5-dimethyl-phenyl)-amine (11a)

Triphenylphosphine (84 mg, 0.38 mmol) in DCM was added dropwise to a solution of alcohol 7 (100 mg, 0.32 mmol) and carbon tetrabromide (127 mg, 0.38 mmol) in DCM. Afetr 20 minutes of stirring, the reaction mixture was concentrated in vacuo to a solid residue that was subjected to flash chromatography (30% ethyl acetate/70% hexanes) to give 240 mg (67%) of the desired benzylic bromide 11a.

Example 5

(3,5-Dimethyl-phenyl)-[4-(4-methoxymethyl-thiazol-2-yl)-pyrimidin-2-yl]-amine (12a)

Benzyl bromide 11a was dissolved in 0.4 mL of a 0.5 M solution of sodium methoxide in methanol and stirred 16 h at rt. Concentrated to dryness and patitionned with ethyl acetate and water. The organic layer was dried ($Na_2SO_4$) and concentrated in vacuo to a solid residue. Purified by reverse phase prep. HPLC (Water-MeCN; 10%-90%) with 0.1% TFA to give 11 mg (34%) of methoxymethyl ether 12a.

Example 6

{2-[2-(3,5-Dimethyl-phenylamino)-pyrimidin-4-yl]-thiazol-4-yl}-acetonitrile (13a)

To a solution of benzyl bromide 11a (51 mg, 0.135 mmol) in 1 mL of DMF was added potassium cyanide (9 mg, 0.135 mmol) in 0.250 mL of water. The reaction mixture was stirred at rt for 3 h. Two mL of water was added and the mixture was extracted with ethyl acetate. The organic phase was dried ($Na_2SO_4$) and concentrated in vacuo. Purified by reverse phase prep. HPLC (Water-MeCN; 10%-90%) with 0.1% TFA to give 16 mg (37%) of the benzyl cyanide 13a.

Example 7

{2-[2-(3,5-Dimethyl-phenylamino)-pyrimidin-4-yl]-thiazol-4-yl}-acetic acid (14a)

A solution of the above cyanide 13a was hydrolysed with a mixture of acetic acid and hydrochloric acid in water at 95° C. to give crude acid 14a. Purified by reverse phase prep. HPLC (Water-MeCN; 10%-90%) with 0.1% TFA to give 40 mg (39%) of the desired product.

Example 8

1-{4-Methyl-5-[2-(tetrahydro-pyran-2-yloxy)-ethyl]-thiazol-2-yl}-ethanone (16).

To a stirred solution of n-BuLi (2M in pentane; 15.24 mL, 0.0305 mol) in 70 mL of dry ether at −78° C. was added dropwise 29 (6.3 g, 0.0277 mol) in 30 mL of ether over a period of 30 minutes. The mixture was stirred for 1 h, then N-methoxy-N-methylacetamide (3.83 mL, 0.036 mol) was added dropwise over 10 minutes. After 1 h of stirring at −78° C. the reaction mixture was washed with sat'd $NaHCO_3$ and extracted with ether. The organic layer was dried with $Na_2SO_4$ and concentrated in vacuo to give 6.66 g (89%) of 16 as an oil that was used directly for the next step.

3-Dimethylamino-1-{4-methyl-5-[2-(tetrahydro-pyran-2-yloxy)-ethyl]-thiazol-2-yl}-propenone (17).

A solution of 16 (6.66 g, 0.0247 mol) in 16 mL of DMF-DMA was heated at 90° C. in a sealed tube for 16 h. The reaction mixture was concentrated under vacuum to give 8 g (100%) of the desired enaminone 17 as an orange oil.

2-{2-[2-(3,5-Dimethyl-phenylamino)-pyrimidin-4-yl]-4-methyl-thiazol-5-yl}-ethanol (19a).

Title compound was prepared from enaminone 17 and the appropriate guanidine in the usual protocol to give the desired pyrimidine 18a. Deprotection of the THP group with a catalytic amount of p-toluensulfonic acid in methanol gave, after work up, the desired alcohol 19a.

Example 9

Preparation of Disubstituted $Ar^1$ Compounds

Scheme XIV:

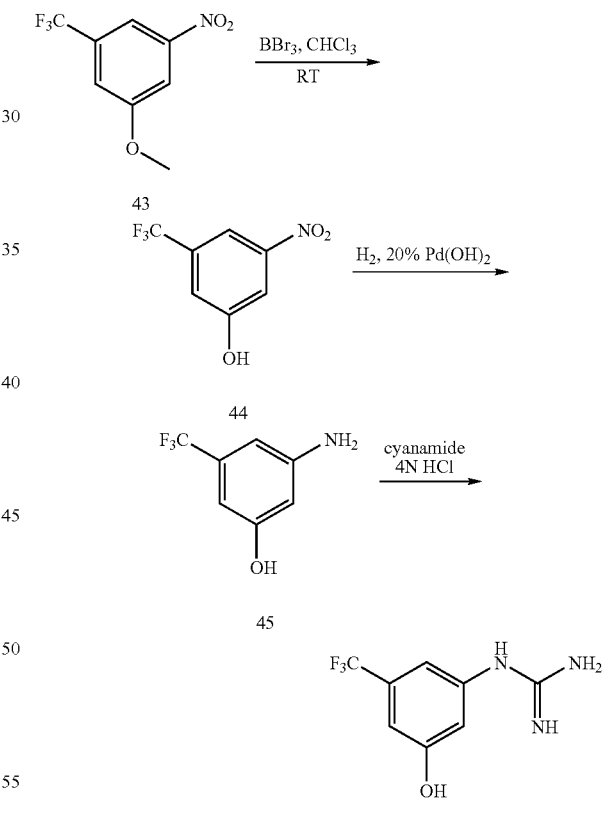

3-Nitro-5-trifluoromethyl-phenol 44: To a solution of 1-Methoxy-3-nitro-5-trifluoromethyl-benzene (3.5 g, 15.83 mmol) in 20 ml of $CHCl_3$ was added a solution of 1M boron tribromide (23.74 ml, 23.74 mmol) and the reaction was stirred at RT for 3 days resulting in conversion to product by TLC (20% EtOAc:Hexanes). The reaction was partitioned between $CH_2Cl_2$/1N NaOH and extracted. The aqueous phase was acidified with 1N HCl and again extracted with CH$_2$Cl$_2$. The organics were dried over sodium sulfate and stripped down in vacuo giving 3-Nitro-5-trifluoromethyl-phenol (1.4 g, 6.76 mmol) as a yellow oil.

3-Amino-5-trifluoromethyl-phenol 45: To a solution of 3-Nitro-5-trifluoromethyl-phenol 44 (1.6 g, 7.73 mmol) was added a catalytic amount of 20% palladium hydroxide on carbon and the reaction was stirred under a hydrogen atmosphere (balloon) over the weekend resulting in complete conversion to product by TLC (40% EtOAc:Hexanes). The reaction was filtered to give 3-Amino-5-trifluoromethyl-phenol (1.2 g, 6.76 mmol) as a brown/red oil.

N-(3-Hydroxy-5-trifluoromethyl-phenyl)-guanidine 46: A solution of 3-Amino-5-trifluoromethyl-phenol (0.21 g, 1.19 mmol), cyanamide (0.5 g, 1.19 mmol), 4N HCl in dioxane (2.975 ml, 1.199 mmol) in dioxane (10 ml) was heated in a sealed tube at 80° C. overnight resulting in complete conversion to product by TLC (10% MeOH:CH$_2$Cl$_2$). The reaction was partitioned between ethyl acetate/saturated NH$_4$Cl solution and extracted. Some product remained in the aqueous phase after multiple extractions. The crude product (0.65 g, 0.297 mmol) was sufficiently pure by LC/MS to use directly for the next step.

Subsequent reaction with the appropriate thiazolyl reagent (using conditions similar to those detailed above and herein), yields the desired disubstituted Ar$^1$ compounds. In one exemplary embodiment, a compound of formula 47 is prepared:

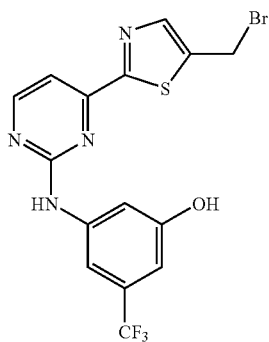

47

Example 10

[4-(5-piperazin-1-yl-thiazol-2-yl)-pyrimidin-2-yl]-(3,4,5-trimethoxy-phenyl)-amine

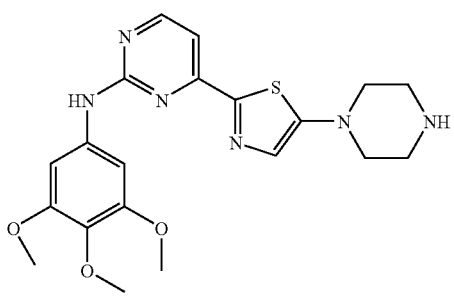

Method A:
1-Thiazol-2-yl-ethanone

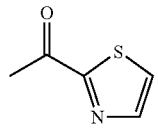

To cooled (−78° C.) diethyl ether (30 ml) was added n-butyllithium (13.2 ml of 2.5M solution in hexanes), followed by the dropwise addition of a solution of 2-bromothiazole (2.7 ml) in diethyl ether (35 ml) over 20 minutes. The resulting mixture was stirred for 30 minutes at −78° C. Under rapid stirring, ethylacetate (5 ml) was added over 2-3 minutes. The mixture was stirred for 30 minutes at −78° C., then allowed to warm to ambient and quenched with saturated sodium bicarbonate solution (50 ml). More diethyl ether (50 ml) and water (50 ml) was added. The organic phase was separated, washed with water and brine, dried with magnesium sulfate, filtered and concentrated. The residue was purified by flash chromatography (20% ethyl acetate/petroleum ether) to afford the sub-title compound as a yellow oil (3.3 g, 87%); $^1$H NMR (400 Mhz, CDCl$_3$) δ 2.7 (3H, s), 7.65 (1H, s), 8.0 (1H, s); MS (ES+) 128.1 (M+1).

Method B:
2-(1,1-Dimethoxy-ethyl)-thiazole

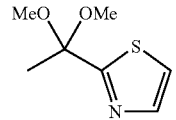

To a solution of 1-Thiazol-2-yl-ethanone (7 g) in dry methanol (100 ml) was added trimethyl orthoformate (35 ml) and p-toluenesulfonic acid (10 g) and the resulting mixture was heated at 50° C. for 12 hours. The mixture was cooled to ambient and concentrated, partitioned between saturated sodium bicarbonate and diethyl ether (100 ml). The organic phase was removed and washed with saturated sodium bicarbonate and brine, dried (magnesium sulfate), filtered and concentrated to afford the sub-title compound as crude product. The product could be further purified if necessary by flash chromatography (20% ethyl acetate/petroleum ether) to afford the sub-title compound in quantitative yield as yellow oil (9.5 g); $^1$H NMR (400 Mhz, CDCl$_3$) δ 1.75 (3H, s), 3.25 (6H, s), 7.3 (1H, s), 7.85 (1H, s); MS (ES+) 174.1 (M+1).

Method C:
5-Chloro-2-(1,1-dimethoxy-ethyl)-thiazole

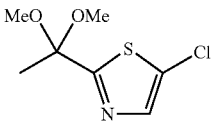

To a cooled (−78° C.) solution of 2-(1,1-Dimethoxy-ethyl)-thiazole_(4 g) in THF (60 ml) was added n-butyllithium (10 ml of 2.5M solution in hexanes) over 5 minutes. The resulting mixture was stirred for 30 minutes at −78 C, then a solution of carbon tetrachloride (10 ml) in TBF (30 ml) was added dropwise over 5 minutes. The resulting mixture was stirred for 30 minutes at −78° C., then allowed to warm up to 0° C. and quenched with saturated ammonium chloride solution. The mixture was concentrated, diluted with water (100 ml) and extracted with diethyl ether (100 ml). The organic phase was removed, washed with water and brine, dried (magnesium sulfate), filtered and concentrated. The residue was purified by flash chromatography (10% ethyl acetate/petroleum ether) to afford the sub-titled compound as a yellow solid (3.6 g, 69%); $^1$H NMR (400 Mhz, CDCl$_3$) δ 1.70 (3H, s), 3.25 (6H, s), 7.6 (1H, s).

Method D:

1-(5-Chloro-thiazol-2-yl)-ethanone

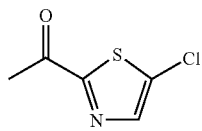

To a solution of 5-Chloro-2-(1,1-dimethoxy-ethyl)-thiazole (3.5 g) in dichloromethane (20 ml) was added trifluoroacetic acid (30 ml) and water (1 ml). The resulting mixture was stirred overnight at ambient, concentrated to an oil, diluted with diethyl ether, washed with 10% sodium bicarbonate, water and brine, dried (magnesium sulfate), filtered and concentrated to afford the sub-titled compound as a yellow solid in quantitative yield (2.6 g); $^1$H NMR (400 Mhz, CDCl$_3$) δ 2.7 (3H, s), 7.8 (1H, s).

Method E:

[2-(5-Chloro-thiazol-2-yl)-vinyl]-dimethyl-amine

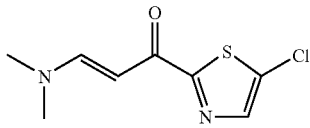

A solution of 1-(5-Chloro-thiazol-2-yl)-ethanone (2.5 g) in N,N'-dimethylformamide dimethyl acetal was refluxed for 6 hours. The mixture was allowed to cool down and concentrated to a solid. The residue was purified by flash chromatography (100% ethyl acetate) to afford the sub-titled compound as an orange solid (1.5 g, 47%); $^1$H NMR (400 Mhz, CDCl$_3$) δ 3.0 (3H, s), 3.2 (3H, s), 6.0 (1H, br d), 7.7 (1H, s), 7.9 (1H, br d); MS (ES+) 217.1 (M+1).

Method F:

[4-(5-Chloro-thiazol-2-yl)-pyrimidin-2-yl]-(3,4,5-trimethoxy-phenyl)-amine

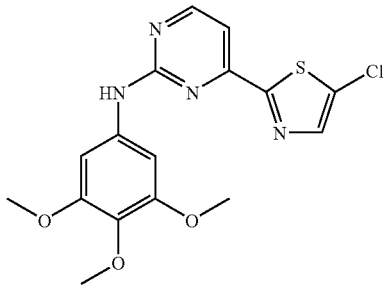

To a solution of [2-(5-Chloro-thiazol-2-yl)-vinyl]-dimethyl-amine (450 mg) in isopropanol (10 ml) was added N-(3,4,5 trimethoxyphenyl)guanidinium nitrate (560 mg) (prepared using a procedure similar to that described in WO9719065) and sodium hydroxide (80 mg). The resulting mixture was heated to reflux for 6 hours, then cooled to ambient and concentrated. The mixture was diluted with water (20 ml) and extracted with ethylacetate (20 ml), the organic phase was removed, washed with water, brine, dried (magnesium sulfate) and concentrated. The residue was purified by flash chromatography (30% ethylacetate/petroleum ether) to afford the sub-titled compound as an orange solid (260 mg, 35%); IR (solid) 1570, 1508, 1453, 1422 cm$^{-1}$; $^1$H NMR (400 Mhz, CDCl$_S$) δ 3.8 (3H, s), 3.95 (6H, s), 7.15 (1H, s), 7.50 (1H, m), 7.75 (1H, s), 8.6 (1H, d); MS (ES+) 379.2 (M+1), (ES−) 377.2 (M−1).

Method G

[4-(5-piperazin-1-yl-thiazol-2-yl)-pyrimidin-2-yl]-(3,4,5-trimethoxy-phenyl)-amine

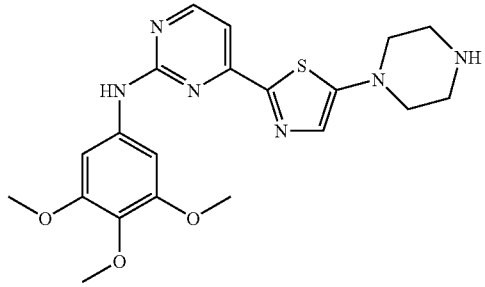

To solution of [4-(5-Chloro-thiazol-2-yl)-pyrimidin-2-yl]-(3,4,5-trimethoxy-phenyl)-amine (150 mg) in dimethylsulfoxide (2 ml) was added piperazine (300 mg). The mixture was heated to 100° C. for 5 hours then allowed to cool and concentrated under high vacuum to an oil. The residue was purified by HPLC with 0.1% TFA/water acetonitrile as eluant to afford the sub-titled compound as an yellow solid (40 mg, 25%); IR (solid) 1567, 1504, 1432, 1411 cm$^{-1}$; $^1$H NMR (400 Mhz, CDCl$_3$) δ 1.3-1.5 (1H, br s), 3.1 (4H, s), 3.25 (4H, s), 3.85 (3H, s), 3.95 (6H, s), 7.05 (1H, s), 7.15 (1H, s), 7.19 (1H, s), 7.40 (1H, m), 8.6 (1H, d); MS (ES+) 429.3 (M+1), (ES−) 427.3 (M−1).

Example 11

N'{2-[2-(3,5-Dimethyl-phenylamino)-pyrimidin-4-yl]-thiazol-5-yl}-ethane-1,2-diamine

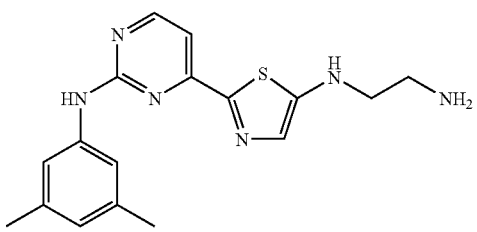

This compound was prepared using procedures similar to those described in methods A-G. N-(3,5 dimethylphenyl) guanidinium nitrate was prepared using a procedure similar to that described in WO9719065. The product was isolated as a yellow solid after purification by HPLC with 0.1% TFA/water acetonitrile as eluant (35 mg, 45% last step); IR (solid) 1622, 1565, 1455, 1332 cm$^{-1}$; $^1$H NMR (400 Mhz, CDCl₃) δ 1.3 (2H, br s), 2.5 (6H, s), 3.0 (2H, s), 3.55 (2H, s), 6.7-6.8 (2H, m), 7.25 (1H, s), 7.35 (1H, s), 7.55 (1H, d), 8.35 (1H, s), 8.55 (1H, d); MS (ES+) 341.3 (M+1), (ES−) 339.3 (M−1).

Example 12

[4-(5-piperazin-1-yl-thiazol-2-yl)-pyrimidin-2-yl]-(3,5 dimethyl-phenyl)-amine

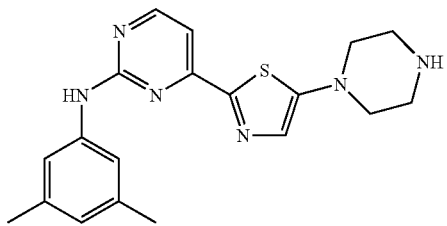

Method H:
5-Bromo-2-(1,1-dimethoxy-ethyl)-thiazole

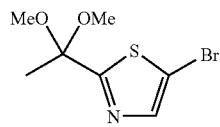

To a cooled (−78° C.) solution of 2-(1,1-Dimethoxy-ethyl)-thiazole (5.5 g) in THF (100 ml) was added n-butyl-lithium (10 ml of 2.5M solution in hexanes) over 5 minutes. The resulting mixture was stirred for 30 minutes at −78° C., then a solution of carbon tetrabromide (11 g) in THF (40 ml) was added dropwise over 5 minutes. The resulting mixture was stirred for 30 minutes at −78° C., then allowed to warm up to 0° C. and quenched with saturated ammonium chloride solution. The mixture was concentrated to remove the THF, diluted with water (100 ml) and extracted with diethyl ether (100 ml). The organic phase was removed, washed with water and brine, dried (magnesium sulfate), filtered and concentrated. The residue was purified by flash chromatography (5% ethyl acetate/petroleum ether) to afford the sub-titled compound as a orange oil (5.7 g, 71%); ¹H NMR (400 Mhz, CDCl₃) δ 1.70 (3H, s), 3.25 (6H, s), 7.7 (1H, s); MS (ES+) 252 (MBr⁷⁹+1), 222 (M-31, OCH₃).

1-(5-Bromo-thiazol-2-yl)-ethanone

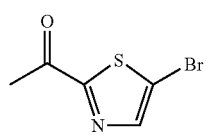

This compound was prepared using a procedure similar to that described in method D. The product was isolated as a yellow solid (100% last step); ¹H NMR (400 Mhz, CDCl₃) δ 2.7 (6H, s), 7.9 (1H, s).

[4-(5-piperazin-1-yl-thiazol-2-yl)-pyrimidin-2-yl]-(3,5 dimethyl-phenyl)-amine

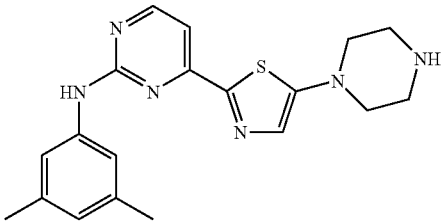

This compound was prepared from 1-(5-Bromo-thiazol-2-yl)-ethanone (prepared as described above) and N-(3,5 dimethylphenyl) guanidinium nitrate (prepared using a procedure similar to that described in WO9719065) using procedures similar to those described in methods E-G. The product was isolated as a yellow solid (31% last step); ¹H NMR (400 Mhz, CDCl₃) 2.35 (6H, s), 3.05 (4H, s), 3.25 (4H, s), 6.75 (1H, s), 7.05 (1H, s), 7.37 (3H, m), 8.45 (1H, d), 8.55 (1H, d); MS (ES+) 367.3 (M+1), (ES−) 365.3 (M−1).

Example 13

(3,5-Dimethyl-phenyl)-[4-(5-piperidin-1-yl-thiazol-2-yl)-pyrimidin-2-yl]-amine

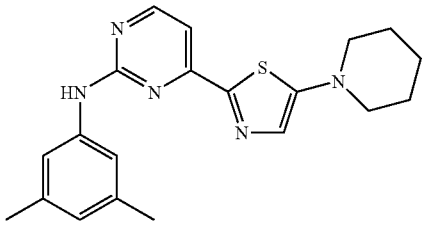

Method I
1-(5-Piperidin-1-yl-thiazol-2-yl)-ethanone

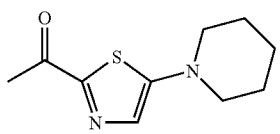

To a solution of 1-(5-Bromo-thiazol-2-yl)-ethanone (prepared as described above) (250 mg) in dimethylsulfoxide (3 ml) was added piperidine (0.3 ml). The mixture was heated to 50° C. overnight, concentrated to an oil and the residue was purified by flash chromatography (30% ethylacetate/petroleum ether) to afford the sub-titled compound as an yellow solid (170 mg, 68%); ¹H NMR (400 Mhz, CDCl₃) δ 1.6-1.8 (6H, m), 2.6 (3H, s), 3.25-3.35 (4H, m), 7.05 (1H, s); MS (ES+) 211.1 (M+1).

131

(3,5-Dimethyl-phenyl)-[4-(5-piperidin-1-yl-thiazol-2-yl)-pyrimidin-2-yl]-amine

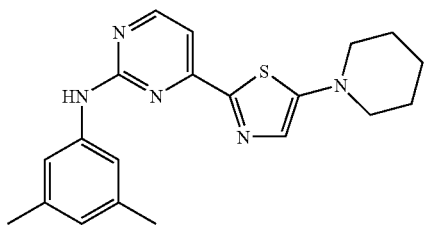

This compound was prepared from 1-(5-Piperidin-1-yl-thiazol-2-yl)-ethanone (prepared as described in method I) and N-(3,5 dimethylphenyl) guanidinium nitrate (prepared using a procedure similar to that described in WO9719065) using procedures similar to those described in methods E-F. The product was isolated as a yellow solid (40% last step); IR (solid) 1561, 1474, 1407, 1244 cm$^{-1}$; $^1$H NMR (400 Mhz, CDCl$_3$) δ 1.6-1.7 (2H, m), 1.7-1.8 (4H, s), 2.4 (6H, s), 3.25-3.35 (4H, s), 6.75 (1H, s), 7.05 (1H, s), 7.1 (1H, s), 7.4 (2H, s), 7.5 (1H, m), 8.45 (1H, s); MS (ES+) 366.3 (M+1), (ES−) 364.3 (M−1).

Example 14

[4-(5-Dimethylamino-thiazol-2-yl)-pyrimidin-2-yl]-(3,5-dimethyl-phenyl)-amine

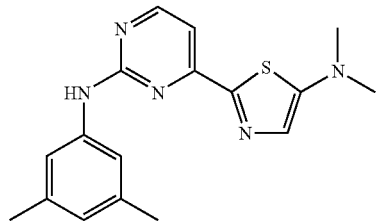

This compound was prepared from 1-(5-Dimethylamino-thiazol-2-yl)-ethanone (prepared from dimethylamine and 1-(5-Bromo-thiazol-2-yl)-ethanone in a procedure similar to that described in method I) and N-(3,5 dimethylphenyl) guanidinium nitrate (prepared using a procedure similar to that described in WO9719065) using procedures similar to those described in methods E-F. The product was isolated as a yellow solid (40% last step); IR (solid) 1738, 1365, 1217, cm$^{-1}$; $^1$H NMR (400 Mhz, CDCl$_3$) δ 2.35 (6H, s), 3.1 (6H, s), 6.75 (1H, s), 7.00 (1H, s), 7.37 (1H, s), 7.4 (2H, s), 8.45 (1H, d);); MS (ES+) 326.2 (M+1), (ES−) 324.2 (M−1).

Example 15

(4-Benzothiazol-2-yl-pyrimidin-2-yl)-(3,5-dimethyl-phenyl)-amine

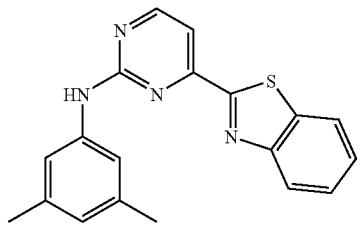

Method A:

1-Benzothiazol-2-yl-ethanone

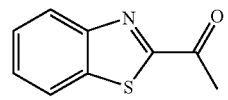

Butyllithium (10.2 mL, 16.3 mmol, 1.6 M, 1.1 Eq) was added dropwise to a stirred solution of benzothiazole (1.6 mL, 14.8 mmol, 1.0 Eq) in anhydrous THF (15 mL) at −78° C. under nitrogen. The resultant solution was stirred at −78° C. for one hour. N-Methoxy-N-methylacetamide (1.7 mL, 16.3 mmol, 1.1 Eq) was added in one portion and the reaction stirred at −78° C. for 3 hours. The resultant solution was allowed to warm to room temperature overnight. The reaction was quenched by the addition of 1M HCl (10 mL) and extracted with ethyl acetate (3×15 mL). The combined organic extracts were dried over solid MgSO$_4$ and filtered. The filtrate was concentrated under reduced pressure and purified by column chromatography (10% ethyl acetate in hexanes) to give the title compound as a yellow solid (1.0 g, 39% yield): $^1$H NMR (400 Mhz, CDCl$_3$) δ 2.85 (3H, s), 7.54-7.62 (2H, m), 8.01 (1H, d), 8.21 (1H, d); MS: ES+ 178.0 (100%).

Method B:

1-Benzothiazol-2-yl-3-dimethylamino-propenone

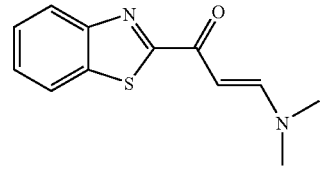

A solution of 1-Benzothiazol-2-yl-ethanone (1.0 g, 5.7 mmol, 1.0 Eq.) and dimethylformamide-dimethylacetal (2.4 mL, 17.7 mmol, 3.1 Eq.) in anhydrous THF (4 mL) was heated at reflux overnight. The resultant red solution was cooled to room temperature and the solvent removed in vacuo to give the title compound as a red solid (1.3 g, 98% yield) that was used without further purification: $^1$H NMR (400 Mhz, CDCl$_3$) δ 3.07 (3H, s), 3.25 (3H, s), 6.37 (1H, br d), 7.42-7.55 (2H, m), 7.99 (1H, d), 8.12 (1H, d); MS: ES+ 233.1 (100%).

Method C:
(4-Benzothiazol-2-yl-pyrimidin-2-yl)-(3,5-dimethyl-phenyl)-amine

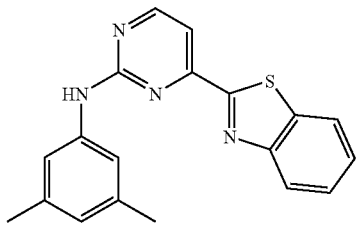

1-Benzothiazol-2-yl-3-dimethylamino-propenone (348 mg, 1.5 mmol, 1 eq.), 3,5-dimethylphenylguanidine nitrate (prepared using a procedure similar to that described in WO9719065) (339 mg, 1.5 mmol, 1 eq.) and sodium hydroxide (66 mg, 1.65 mmol, 1.1 eq.) were suspended in isopropanol (15 mL) and the mixture was stirred at reflux overnight. The resulting dark suspension was allowed to cool to room temperature and diluted with water (10 mL). The solid precipitate was isolated by filtration and washed sequentially with water (2×5 mL), isopropanol (2×5 mL) and pentane (2×5 mL) and then dried for 3 hours at 40C to give yellow solid (351 mg, 70% yield): Mp 217-219° C.; $^1$H NMR (400 Mhz, CDCl$_3$) δ 2.31 (6H, s), 6.68 (1H, s), 7.51-7.64 (5H, m), 8.26 (1H, d), 8.27 (1H, d), 9.86 (1H, br s); IR (solid): 16.29.0, 15.67.6, 1444.7 cm$^{-1}$; MS: ES+ 333.18 (100%), ES−331.20 (50%), 165.04 (100%).

Example 16

2-(3,5-dimethylanilino)-4-(4,5-dimethylthiazolo)-pyrimidine

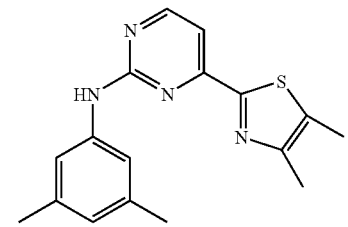

Method D:
2-Acetyl-4,5-dimethylthiazole

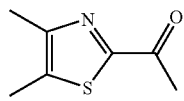

A solution of 4,5-dimethylthiazole (2.0 g, 17.67 mmol, 1 eq.) in dry diethyl ether (20 mL) was added slowly dropwise, over approximately 30 minutes, to a solution of butyllithium (7.8 mL, 19.44 mmol, 2.5M, 1.1 eq.) in dry diethyl ether (20 mL) at −70° C. The resultant solution was stirred at −70° C. for 30 minutes, −30° C. for 20 minutes and then re-cooled to −70° C. Dry ethyl acetate (3.11 g, 3.5 mL, 35.34 mmol, 2 eq.) was added in one portion to the deep red solution and the cooling bath was removed. After 50 minutes stirring at room temperature the reaction mixture was poured into saturated NaHSO$_4$ and extracted with ethyl acetate (3×50 mL). The combined organic extracts were washed with saturated Na$_2$CO$_3$ (1×50 mL), brine (1×50 mL), dried over solid Na$_2$SO$_4$ and filtered. The filtrate was concentrated under reduced pressure and the resultant greenish, mobile oil was purified by column chromatography (15% ethyl acetate in hexanes) on silica gel giving a yellow oil (1.81 g, 66% yield): $^1$H (400 Mhz, CDCl$_3$) δ 2.4(3H, s), 2.5(3H, s), 2.7(3H, s).

2-(3,5-dimethylanilino)-4-(4,5-dimethylthiazolo)-pyrimidine

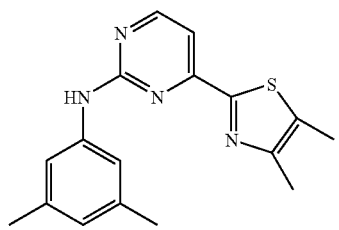

This compound was prepared using method D and procedures similar to those described in methods B-C. The product was obtained as an orange solid (183.9 mg, 62% yield): Mp. 177-179° C.; $^1$H (400 Mhz, DMSO) δ 2.3(6H, s), 2.4(3H, s), 2.45(3H, s), 6.6-6.7(1H, s), 7.3-7.4(1H, m), 7.5(2H, s), 8.6(1H, m), 9.6-9.7(1H, s); IR (solid): 1532.1, 1532.9, 1568.1, 1586.0, 1615.1 cm$^{-1}$; MS: ES$^+$ 311.1(100%), 312.1(50%), 313.1(20%), ES$^−$ 309.(30%).

Example 17

Methyl Substituted Thiazoles

2-Chloro-4-(5-methyl-2'thiazolyl)pyrimidine:

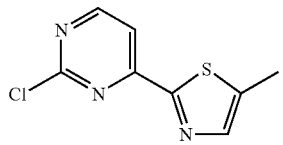

To a cooled (−78° C.) solution of nBuLi (2.5M hexanes, 4.1 ml) in diethyl ether (10 ml) was added a solution of 5-methylthiazole (1 g) in diethyl ether (10 ml) dropwise over 30 minutes. The resulting mixture was stirred for 30 minutes, then warmed to −30° C. and stirred for an additional 15 minutes. A solution of 2-chloropyrimidine (1.1 g) in diethyl ether (25 ml) was then added dropwise. The solution was stirred at −30° C. for 30 minutes, then warmed to 0° C. and stirred until the reaction was complete. Water (0.2 ml) in TBF (2.5 ml) was then added followed by DDQ (2.27 g) in THF (10 ml) and the mixture stirred at 0° C. for 15 minutes. 3M sodium hydroxide (10 ml) was then added and the mixture stirred for an additional 5 minutes.

The mixture was then diluted with ethyl acetate and the organic phase removed. The aqueous phase was further extracted with ethyl acetate. The combined organic phases were washed with water, then brine, dried (magnesium sulfate), filtered and concentrated to give a crude product. This was further purified by triturating with hexanes. The title compound was obtained as a solid (1 g, 47% yield); $^1$H NMR (400 Mhz, CDCl$_3$) δ 2.61 (3H, s), 7.70 (1H, s), 8.00 (1H, d), 8.69 (1H, d).

General procedure for the reaction of 2-Chloro-4-(5-methyl-2'thiazolyl)pyrimidine with amines.

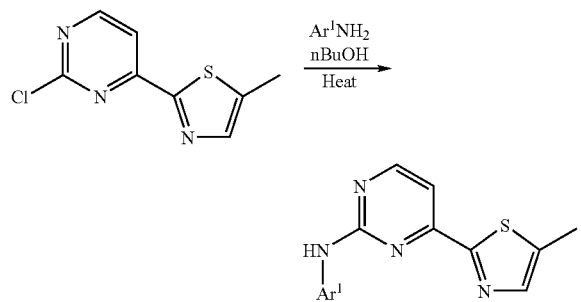

A mixture of 2-Chloro-4-(5-methyl-2'thiazolyl)pyrimidine (100 mg) and the appropriate amine (3 equivalents) in n-butanol (5 ml) was heated at 85° C. for 18-24 hours. The mixture was then cooled to ambient. The mixture was then concentrated and the crude dissolved in dichloromethane. The organic solution was washed with saturated sodium hydrogen carbonate, dried (magnesium sulfate), filtered and concentrated. The product was obtained by triturating with hexanes. Further purification by preparative HPLC was carried out if required.

TABLE 2

Exemplary NMR data for certain compounds of the invention (compound numbers refer to those numbers depicted in Table 1) are depicted below in Table 2:

| Compound Number | H$^1$ NMR |
| --- | --- |
| I-88 | H$^1$ NMR MeOD<br>8.6 d(1H), 8.1 s(1H), 7.45 d(1H), 7.4 s(2H), 6.7 s(1H), 4.6 s(2H), 4.8 m(4H), 2.3 s(6H), 1.95 m(2H), 1.85 m(2H) |
| I-87 | H$^1$ NMR MeOD<br>8.6 d(1H), 8.2 s(1H), 7.45 d(1H), 7.4 s(1H), 6.8 s(1H), 3.9 t(2H), 3.75 t(1H), 3.0 s(2H), 2.3 s (6H), 2.85 t(1H) |
| I-86 | H$^1$ NMR MeOD<br>8.6 d(1H), 8.15 s(1H), 7.45 d(1H), 7.4 s(1H), 6.7 s(1H), 5 d(1H), 4.8 d(1H), 4.8 dd(1H), 4.75 m(1H), 4.55 m(1H), 4.4 m(1H), 2.3 s(6H), 2.25 m(1H), 2.1 m(1H), 2.0 m(1H), 1.9 m(1H) |
| I-48 | H$^1$ NMR MeOD<br>8.55 d(1H), 8.2 s(1H), 8.45 d(1H), 7.35 s(2H), 6.7 s(1H), 5.75 s(2H), 3.1 m(4H), 2.35 s(6H), 2.15 m(2H), 1.35 m(2H) |
| I-46 | H$^1$ NMR MeOD<br>8.55 d(1H), 8.15 s(1H), 8.5 d(1H), 7.35 s(2H), 6.7 s(1H), 5.75 s(2H), 4.1-3.7 bs(4H), 3.5-3.3 bs(4H), 2.7 s(2H), 2.35 s(4H) |
| I-47 | H$^1$ NMR MeOD<br>8.5 d(1H), 7.9 s(1H), 7.5 d(1H), 7.35 s(2H), 6.7 s(1H)4.0 s(2H), 3.6-3.5 bs(2H), 3.2 q(2H), 3.15-3.0 bs(4H), 2.5 bs (2H), 2.35 s(6H), 1.3 t(3H) |
| I-44 | H$^1$ NMR MeOD<br>8.55 d(1H), 8.1 s(1H), 7.55 d(1H), 7.3 s(2H), 6.7 s(1H), 4.75 s(2H), 2.9 s(6H), 2.3 s(6H) |

B) Biological Data:

Example 1

SYK Inhibition Assay

Compounds were screened for their ability to inhibit SYK using a standard coupled enzyme assay (Fox et al., Protein Sci. 1998, 7, 2249). Reactions were carried out in 100 mM HEPES (pH 7.5), 10 mM MgCl$_2$, 25 mM NaCl, 1 mM DTT and 1.5% DMSO. Final substrate concentrations in the assay were 200 μM ATP (Sigma chemical Co.) and 4 μM poly Gly-Tyr peptide (Sigma Chemical Co.). Assays were carried out at 30° C. and 200 nM SYK. Final concentrations of the components of the coupled enzyme system were 2.5 mM phosphoenolpyruvate, 300 μM NADH, 30 μg/ml pyruvate kinase and 10 μg/ml lactate dehydrogenase.

An assay stock buffer solution was prepared containing all of the reagents listed above, with the exception of SYK, DTT, and the test compound of interest of the present invention. 56 μl of the test reaction was placed in a 96 well plate followed by the addition of 1 μl of 2 mM DMSO stock containing the test compound of the present invnetion (final compound concentration 30 μM). The plate was pre-incubated for ~10 minutes at 30° C. and the reaction initiated by the addition of 10 μl of enzyme (final concentration 25 nM). Rates of reaction were obtained using a BiORad Ultramark plate reader (Hercules, Calif.) over a 5 minute read time at 30° C., and K$_i$ values for the compounds of the present invention were determined according to standard methods.

Compounds of the invention are useful as inhibitors of SYK. The following compounds exhibit K$_i$ values of 5.0 μM or less: I-1, I-2, I-4, I-5, I-6, I-7, I-8, I-9, I-10, I-12, I-14, I-15, I-16, I-17, I-18, I-19, I-20, I-22, I-23, I-26, I-27, I-28, I-29, I-30, I-31, I-32, I-33, I-34, I-35, I-36, I-37, I-38, I-41, I-42, I-43, I-44, I-45, I-46, I-47, I-48, I-49, I-50, I-51, I-52, I-58, I-63, I-64, I-66, I-67, I-70, I-71, I-72, I-73, I-74, I-75, I-76, I-77, I-78, I-79, I-81, I-83, I-84, I-85, I-86, I-87, I-88, I-89, I-90, I-91, I-92, I-93, I-94, I-95, I-97, I-100, I-102, I-103, I-106, I-109, I-110, I-111, I-112, I-114, I-115, I-116, I-118, I-119, I-120, I-121, I-122, I-123, I-124, I-125, I-126, I-127, I-128, I-130, I-131, I-134, I-135, I-136, I-137, I-138, I-140, I-141, I-142, I-143, I-144, I-145, I-146, I-149, I-150, I-151, I-152, I-153, I-154, I-155, I-156, and I-157.

Example 2

ZAP-70 Inhibition Assay

Compounds were screened for their ability to inhibit ZAP-70 using a standard coupled enzyme assay (Fox et al., Protein Sci. 1998, 7, 2249). Assays were carried out in a mixture of 100 mM HEPES (pH 7.5), 10 mM MgCl$_2$, 25 mM NaCl, 2 mM DTT and 3% DMSO. Final substrate concentrations in the assay were 100 μM ATP (Sigma Chemicals) and 20 μM peptide (poly-4EY, Sigma Chemicals). Assays were carried out at 30° C. and 60 nM ZAP-70. Final concentrations of the components of the coupled enzyme system were 2.5 mM phosphoenolpyruvate, 300 μM NADH, 30 μg/ml pyruvate kinase and 10 μg/ml lactate dehydrogenase.

An assay stock buffer solution was prepared containing all of the reagents listed above, with the exception of ZAP-70 and the test compound of interest of the present invention. 55 μl of the stock solution was placed in a 96 well plate followed by addition of 2 μl of DMSO stock containing serial dilutions of the test compound of the present invention (typically starting from a final concentration of 15 μM). The plate was preincubated for 10 minutes at 30° C. and the reaction initiated by addition of 10 μl of enzyme (final concentration 60 nM). Initial reaction rates were determined with a Molecular Devices SpectraMax Plus plate reader over a 15 minute time course. $K_i$ data was calculated from non-linear regression analysis using the Prism software package (GraphPad Prism version 3.0a for Macintosh, GraphPad Software, San Diego Calif., USA).

Compounds of the invention are useful as inhibitors of ZAP-70. The following compounds exhibit $K_i$ values of 5.0 μM or less: I-1, I-2, I-4, I-5, I-6, I-7, I-8, I-9, I-10, I-12, I-14, I-15, I-16, I-17, I-18, I-19, I-20, I-22, I-23, I-26, I-27, I-28, I-29, I-30, I-31, I-32, I-34, I-35, I-36, I-37, I-38, I-41, I-42, I-43, I-44, I-45, I-46, I-47, I-48, I-49, I-50, I-51, I-52, I-63, I-64, I-66, I-70, I-71, I-72, I-73, I-74, I-75, I-76, I-77, I-78, I-79, I-81, I-83, I-84, I-85, I-86, I-87, I-88, I-89, I-90, I-91, I-92, I-93, I-94, I-95, I-97, I-100, I-102, I-103, I-106, I-109, I-110, I-111, I-112, I-114, I-115, I-116, I-118, I-119, I-120, I-121, I-122, I-123, I-124, I-125, I-127, I-128, I-130, I-131, I-134, I-135, I-136, I-137, I-138, I-140, I-141, I-142, I-143, I-144, I-145, I-146, I-149, I-150, I-152, I-153, I-154, I-155, I-156, and 1-157.

While a number of embodiments of this invention have been described, it is apparent that the basic examples described herein may be altered to provide other embodiments that utilize the compounds and methods of this invention. Therefore, it will be appreciated that the scope of this invention is to be defined by the appended claims rather than by the specific embodiments that have been represented by way of example.

The invention claimed is:

1. A compound of formula (I):

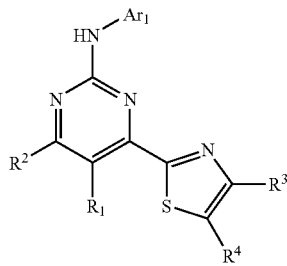

I or a pharmaceutically acceptable salt thereof, wherein:
$R^1$ and $R^2$ are each independently R, halogen, CN, $NO_2$, or TR;
T is an optionally substituted $C_1$-$C_4$ alkylidene chain wherein up to two methylene units of T are optionally and independently replaced by O, N(R), C(O), S, SO, or $SO_2$;
$Ar^1$ is

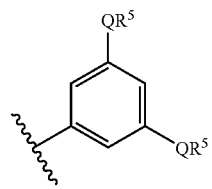

wherein each occurrence of $QR^5$ is, independently, $CH_2$halogen, halogen, $CH_2CN$, CN, $CH_2CO_2R'$, $CO_2R'$, $CH_2COR'$, COR', R', $CH_2NO_2$, $NO_2$, $CH_2OR'$, OR', $CH_2SR'$, SR', haloalkyl, $CH_2SO_2N(R')_2$, $SO_2N(R')_2$, $CH_2N(R')_2$, $N(R')_2$, NHCOR', $CH_2NHCOR'$, $CH_2PO(OR')_2$, $PO(OR')_2$;

$R^3$ and $R^4$ are each independently Z-$R^7$, or $R^3$ and $R^4$ are taken together to form an optionally substituted saturated, partially unsaturated, or fully unsaturated 3-8 membered ring having 0-3 heteroatoms independently selected from nitrogen, oxygen, or sulfur wherein said ring is optionally substituted with 0-5 independent occurrences of Y-$R^8$;

each occurrence of Q, Z, and Y is independently a bond or an optionally substituted $C_1$-$C_6$ alkylidene chain wherein up to two non-adjacent methylene units of Q and up to three non-adjacent methylene units of Z are optionally replaced by CO, $CO_2$, COCO, CONR, OCONR, NRNR, NRNRCO, NRCO, $NRCO_2$, NRCONR, SO, $SO_2$, $NRSO_2$, $SO_2NR$, $NRSO_2NR$, O, S, or NR;

each occurrence of $R^5$, $R^7$ and $R^8$ is independently R', halogen, $NO_2$, CN, OR', SR', $N(R')_2$, NR'C(O)R', NR'C(O)N(R')_2, $NR'CO_2R'$, C(O)R', $CO_2R'$, OC(O)R', C(O)N(R')2, OC(O)N(R')2, SOR', $SO_2R'$, $SO_2N(R')_2$, $NR'SO_2R'$, $NR'SO_2N(R')_2$, $PO(OR')_2$, C(O)C(O)R', or $C(O)CH_2C(O)R'$; and each occurrence of R is independently hydrogen or an optionally substituted $C_{1-6}$ aliphatic group; and each occurrence of R' is independently hydrogen or an optionally substituted group selected from $C_{1-8}$ aliphatic, $C_{6-10}$ aryl, a heteroaryl ring having 5-10 ring atoms, or a heterocyclyl ring having 3-10 ring atoms, or wherein two occurrences of R and R' taken together or two occurrences of R' taken together, form an optionally substituted saturated, partially unsaturated, or fully unsaturated 3-8 membered ring having 0-3 heteroatoms independently selected from nitrogen, oxygen, or sulfur, provided that $R^3$ and $R^4$ are not simultaneously hydrogen.

2. The compound of claim 1, wherein both occurrences of Q-$R^5$ are methyl.

3. The compound of claim 1, wherein at least one occurrence of Q-$R^5$ is $CF_3$.

4. The compound of claim 1, wherein Q-$R^5$ substituents on $Ar^1$ are fluoro, iodo, chloro, bromo, $COCH_3$, $CO_2CH_3$, $C_{1-4}$alkyl, $NH_2$, $CH_2NH_2$, NHMe, $CH_2NHMe$, $N(Me)_2$, $CH_2N(Me)_2$, $N(Et)_2$, $CH_2N(Et)_2$, NH(phenyl), $CO(C_{1-4}$alkyl), $CH_2CO(C_{1-4}$alkyl), $NHCO(C_{1-4}$alkyl), $CH_2NHCO(C_{1-4}$alkyl), CN, $CH_2CN$, OH, $C_{1-4}$alkoxy, optionally substituted benzyloxy, optionally substituted phenyloxy, $CF_3$, $SO_2NH_2$, $SO_2NHMe$, optionally substituted $SO_2$(phenyl), $SO_2(C_{,1-4}$alkyl), $CONH_{12}$, $CH_2PO(OR')_2$, or an optionally substituted group selected from a saturated, partially unsaturated, or fully unsaturated 5- or 6-membered ring having 0-3 heteroatoms independently selected from nitrogen, oxygen, or sulfur.

5. The compound of claim 1, wherein $R^1$ and $R^2$ groups of formula I are each independently hydrogen, $N(R)_2$, SR, or OR.

6. The compound of claim 1, wherein $R^1$ and $R^2$ groups are each independently hydrogen, OH, $CH_3$, $CH_2CH_3$, $OCH_3$, $CH_2OH$, $CH_2OCH_3$, $CH_2NH_2$, $CH_2NHCH_3$, $NH_2$, or $CH_2NH_2$.

7. The compound of claim 1, wherein $R^3$ and $R^4$ are each independently Z-$R^7$ wherein Z is a bond or an optionally substituted $C_{1-4}$ alkylidene chain wherein one methylene unit of Z is optionally replaced by O, NR, NRCO, $NRCO_2$, $NRSO_2$, CONR, C(O), C(O)O, and wherein $R^7$ selected from halogen, CN, $N(R')_2$, NHCOR', or R'.

8. The compound of claim 1, wherein $R^3$ and $R^4$ are each independently hydrogen, CN, halogen, OH, SH, $NH_2$, CO₂H, COH, CONH₂, SO₂NH₂, NO₂, (CH₂)$_n$NRR⁷, wherein R and R⁷, taken together with the nitrogen atom to which they are bound form an optionally substituted 3-8-membered saturated or partially unsaturated ring having 1-3 heteroatoms selected from nitrogen, oxygen, or sulfur, and n is 0, 1, 2, 3, 4, or 5.

9. The compound of claim 1, wherein one of R³ or R⁴ is hydrogen, and the other of R³ or R⁴ is (CH₂)$_n$halogen, (CH₂)$_n$CN, (CH₂)$_n$OR⁷, (CH₂)$_n$NRR⁷, (CH₂)$_n$C(O)R⁷, (CH₂)$_n$C(O)R⁷ (CH₂)$_n$CH₃, (CH₂)$_n$C(O)NRR⁷, (CH₂)$_n$SR⁷, wherein R⁷ is hydrogen, (CH₂)$_m$N(R')₂, C₁-C₄alkyl, an optionally substituted 5- or 6-membered aryl, aralkyl, heteroaryl, or heteroaralkyl group, or R and R⁷, taken together with the nitrogen atom to which they are bound form an optionally substituted 3-8-membered saturated or partially unsaturated ring having 1-3 heteroatoms selected from nitrogen, oxygen, or sulfur.

10. The compound of claim 9, wherein R³ is hydrogen.

11. The compound of claim 9, wherein R⁴ is hydrogen.

12. The compound of claim 1, wherein R³ and R⁴, taken together with the atoms to which they are bound, form an optionally substituted saturated, partially unsaturated, or fully unsaturated 5- or 6-membered ring having 0-3 heteroatoms independently selected from nitrogen, oxygen, or sulfur, and wherein said ring is optionally substituted with 0, 1, 2, 3, 4, or occurrences of Y—R⁸.

13. The compound of claim 12, wherein each occurrence of Y—R⁸ is independently methyl, ethyl, t-butyl, fluoro, chloro, bromo, oxo, CF₃, OMe, OEt, CN, SO₂Me, SO₂NH₂, NH₂, NHMe, N(Me)₂, SMe, SEt, OH, C(O)Me, NO₂, or CH₂OH.

14. The compound of claim 1, having one of formulas I-A-i, I-A-ii, I-B-i, I-B-ii, I-C-i, I-C-ii, I-D-i, or I-E-i:

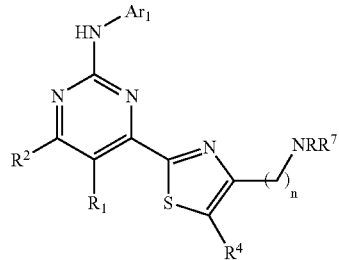

I-A-i

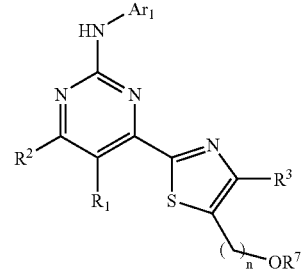

I-A-ii

I-B-i

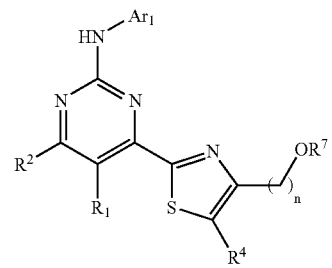

I-B-ii

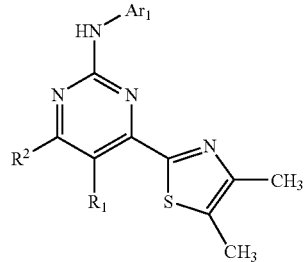

I-C-i

I-C-ii

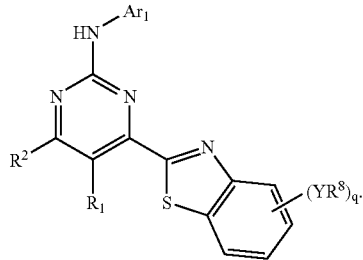

I-D-i

I-E-i wherein q is 0-5 and n is 0 or 1.

15. The compound of claim 14, wherein R³ is Z-R⁷, wherein Z is a bond or is an optionally substituted C₁₋₄ alkylidene chain wherein one methylene unit of Z is optionally replaced by O, NR, NRCO, NRCO₂, NRSO₂, CONR, C(O), C(O)O, and wherein R⁷ is halogen, CN, N(R')₂, NHCOR', or R'.

16. The compound of claim 14, wherein R³ is (CH₂)$_n$OR⁷, (CH₂)$_n$NNR⁷, (CH₂)$_n$C(O)R⁷, wherein R⁷ is hydrogen, (CH₂)$_m$N(R')₂, C₁-C₄alkyl, an optionally substituted 5- or 6-membered aryl or heteroaryl, or R and R⁷, taken together with the nitrogen atom to which they are bound form an optionally substituted 3-8-membered saturated or partially unsaturated ring having 1-3 heteroatoms selected from nitrogen, oxygen, or sulfur, wherein n is 0 or 1 and m is 0 or 1.

17. The compound of claim 14, wherein Z is a bond or is an optionally substituted $C_{1-4}$ alkylidene chain wherein one methylene unit of Z is optionally replaced by O, NR, NRCO, $NRCO_2$, $NRSO_2$, CONR, C(O), C(O)O, and wherein $R^7$ is selected from halogen, CN, N(R')$_2$, NHCOR', or R'.

18. The compound of claim 14, wherein $R^4$ is $(CH_2)_nOR^7$, $(CH_2)_nNRR^7$, $(CH_2)_nC(O)R^7$, $(CH_2)_nCH_3$, or $(CH_2)_nSR^7$, wherein $R^7$ is hydrogen, $(CH_2)_mN(R')_2$, $C_1$-$C_4$alkyl, an optionally substituted 5- or 6-membered aryl or heteroaryl or R and $R^7$, taken together with the nitrogen atom to which they are bound form an optionally substituted 3-8-membered saturated or partially unsaturated ring having 1-3 heteroatoms selected from nitrogen, oxygen, or sulfur, wherein n is 0 or 1 and m is 0 or 1.

19. The compound of claim 14, wherein q is 0, 1, or 2, and each occurrence of Y—$R^8$ is independently methyl, ethyl, t-butyl, fluoro, chloro, bromo, oxo, $CF_3$, OMe, OEt, CN, $SO_2Me$, $SO_2NH_2$, $NH_2$, NHMe, N(Me)$_2$, SMe, SEt, OH, C(O)Me, $NO_2$, or $CH_2OH$.

20. The compound of claim 14, wherein compounds have one of formulas II-A-i, II-B-i, or II-C-i, and the compound variables are defined as:
 a) x is 0, 1, 2, or 3, and Q-$R^5$ is $CH_2$halogen, halogen, $CH_2CN$, CN, $CH_2CO_2R'$, $CO_2R'$, $CH_2COR'$, COR', R', $CH_2NO_2$, $NO_2$, $CH_2OR'$, OR', $CH_2SR'$, SR', haloalkyl, $CH_2SO_2N(R')_2$, $SO_2N(R')_2$, $CH_2N(R')_2$, $N(R')_2$, NHCOR', $CH_2NHCOR'$, $CH_2PO(OR')_2$, $PO(OR')_2$, or Q-$R^5$, taken together with the atoms to which they are bound, form an optionally substituted saturated, partially unsaturated, or fully unsaturated 5-8-membered ring having 0-3 heteroatoms selected from nitrogen, oxygen, or sulfur;
 b) $R^1$ and $R^2$ are each independently hydrogen, N(R')$_2$, SR, OR, or TR, or $R^1$ and $R^2$, taken together form an optionally substituted saturated, partially unsaturated, or fully unsaturated 5-membered ring having 0-2 heteroatoms independently selected from N, O, or S; and
 c) $R^3$ is $(CH_2)_n$halogen, $(CH_2)_nCN$, $(CH_2)_nOR^7$, $(CH_2)_nNRR^7$, $(CH_2)_nC(O)R^7$, $(CH_2)_nCH_3$, $(CH_2)_nC(O)NRR^7$, $(CH_2)_nSR^7$, wherein $R^7$ is $(CH_2)_mN(R')_2$, $C_1$-$C_4$alkyl, an optionally substituted 5- or 6-membered aryl, aralkyl, heteroaryl, or heteroaralkyl group, or R and $R^7$, taken together with the nitrogen atom to which they are bound form an optionally substituted 3-8-membered saturated or partially unsaturated ring having 1-3 heteroatoms selected from nitrogen, oxygen, or sulfur, n is 0 or 1, and m is 0 or 1.

21. The compound of claim 14, wherein compounds have one of formulas II-A-ii, I-B-ii, or II-C-ii, and one or more of the compound variables are defined as:
 a) x is 0, 1, 2, or 3, and Q-$R^5$ is $CH_2$halogen, halogen, $CH_2CN$, CN, $CH_2CO_2R'$, $CO_2R'$, $CH_2COR'$, COR', R', $CH_2NO_2$, $NO_2$, $CH_2OR'$, OR', $CH_2SR'$, SR', haloalkyl, $CH_2SO_2N(R')_2$, $SO_2N(R')_2$, $CH_2N(R')_2$, $N(R')_2$, NHCOR', $CH_2NHCOR'$, $CH_2PO(OR')_2$, $PO(OR')_2$, or Q-$R^5$, taken together with the atoms to which they are bound, form an optionally substituted saturated, partially unsaturated, or fully unsaturated 5-8-membered ring having 0-3 heteroatoms selected from nitrogen, oxygen, or sulfur;
 b) $R^1$ and $R^2$ are each independently hydrogen, N(R')$_2$, SR, OR, or TR, or $R^1$ and $R^2$, taken together form an optionally substituted saturated, partially unsaturated, or fully unsaturated 5-membered ring having 0-2 heteroatoms independently selected from N, O, or S; and
 c) $R^4$ is $(CH_2)$, halogen, $(CH_2)_nCN$, $(CH_2)_nOR^7$, $(CH_2)_nNRR^7$, $(CH_2)_nC(O)R^7$, $(CH_2)_nCH_3$, $(CH_2)_nC(O)NRR^7$, $(CH_2)_nSR^7$, wherein $R^7$ is $(CH_2)_mN(R')_2$, $C_1$-$C_4$alkyl, an optionally substituted 5- or 6-membered aryl, aralkyl, heteroaryl, or heteroaralkyl group, or R and $R^7$, taken together with the nitrogen atom to which they are bound form an optionally substituted 3-8-membered saturated or partially unsaturated ring having 1-3 heteroatoms selected from nitrogen, oxygen, or sulfur, n is 0 or 1, and m is 0 or 1.

22. The compound of claim 14, wherein compounds have formula II-E-i, and one or more of the compound variables are defined as:
 a) x is 0, 1, 2, or 3, and Q-$R^5$ is $CH_2$halogen, halogen, $CH_2CN$, CN, $CH_2CO_2R'$, $CO_2R'$, $CH_2COR'$, COR', R', $CH_2NO_2$, $NO_2$, $CH_2OR'$, OR', $CH_2SR'$, SR', haloalkyl, $CH_2SO_2N(R')_2$, $SO_2N(R')_2$, $CH_2N(R')_2$, $N(R')_2$, NHCOR', $CH_2NHCOR'$, $CH_2PO(OR')_2$, $PO(OR')_2$, or Q-$R^5$, taken together with the atoms to which they are bound, form an optionally substituted saturated, partially unsaturated, or fully unsaturated 5-8-membered ring having 0-3 heteroatoms selected from nitrogen, oxygen, or sulfur;
 b) $R^1$ and $R^2$ are each independently hydrogen, N(R')$_2$, SR, OR, or TR, or $R^1$ and $R^2$, taken together form an optionally substituted saturated, partially unsaturated, or fully unsaturated 5-membered ring having 0-2 heteroatoms independently selected from N, O, or S; and
 c) q is 0, 1, or 2, and each occurrence of Y—$R^8$ is independently methyl, ethyl, t-butyl, fluoro, chloro, bromo, oxo, $CF_3$, OMe, OEt, CN, $SO_2Me$, $SO_2NH_2$, $NH_2$, NHMe, N(Me)$_2$, SMe, SEt, OH, C(O)Me, $NO_2$, or $CH_2OH$.

23. The compound of claim 1, selected from.

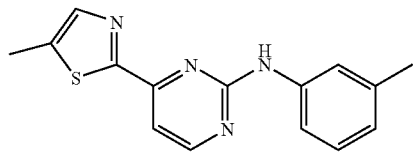

I-3

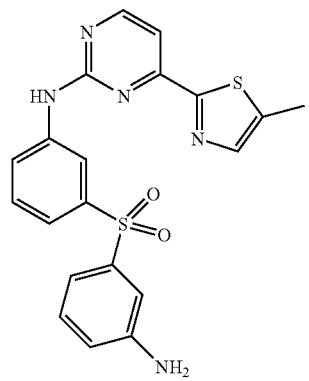

I-6

I-11
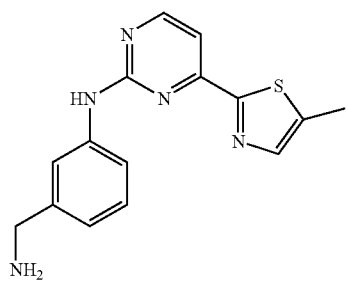
I-15
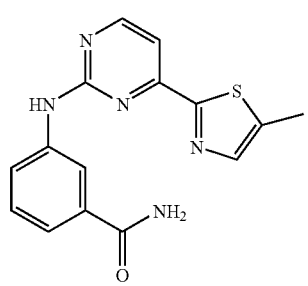
I-27
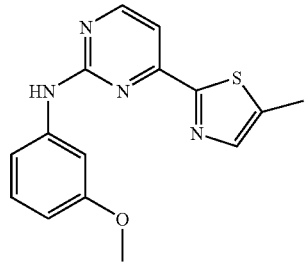
I-30
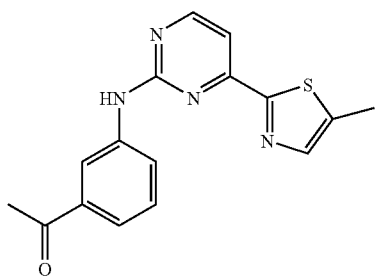
I-32
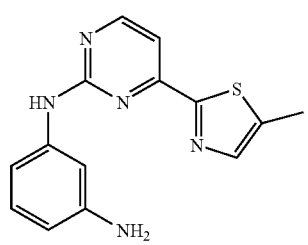
I-37
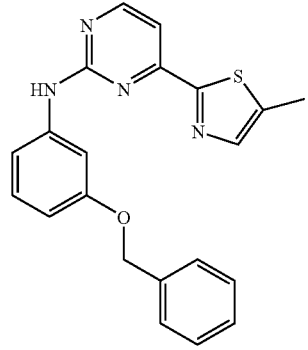
I-38
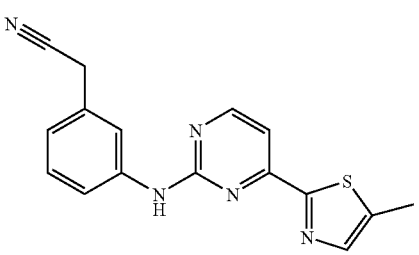
I-39
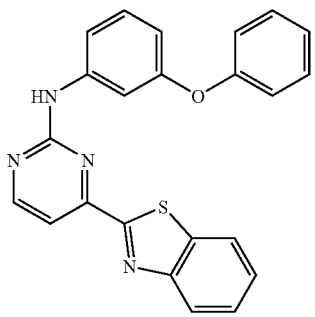
I-40
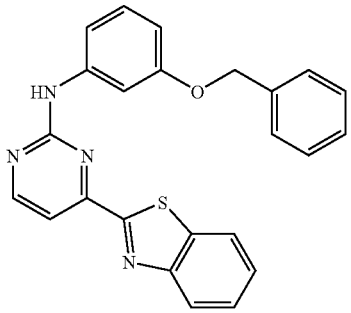
I-41
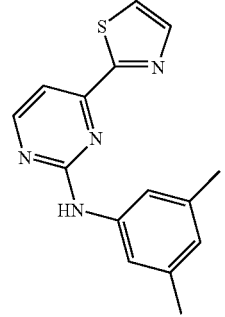

-continued
I-42
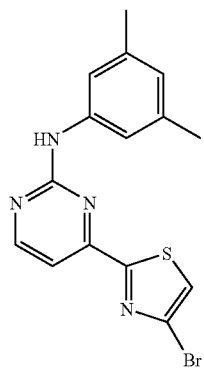
I-43
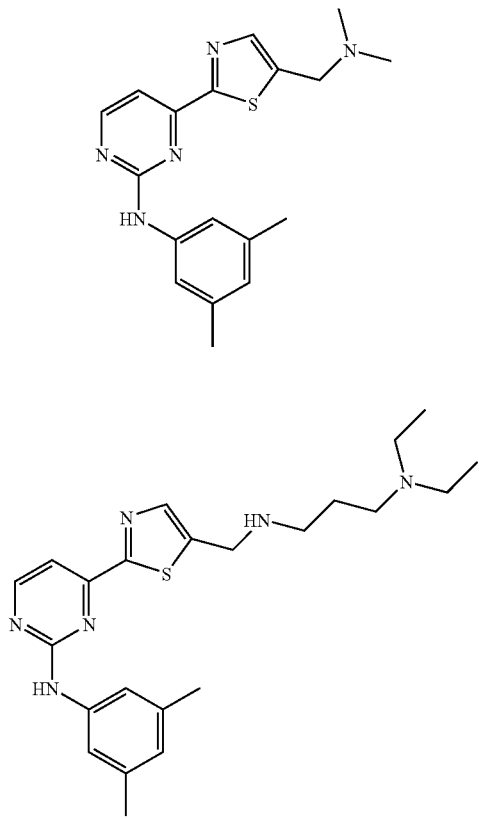
I-44
I-45
-continued
I-46
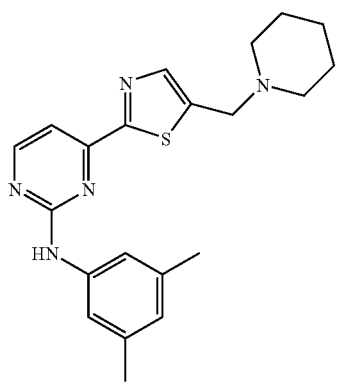
I-47
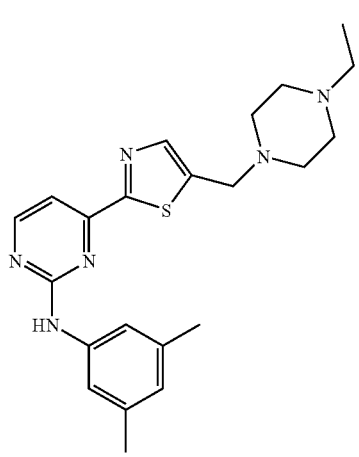
I-48
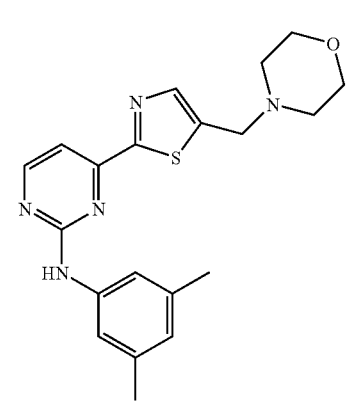
I-49
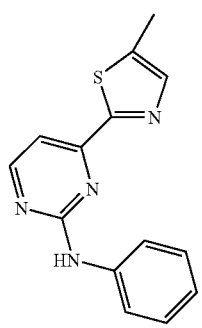

I-51
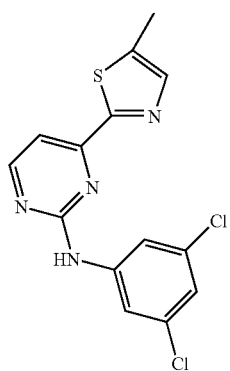
I-54
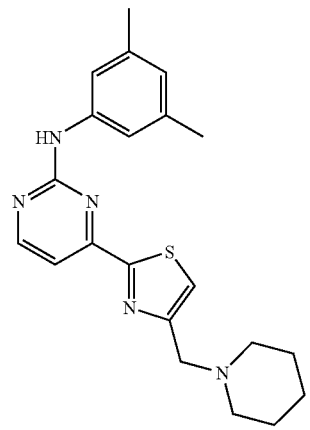
I-52
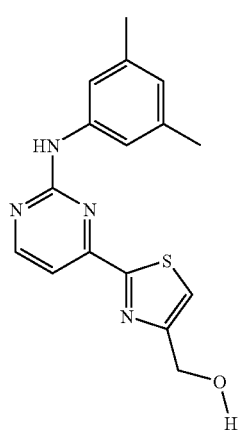
I-55
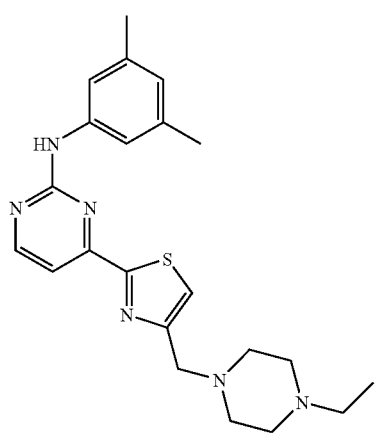
I-53
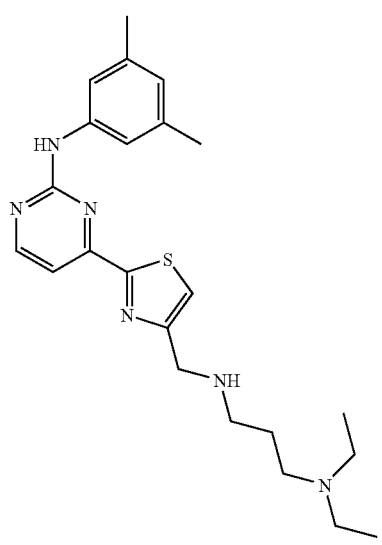
I-56
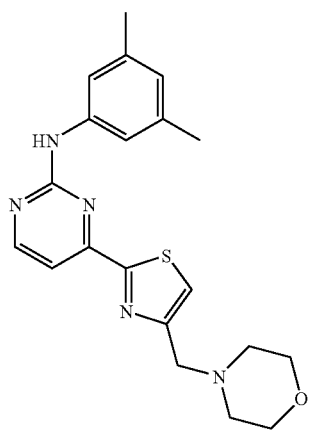

-continued
I-57
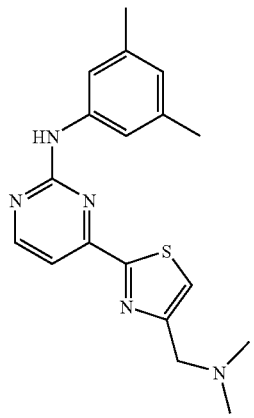
I-58
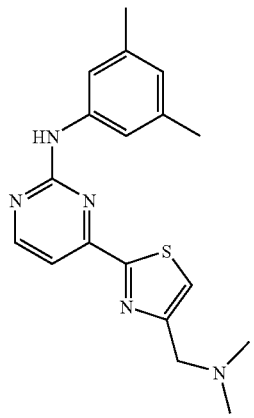
I-59
-continued
I-60
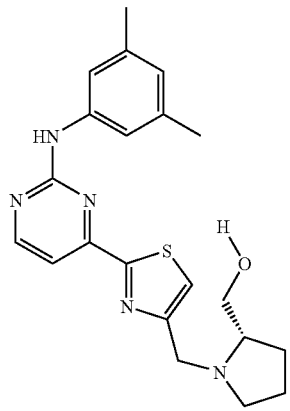
I-61
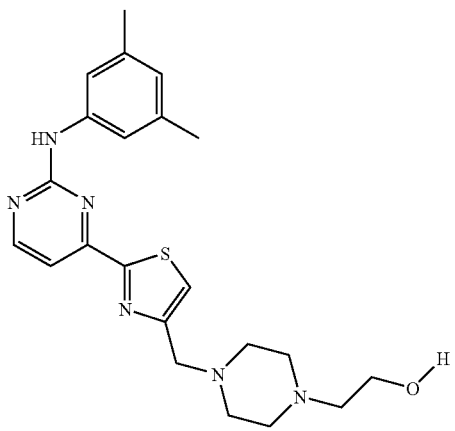
I-62
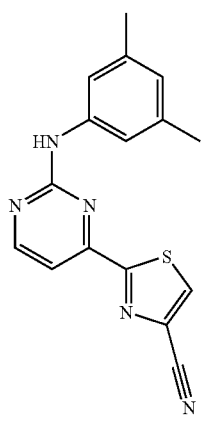
I-63
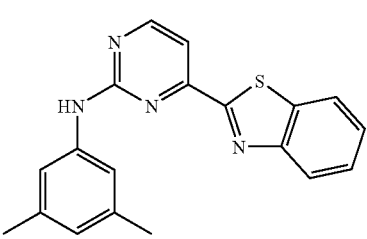

-continued
I-64
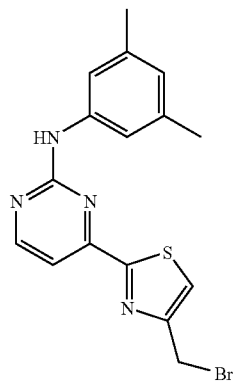
I-65
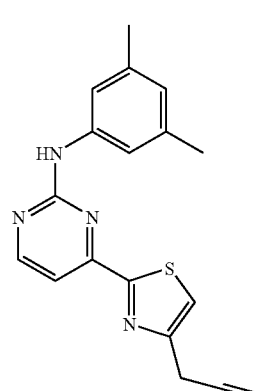
I-66
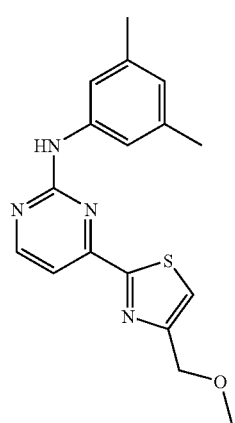
-continued
I-67
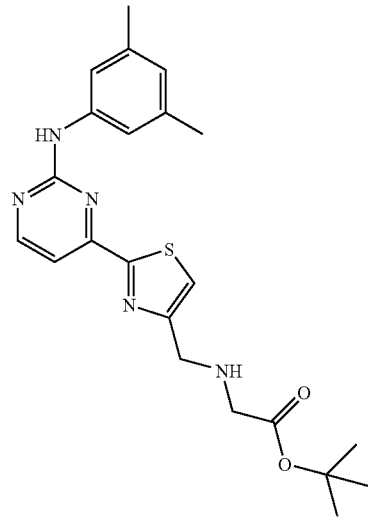
I-68
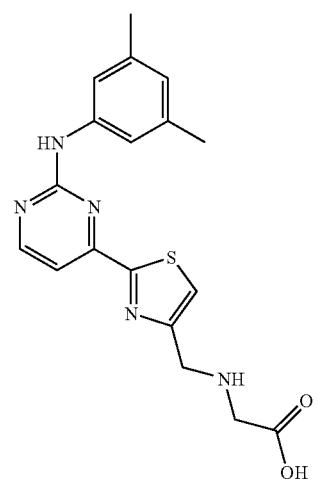
I-69
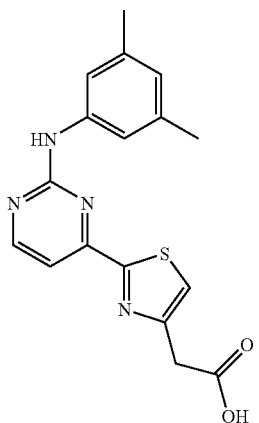

-continued
I-70
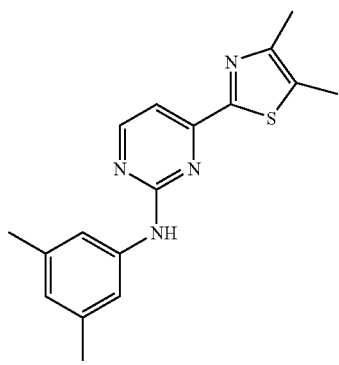
I-71
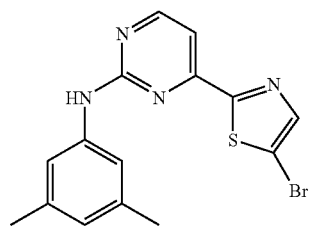
I-72
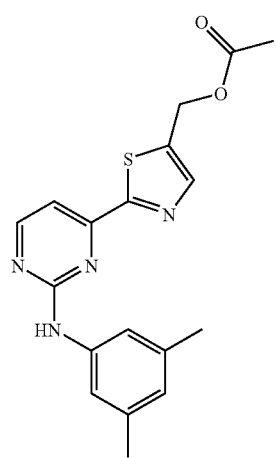
I-73
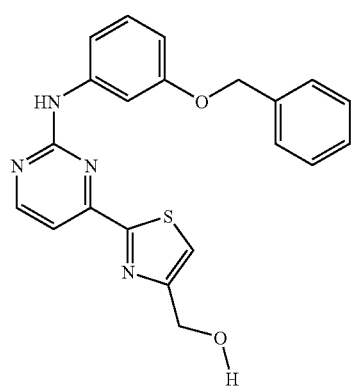
-continued
I-74
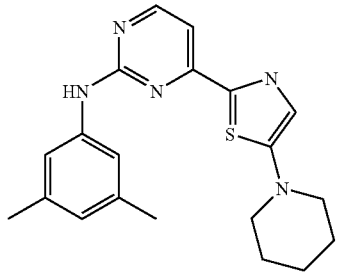
I-75
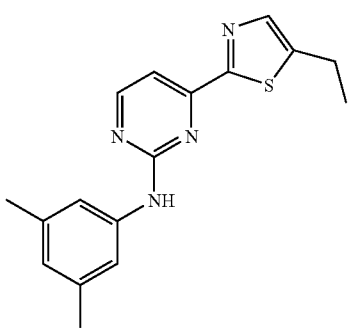
I-76
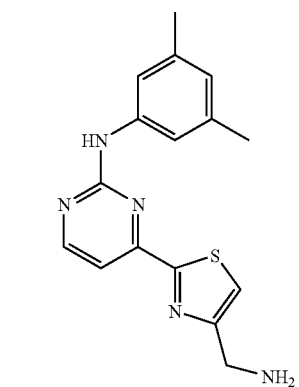
I-77
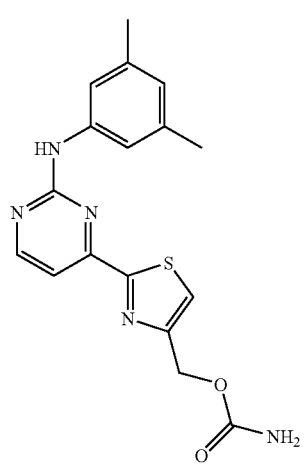

I-78 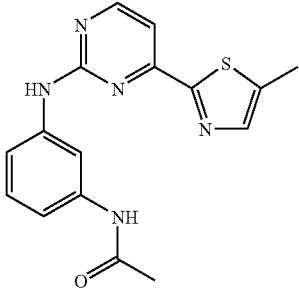
I-82 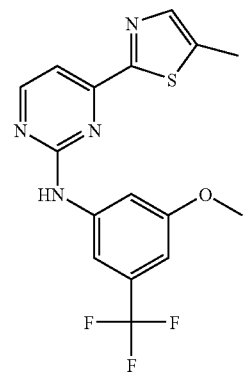
I-83 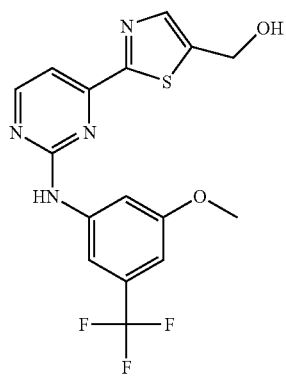
I-84 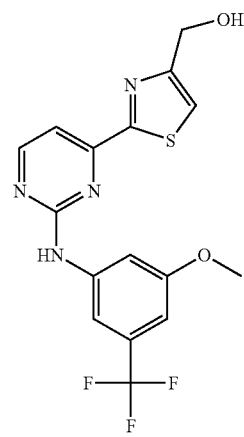
I-85 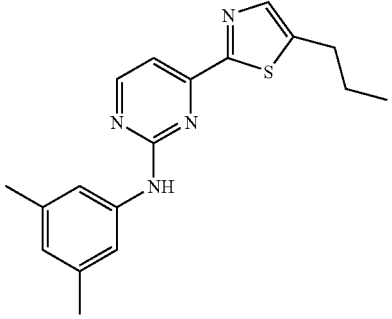
I-86 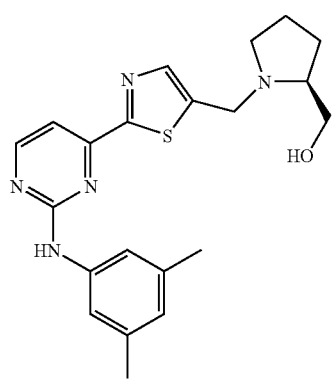
I-87 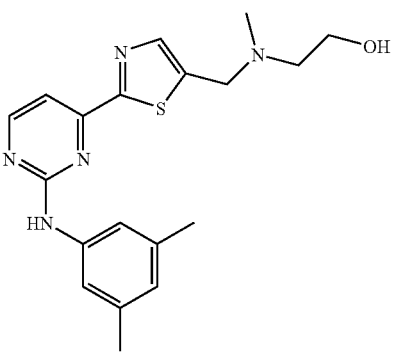
I-88 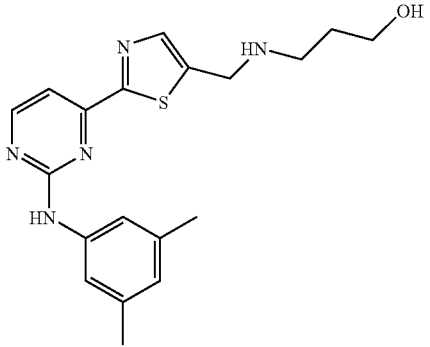

-continued
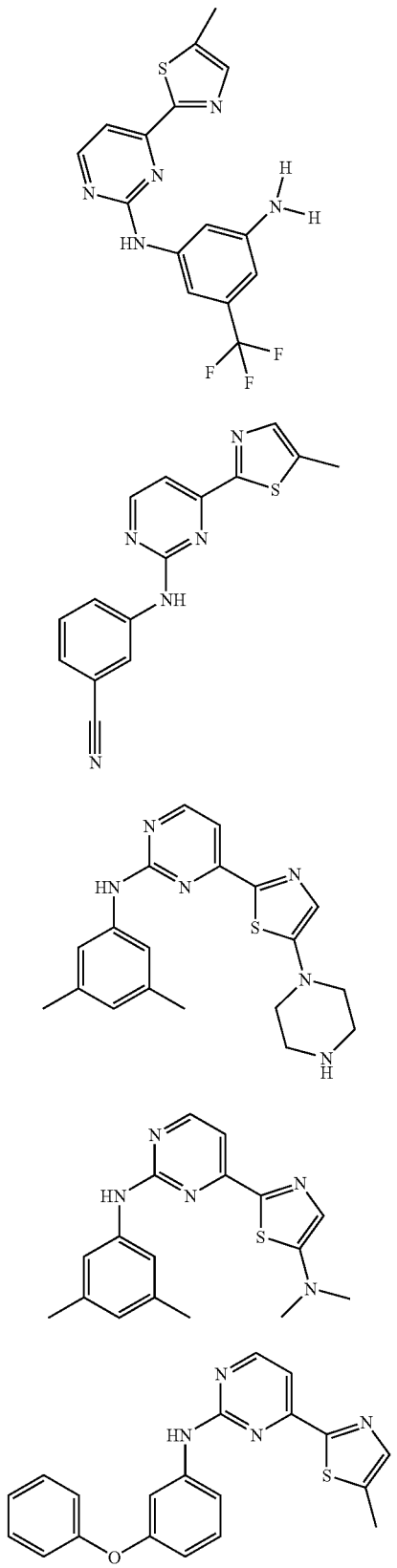
I-89
I-90
I-93
I-94
I-96
-continued
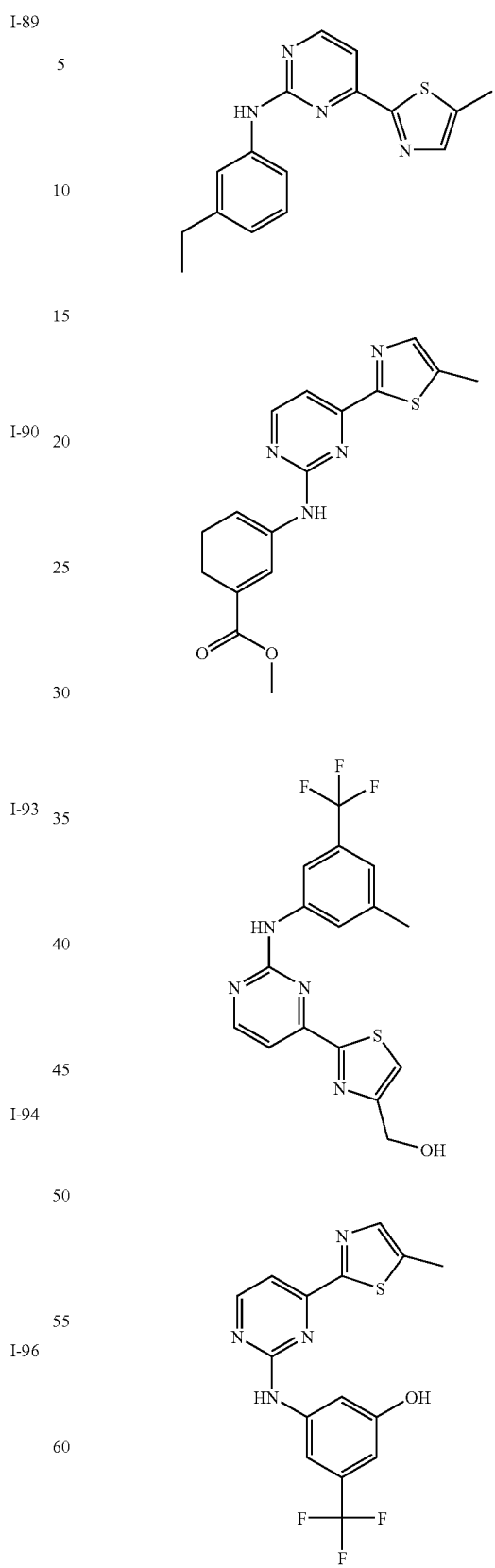
I-101
I-105
I-108
I-109

-continued
I-111
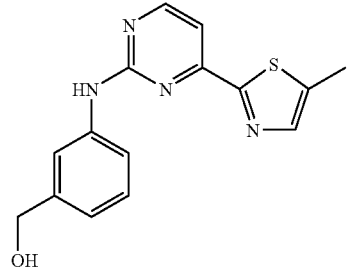
I-115
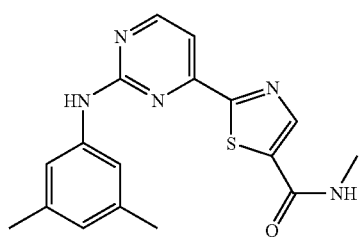
I-118
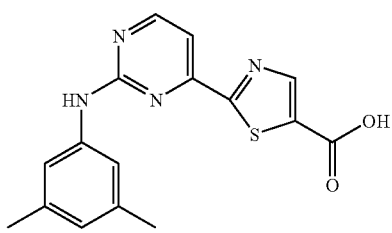
I-119
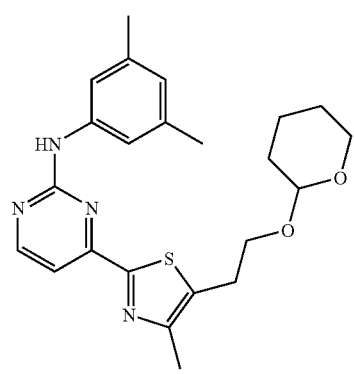
I-121
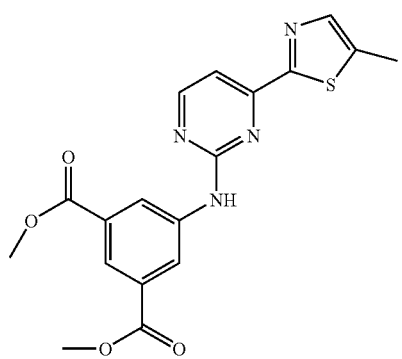
-continued
I-123
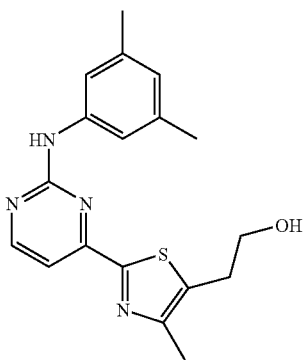
I-124
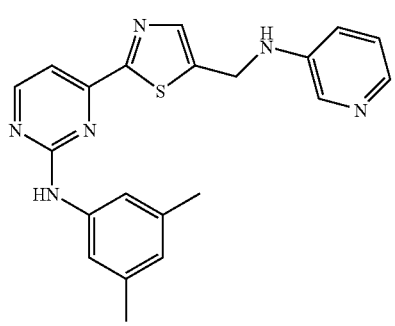
I-125
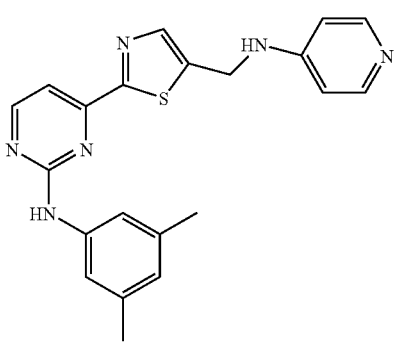
I-130
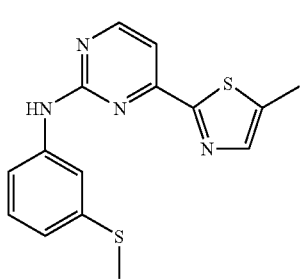

-continued
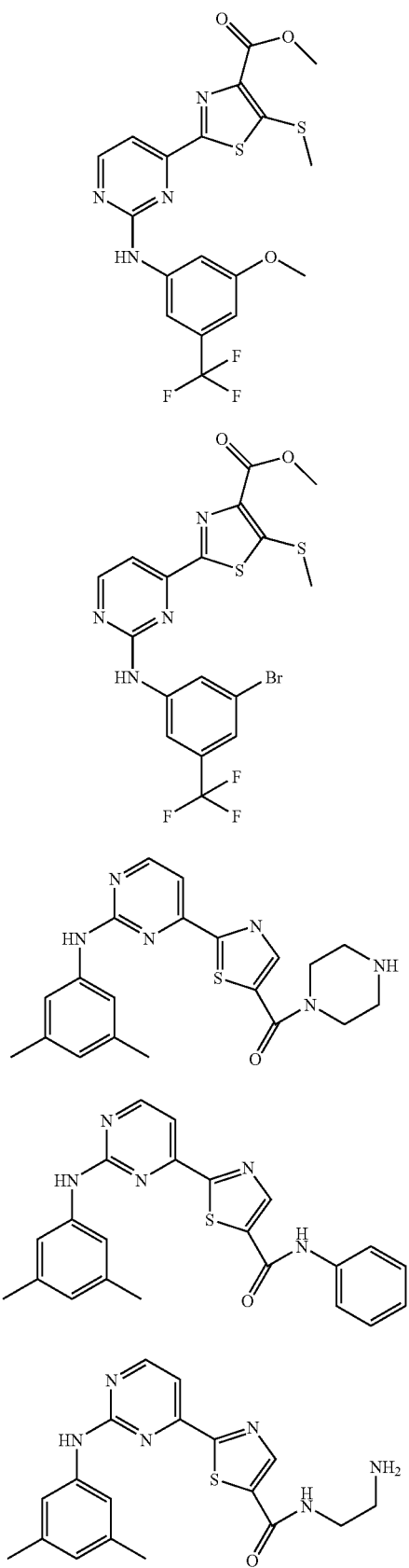
I-132
I-133
I-134
I-137
I-138
-continued
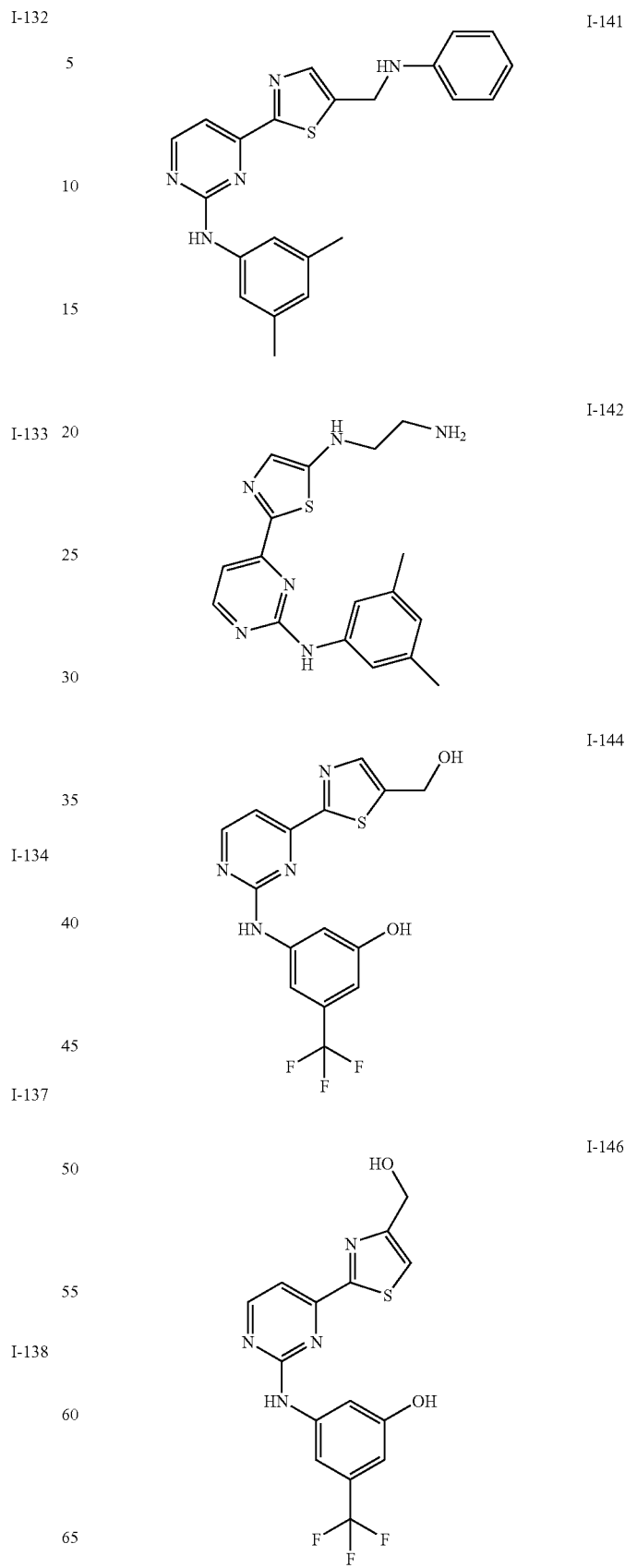
I-141
I-142
I-144
I-146

I-147
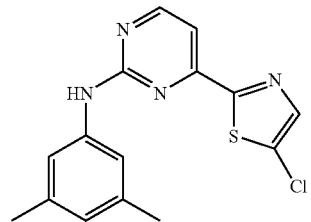
I-148
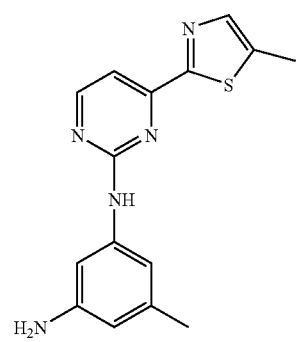
I-154
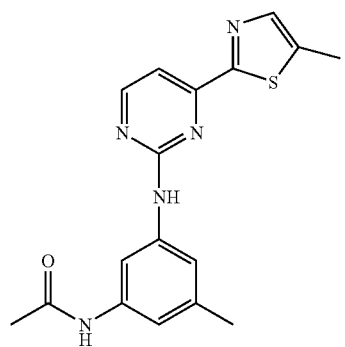
I-155
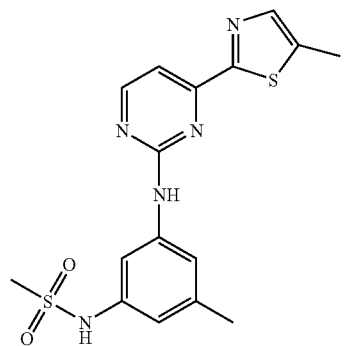
I-156
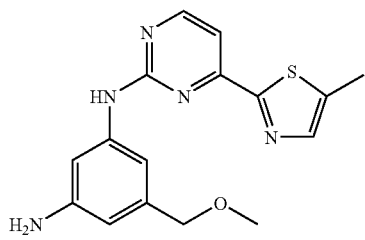
I-159
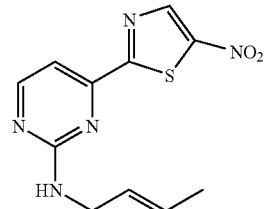
I-160
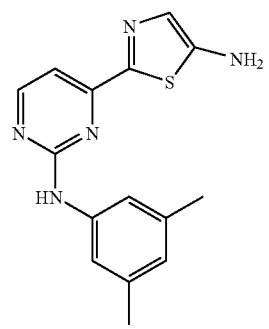
I-161
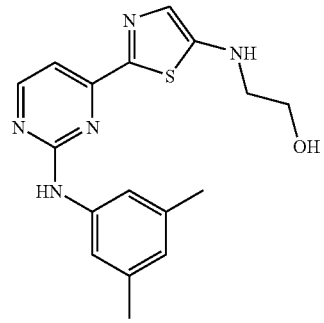
I-162
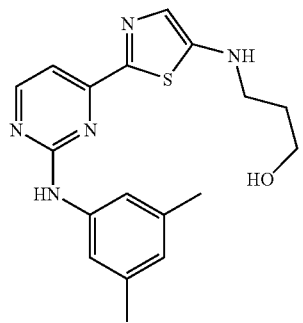
I-163
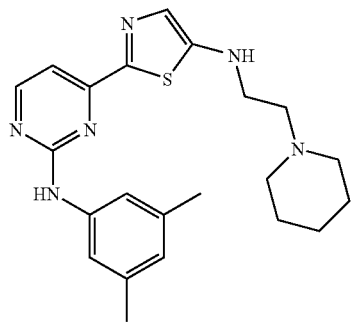

-continued
I-164
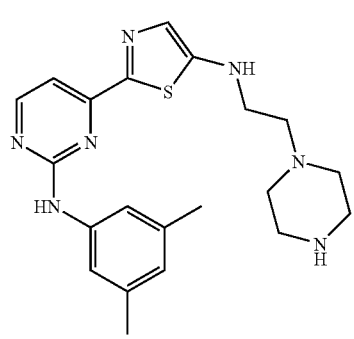
I-165
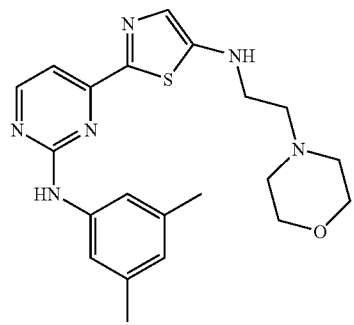
I-166
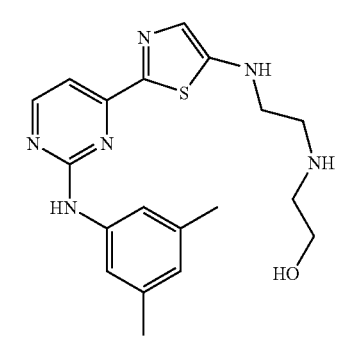
I-167
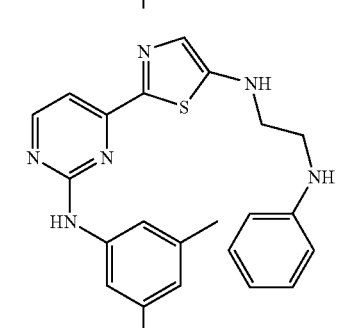
I-168
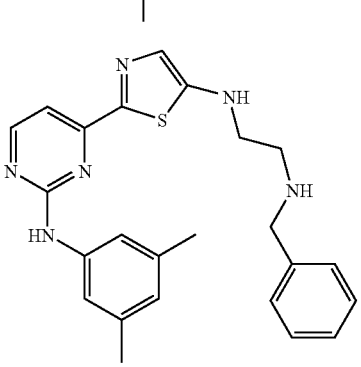
-continued
I-169
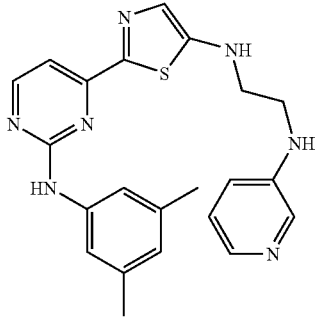
I-170
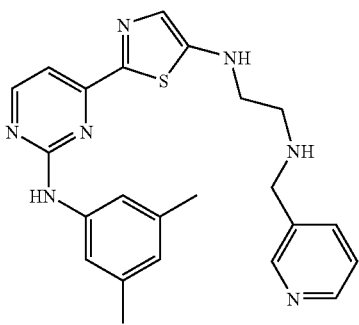
I-171
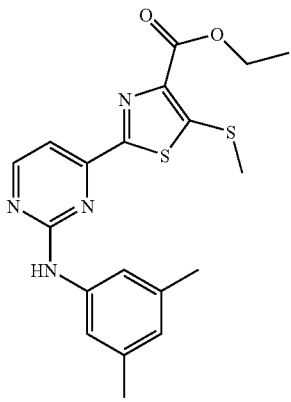
I-172
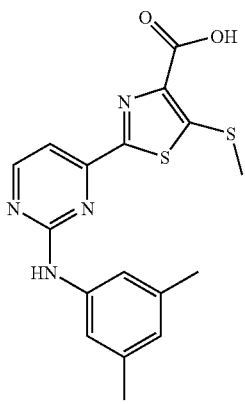

-continued
I-173
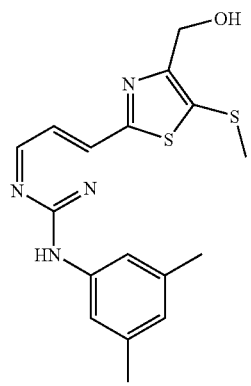
I-174
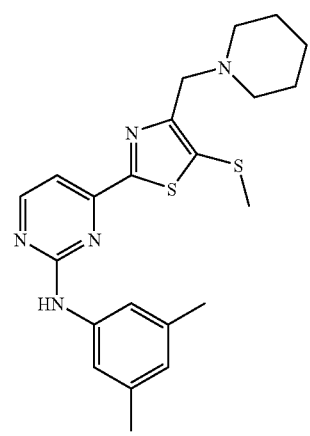
I-175
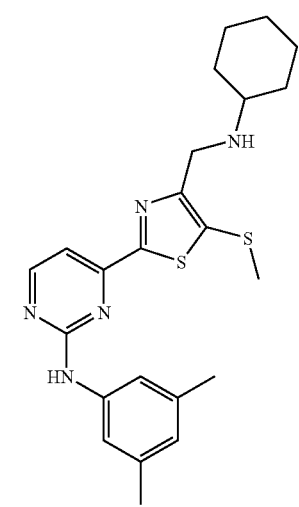
-continued
I-176
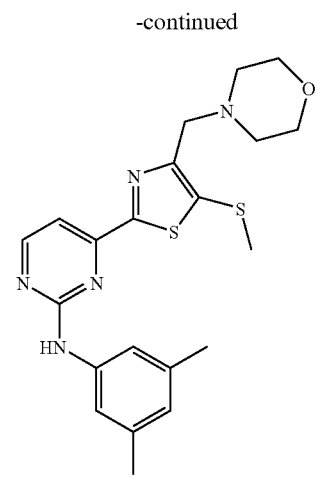
I-177
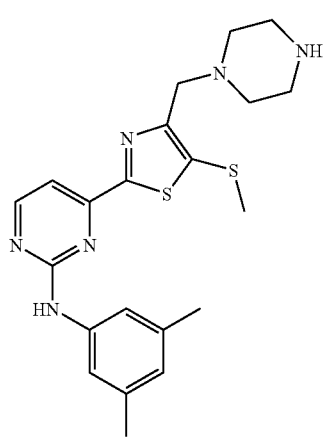
I-178
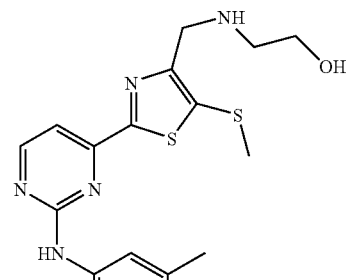
I-179
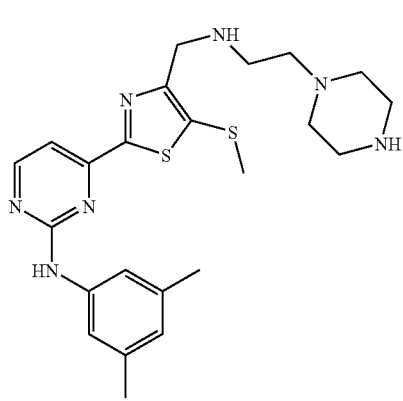

I-180
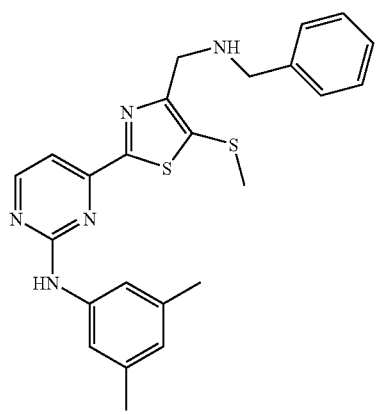
I-181
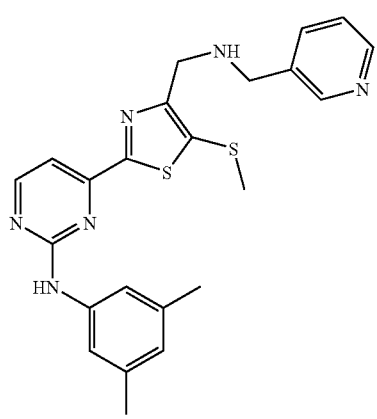
I-182
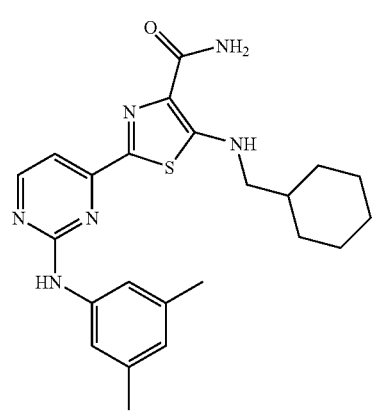
I-183
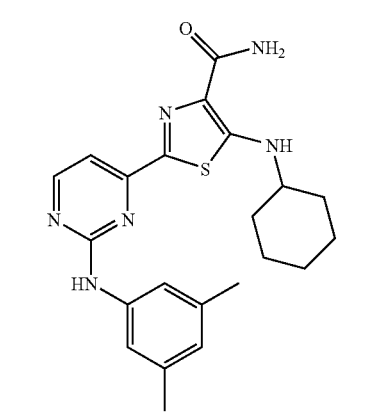
I-184
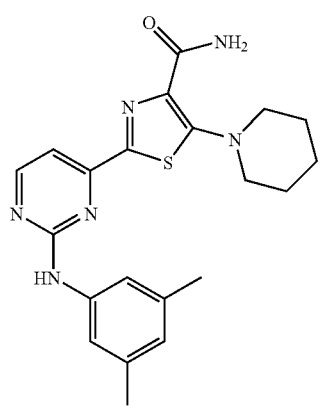
I-185
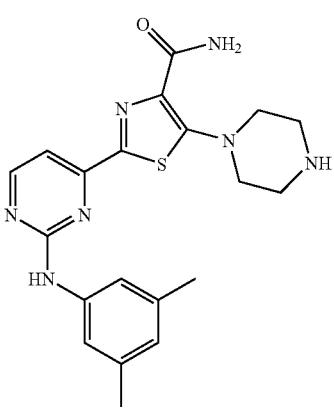
I-186
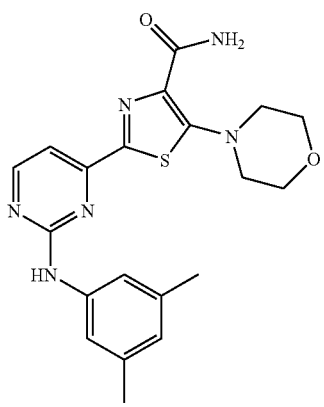
I-187
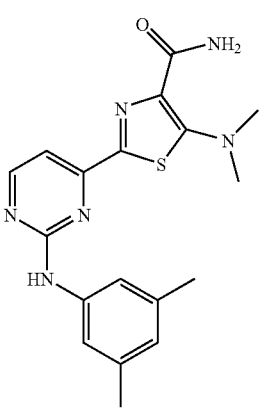

-continued
I-188 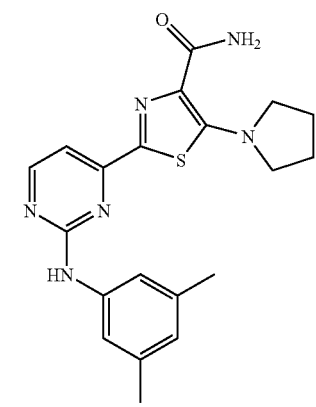
I-189 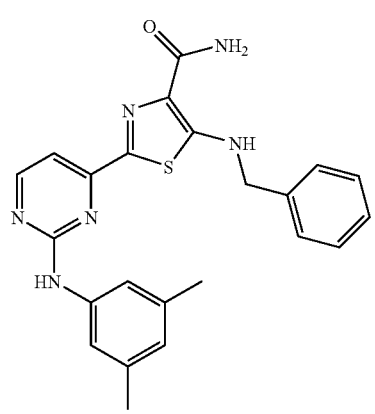
I-190 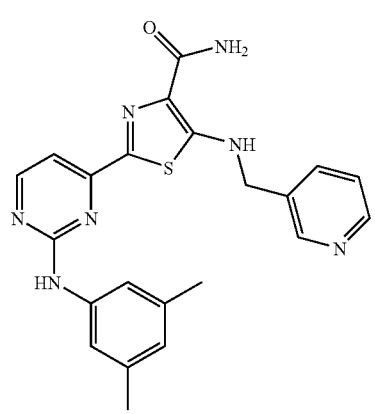
I-191 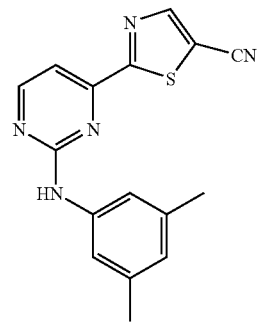
-continued
I-192 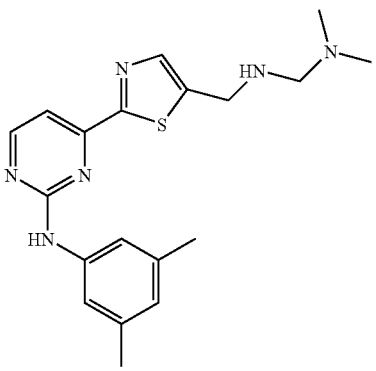
I-193 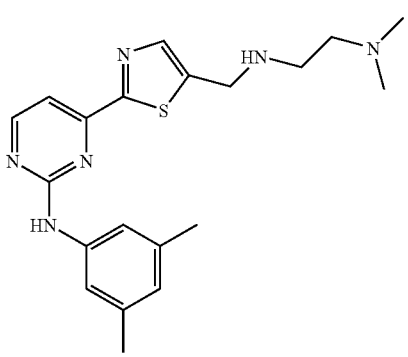
I-194 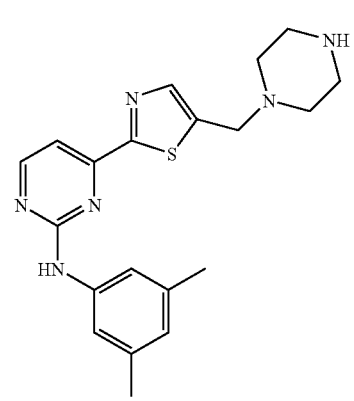
I-195 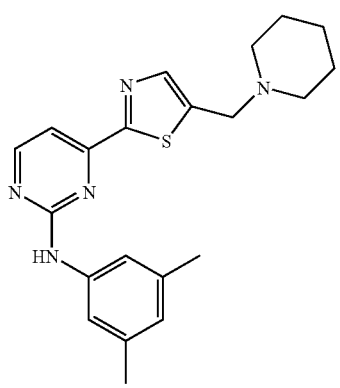

-continued
I-196
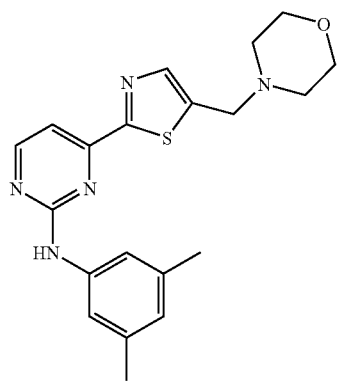
I-197
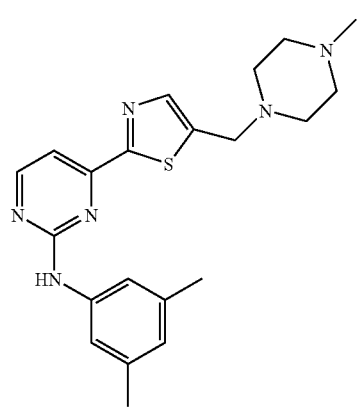
I-198
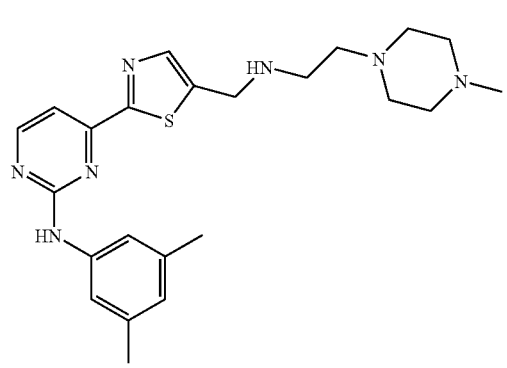
I-199
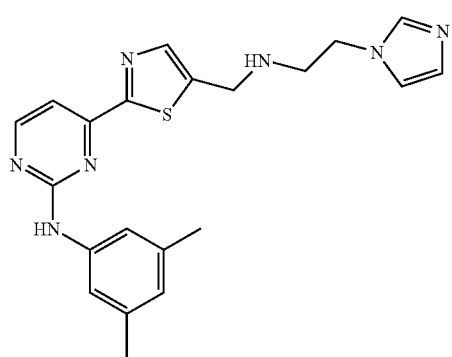
-continued
I-200
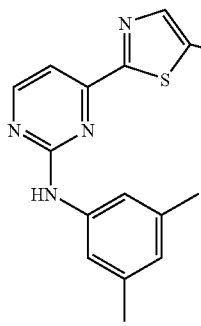
I-201
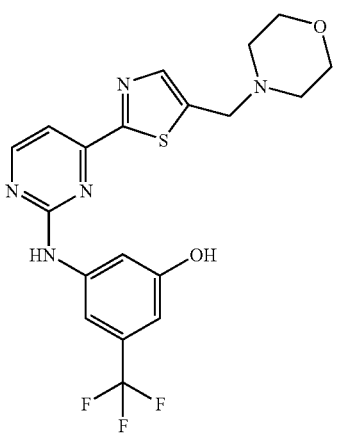
I-202
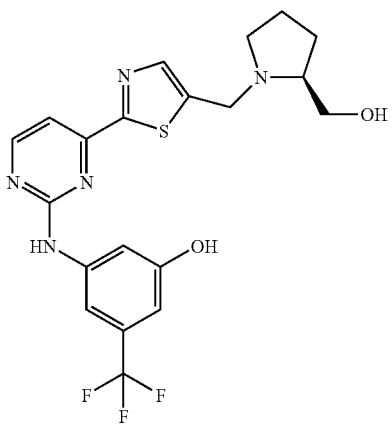

-continued
I-203
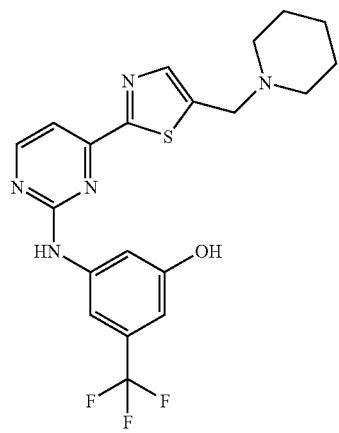
I-204
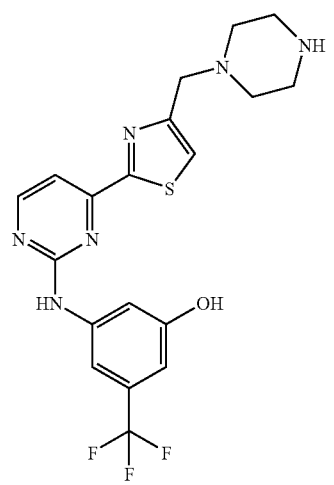
I-205
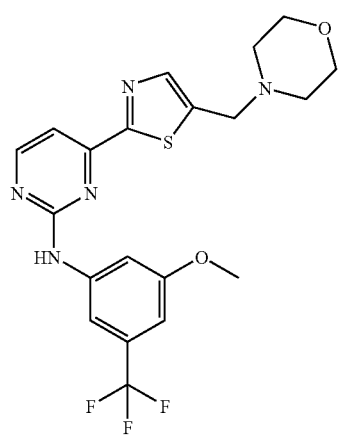
-continued
I-206
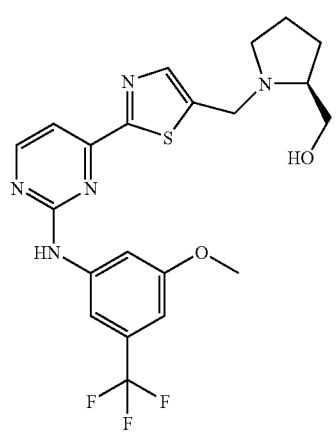
I-207
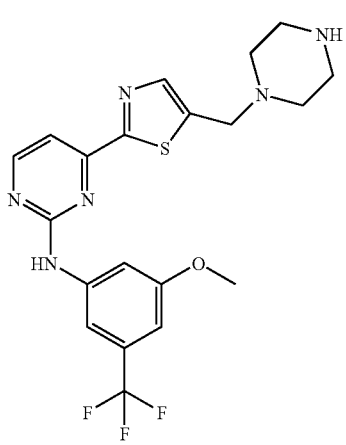
I-208
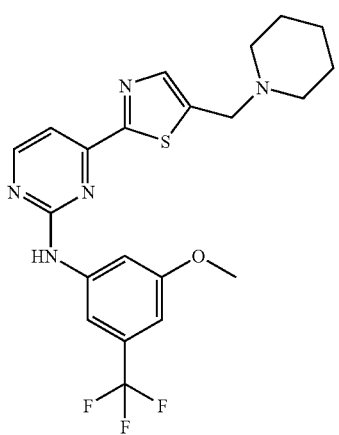

I-209
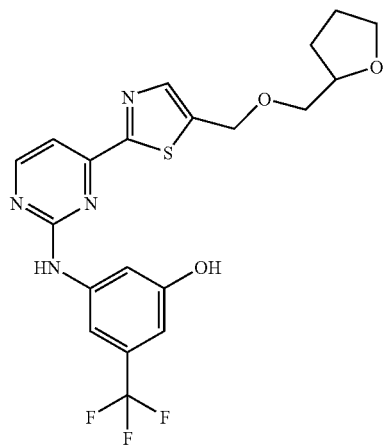
I-210
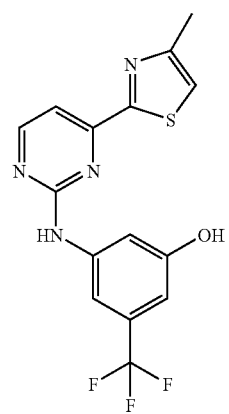
I-211
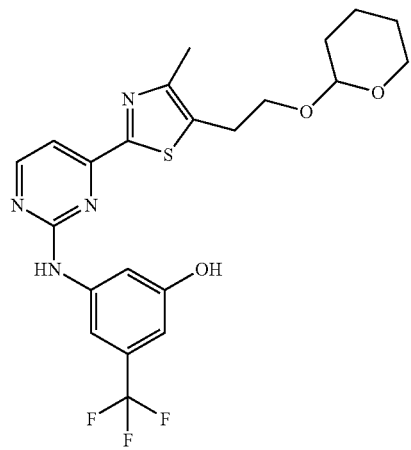
I-212
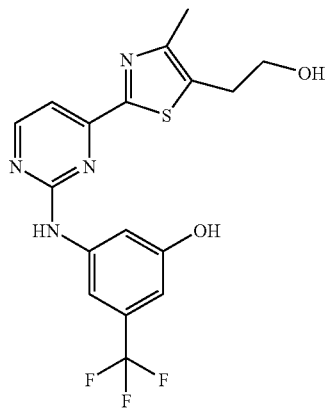
I-213
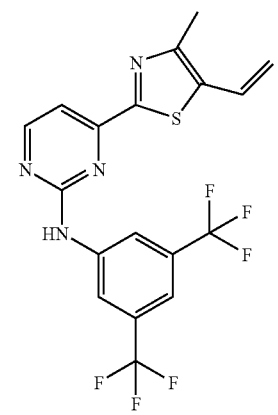
I-214
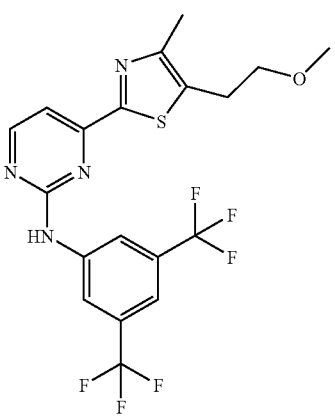
I-215
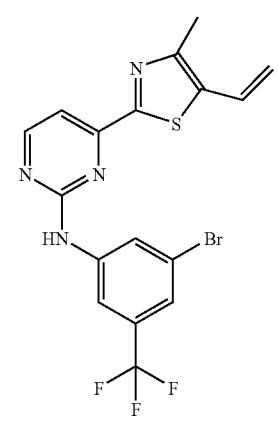

-continued
I-216
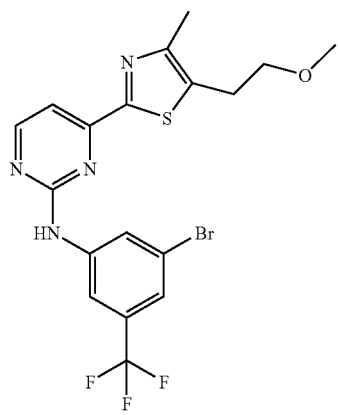
I-217
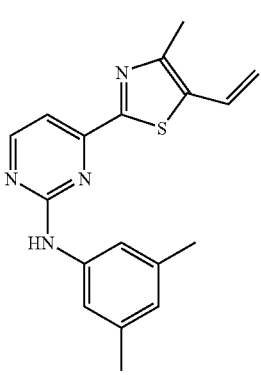
I-218
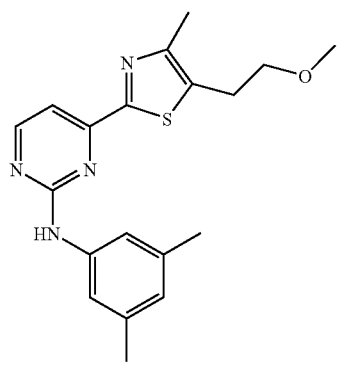
I-219
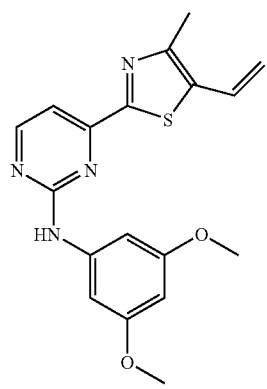
-continued
I-220
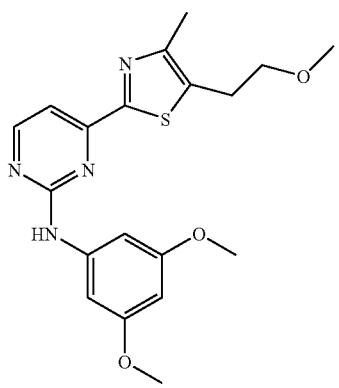
I-221
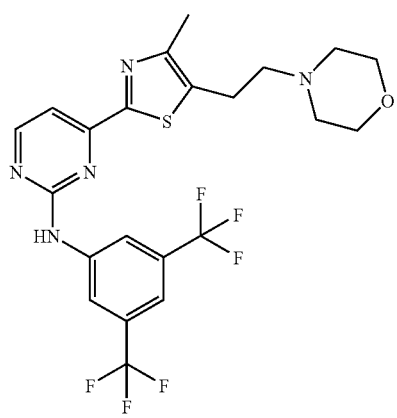
I-222
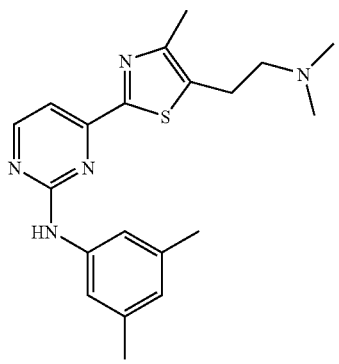
I-223
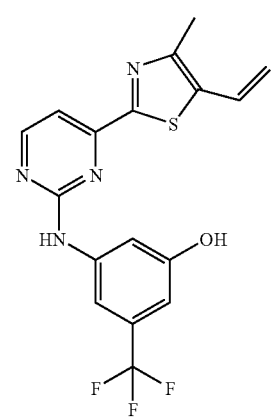

I-224 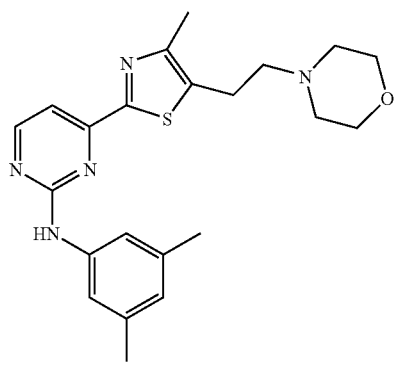
I-225 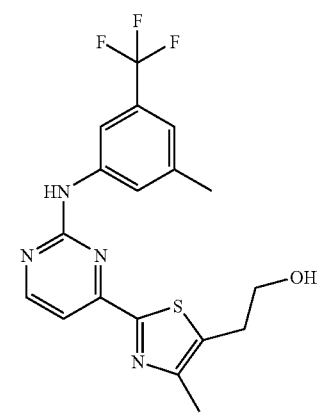
I-226 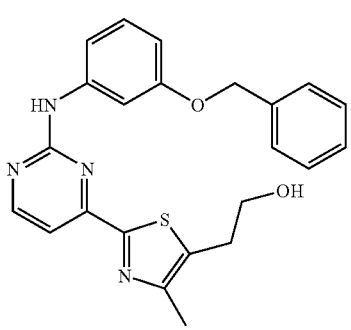
I-227 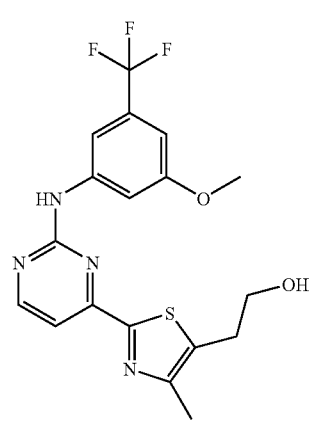
I-228 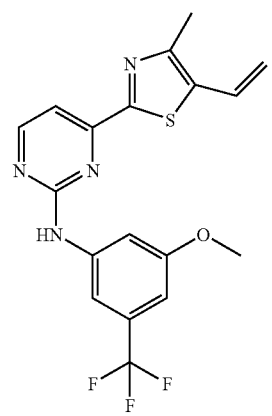
I-229 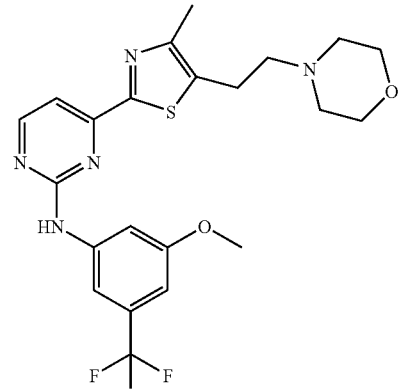
I-230 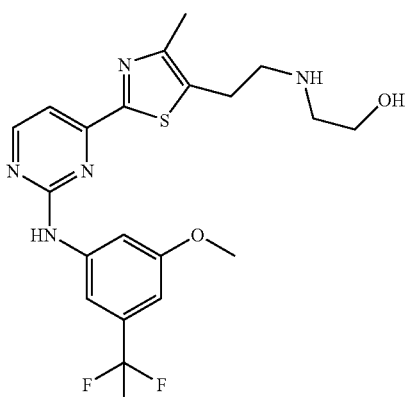
I-231 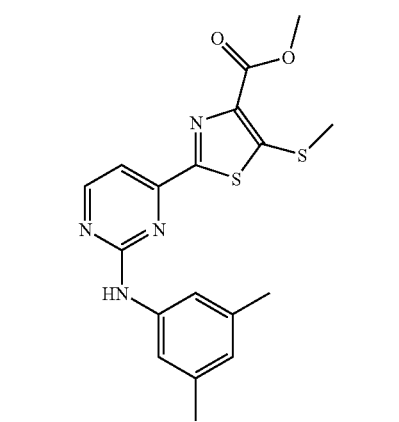

-continued
I-232
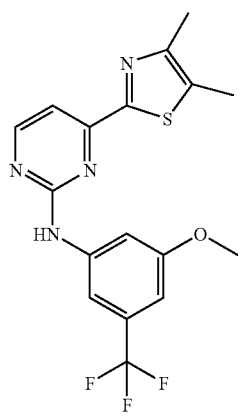
I-233
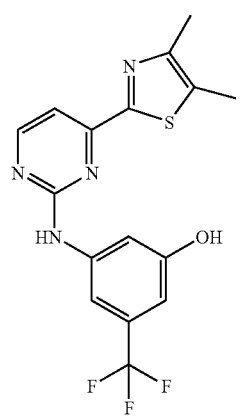
I-234
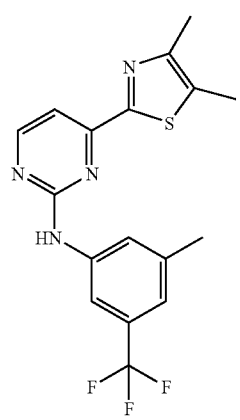
I-235
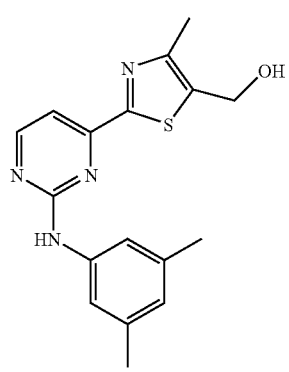
-continued
I-236
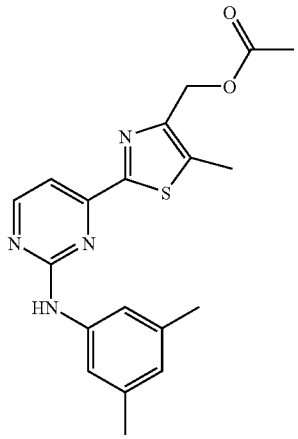
I-237
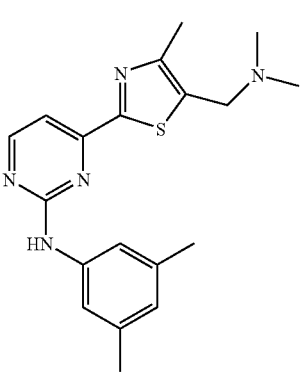
I-238
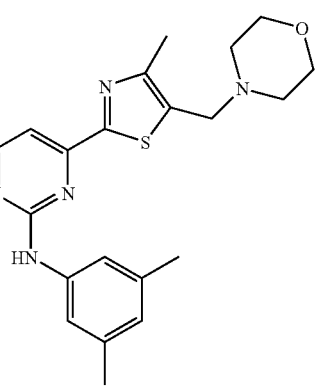
I-239
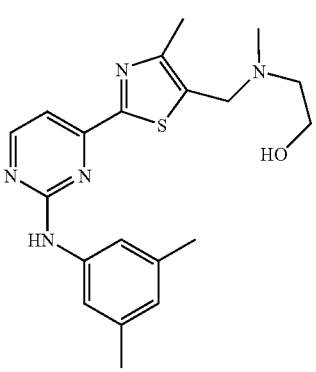

I-240
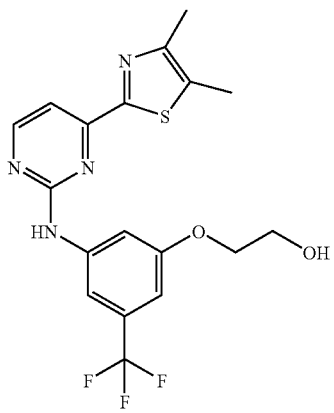
I-241
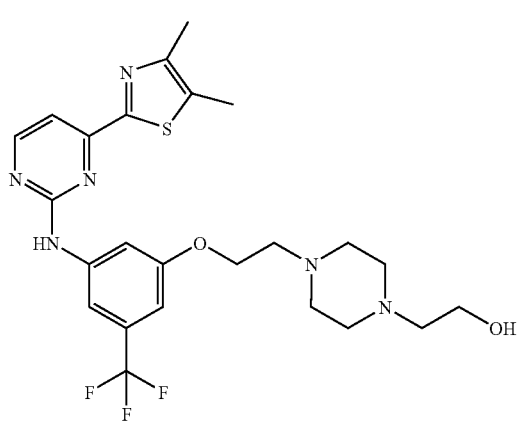
I-242
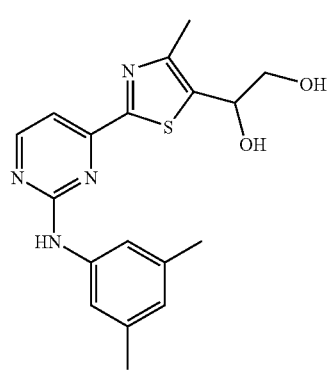
I-243
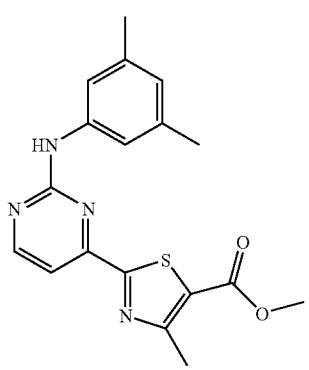
I-244
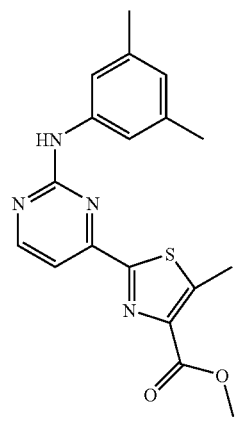
I-245
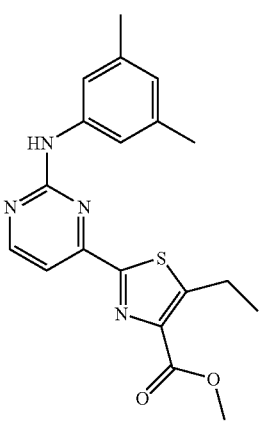
I-246
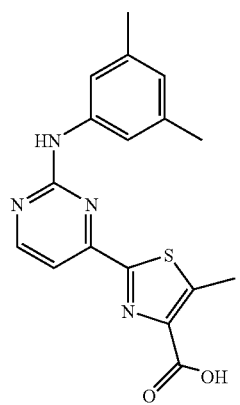
I-247

-continued
I-248
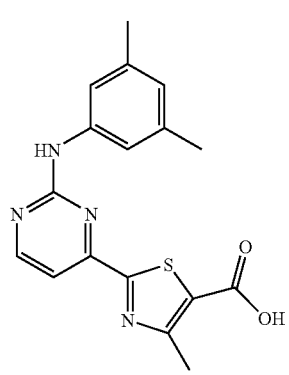
I-249
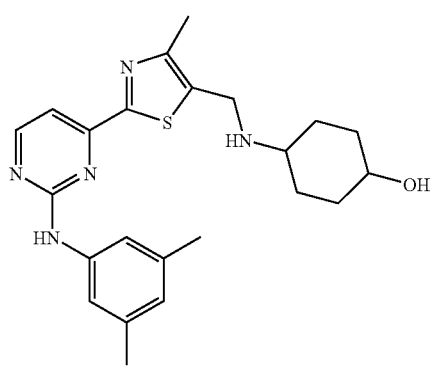
I-250
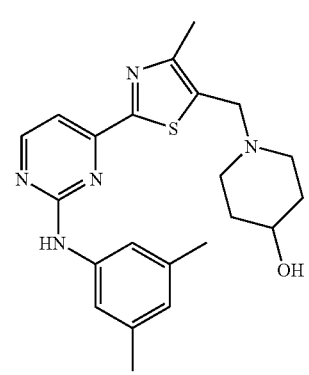
I-251
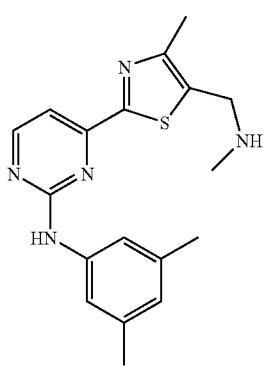
-continued
I-252
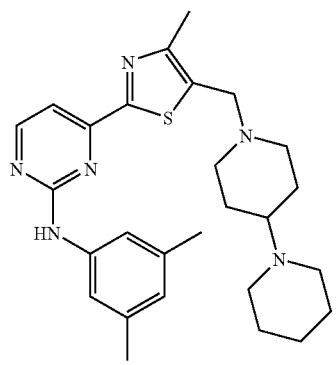
I-253
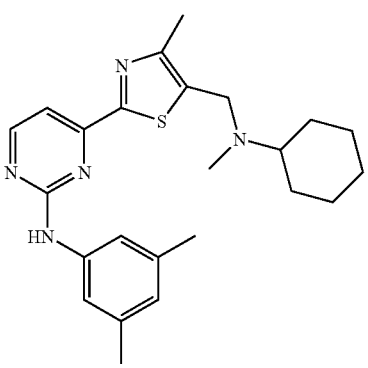
I-254
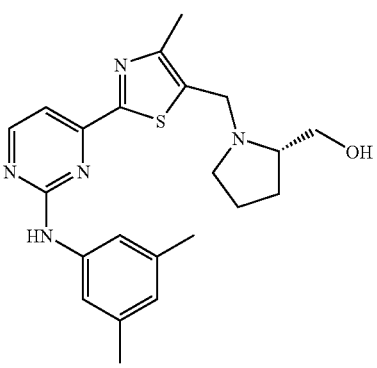
I-255

I-256
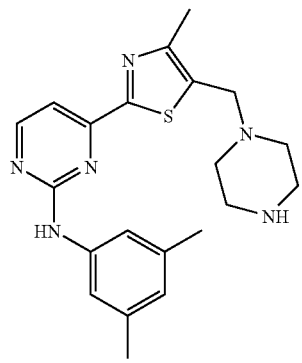
I-257
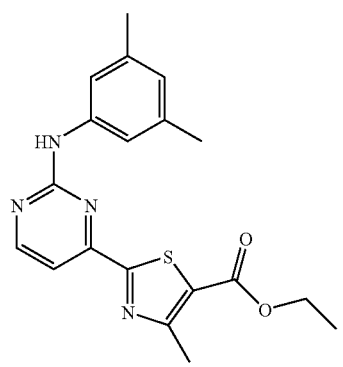
I-258
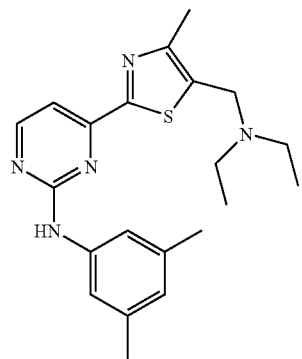
I-259
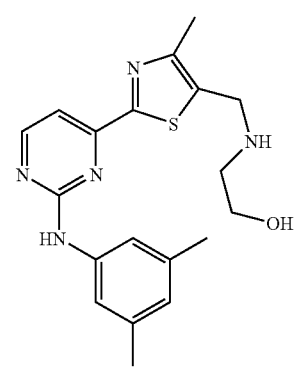
I-260
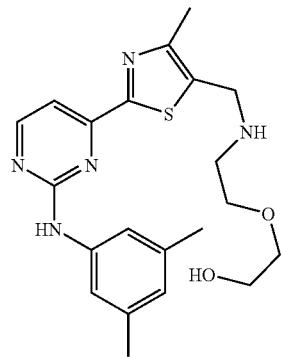
I-261
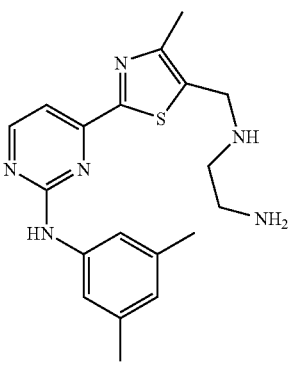
I-262
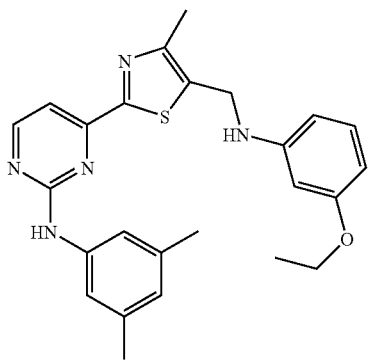
I-263
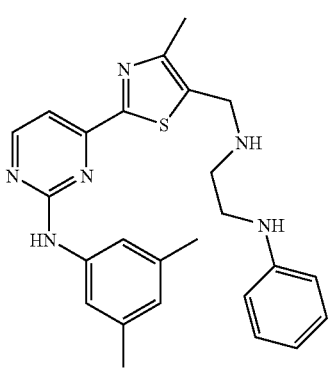

-continued
I-264
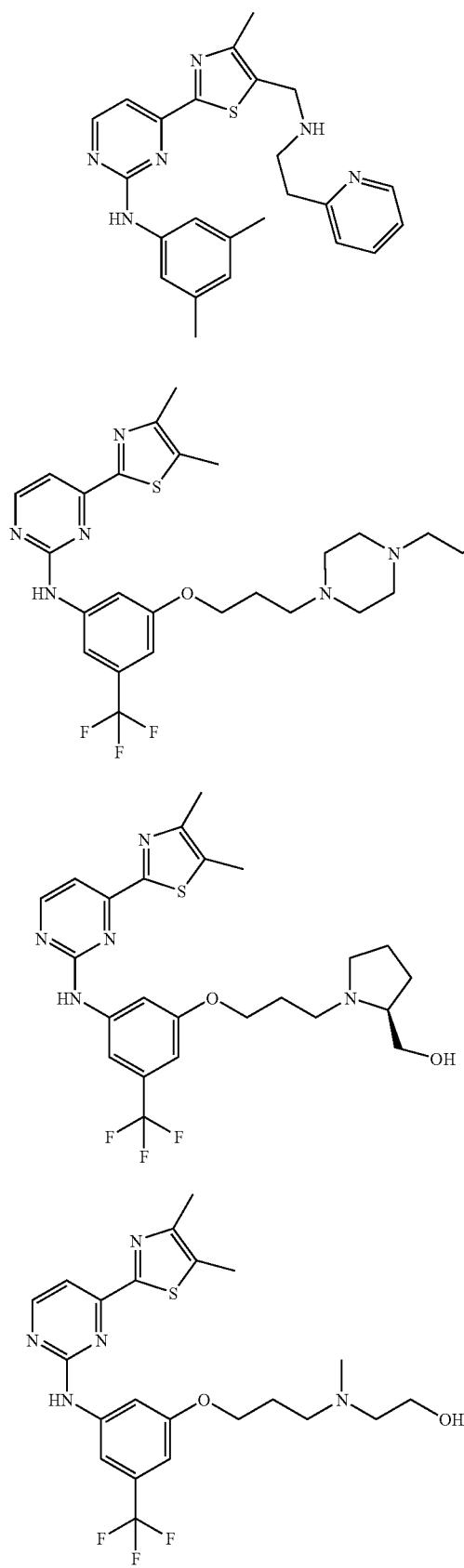
I-265
I-266
I-267
-continued
I-268
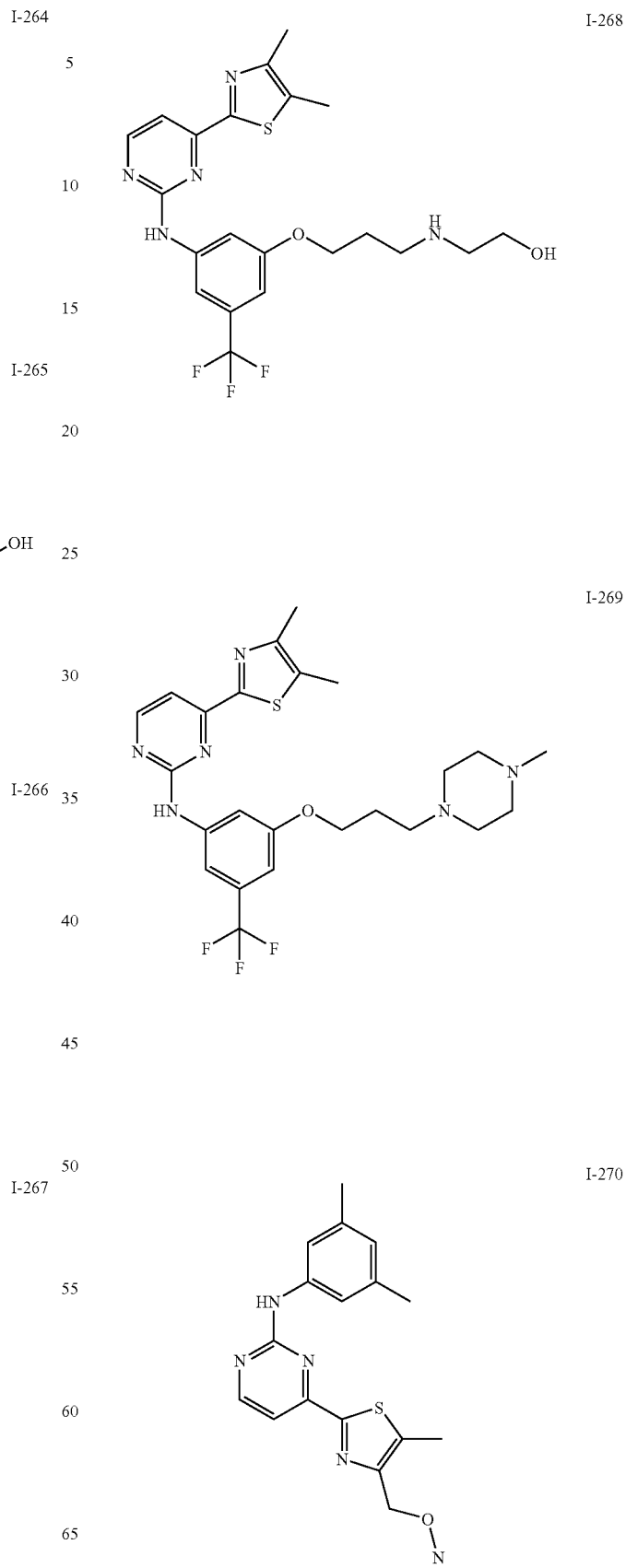
I-269
I-270

-continued
I-271
I-272
I-273
I-274
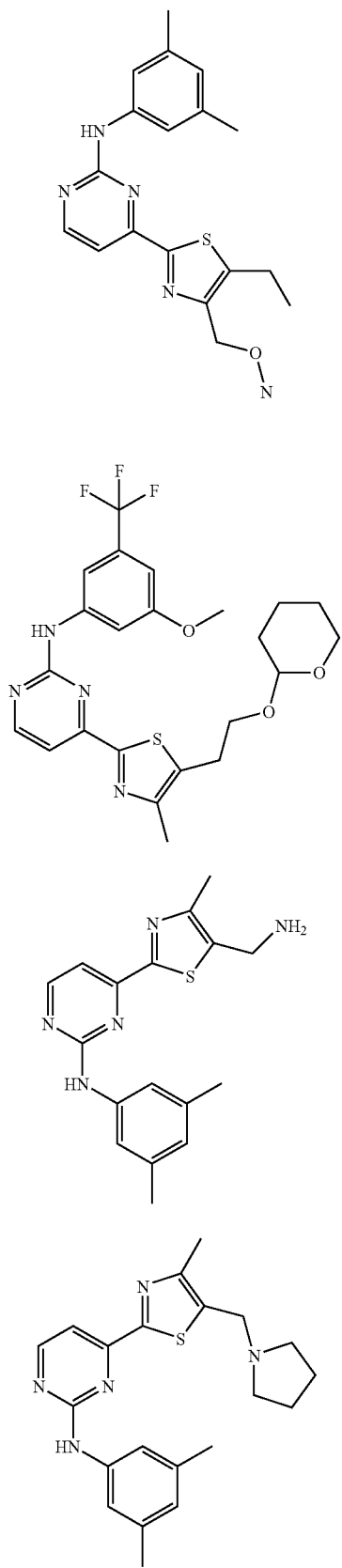
-continued
I-275
I-276
I-277
I-278
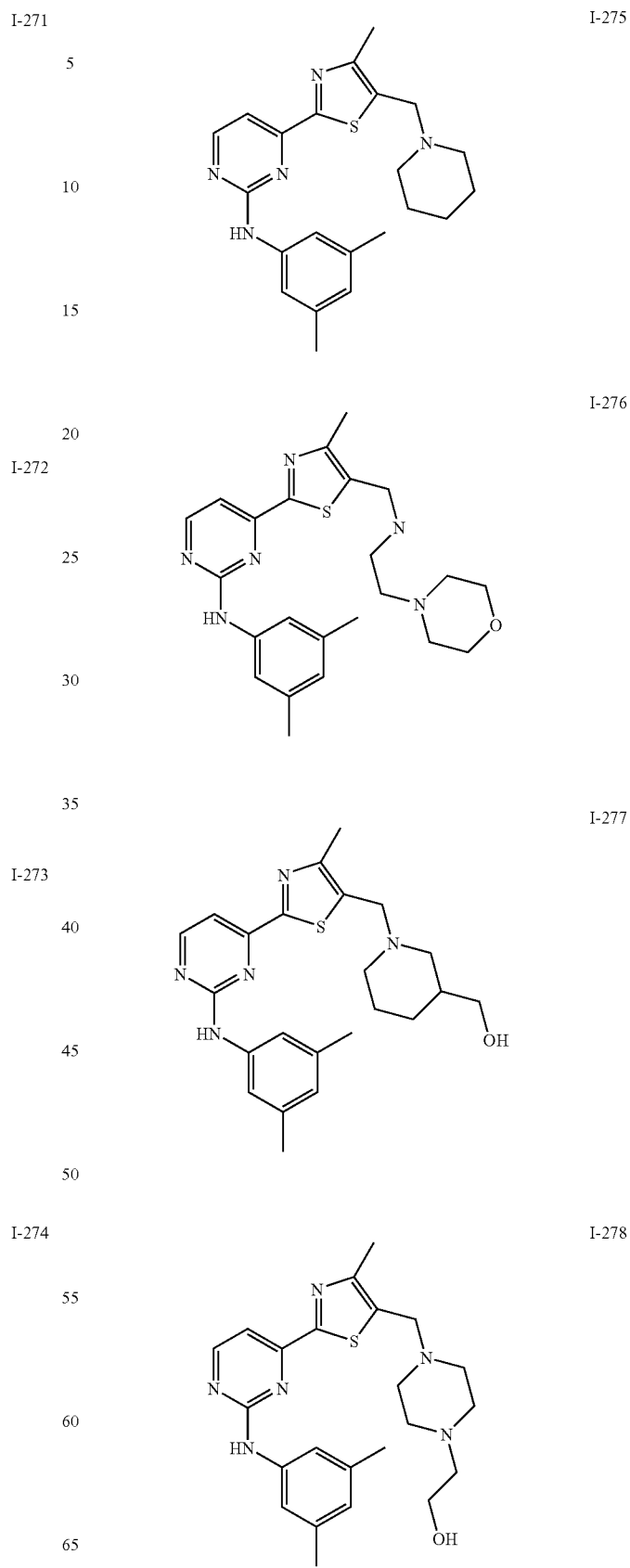

-continued
I-279
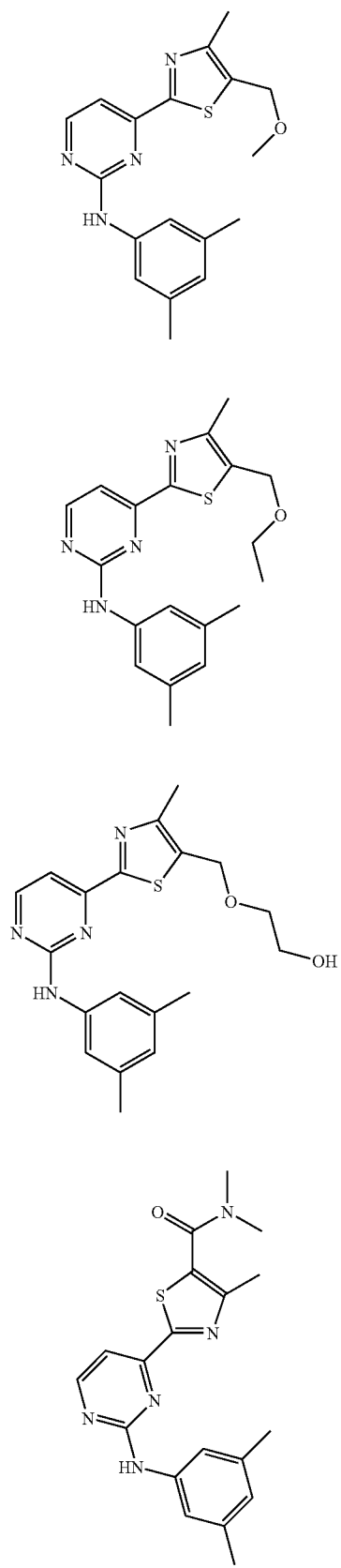
I-280
I-281
I-282
I-283
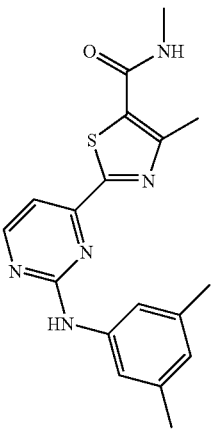
I-284
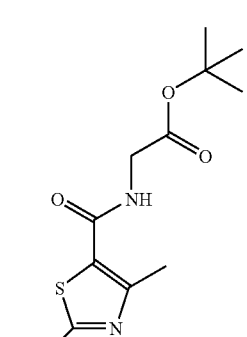
I-285
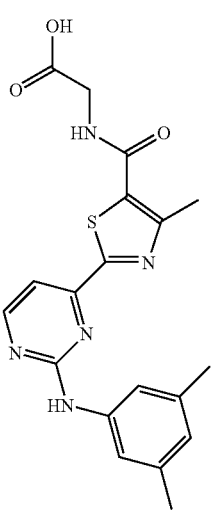

-continued

I-286

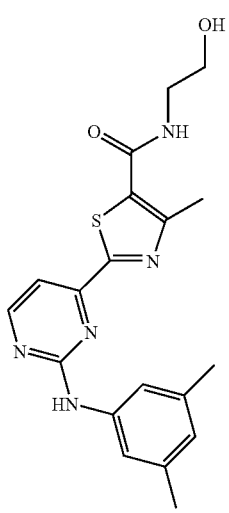

24. A composition comprising a compound of claim 1, and a pharmaceutically acceptable carrier, adjuvant, or vehicle.

25. A method of treating or lessening the severity of multiple sclerosis, lupis erythematosus, rheumatoid arthritis, or asthma in a patient, comprising the step of administering to said patient:

a) a composition of claim 24; or b) a compound of claim 1.

26. The method according to claim 25, wherein the disease is rheumatoid arthritis.

27. The method according to claim 25, wherein the disease is asthma.

* * * * *